US007897839B2

(12) United States Patent
Pennell et al.

(10) Patent No.: US 7,897,839 B2
(45) Date of Patent: Mar. 1, 2011

(54) METHODS FOR MODIFYING PLANT CHARACTERISTICS

(75) Inventors: Roger I. Pennell, Malibu, CA (US); Chuan-Yin Wu, Newbury Park, CA (US); Hongyu Zhang, Los Angeles, CA (US)

(73) Assignee: Ceres, Inc., Thousand Oaks, CA (US)

( * ) Notice: Subject to any disclaimer, the term of this patent is extended or adjusted under 35 U.S.C. 154(b) by 579 days.

(21) Appl. No.: 11/112,824

(22) Filed: Apr. 22, 2005

(65) Prior Publication Data

US 2006/0021089 A1    Jan. 26, 2006

Related U.S. Application Data

(60) Provisional application No. 60/644,612, filed on Jan. 18, 2005, provisional application No. 60/565,031, filed on Apr. 23, 2004.

(51) Int. Cl.
    A01H 5/00       (2006.01)
    C12N 5/14       (2006.01)
    C12N 15/82      (2006.01)
(52) U.S. Cl. ...... 800/295; 800/312; 800/320; 800/320.1; 800/320.2; 435/419; 435/468
(58) Field of Classification Search .................. None
    See application file for complete search history.

(56) References Cited

U.S. PATENT DOCUMENTS

| 5,859,326 A | 1/1999 | An .................................. 800/290 |
| 5,952,545 A | 9/1999 | Koncz et al. ..................... 800/298 |
| 6,545,200 B1 | 4/2003 | Cahoon et al. .................. 800/278 |
| 2004/0060079 A1 | 3/2004 | Tanaka et al. |
| 2006/0048240 A1* | 3/2006 | Alexandrov et al. ......... 800/278 |
| 2006/0150283 A1* | 7/2006 | Alexandrov et al. ......... 800/288 |
| 2006/0236419 A1* | 10/2006 | La Rosa et al. ............... 800/278 |
| 2007/0214517 A1* | 9/2007 | Alexandrov et al. ......... 800/278 |

FOREIGN PATENT DOCUMENTS

| CA | 2422620 | 3/2004 |
| JP | 2002-276398 | 4/2004 |
| WO | WO 97/35986 | 10/1997 |
| WO | WO 99/32619 | 7/1999 |
| WO | WO 99/53050 | 10/1999 |
| WO | WO 00/47715 | 8/2000 |
| WO | WO 01/75164 | 10/2001 |
| WO | WO 02/46449 | 6/2002 |
| WO | 2007/064724 | 6/2007 |

OTHER PUBLICATIONS

Wells, (Biochemistry 29:8509-8517, 1990).*
Ngo et al., (The Protein Folding Problem and Tertiary Structure Prediction, K. Merz., and S. Le Grand (eds.) pp. 492-495, 1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
GenBank Accession No. AC104473, dated Oct. 30, 2002.
GenBank Accession No. AF044216, dated Jun. 25, 2001.
GenBank Accession No. X87368, Dated Oct. 7, 1996.
GenBank Accession No. U54770, Dated Oct. 18, 1996.
GenBank Accession No. M13785, Dated Apr. 27, 1993.
GenBank Accession No. D64003, Dated Jul. 4, 2001.
GenBank Accession No. U32579, Dated Sep. 15, 1995.
GenBank Accession No. U68234, Dated Nov. 22, 1996.
GenBank Accession No. X70981, Dated Jan. 18, 1994.
GenBank Accession No. P48421, Dated May 16, 2006.
GenBank Accession No. AL049659, Dated Apr. 16, 2005.
GenBank Accession No. P48418, Dated May 16, 2006.
GenBank Accession No. X71658, Dated Apr. 18, 2005.
Adams et al., Parent-of-origin effects on seed development in *Arabidopsis thaliana* require DNA methylation, *Development*, 2000, 127:2493-2502.
Akama et al., "Efficient Transformation of *Arabidopsis thaliana*: Comparison of the Efficiencies With Various Organs, Plant Ecotypes and Agrobacterium Strains," *Plant Cell Rep.*, 1992, 12:7-11.
Asami et al, "Selective Interaction of Triazole Derivative with DWF4, a Cytochrome P450Monooxygenase of the Brassinosteroid Biosynthetic Pathway, Corrselates with Brassinosteroid Deficiency in Planta" *The Journal of Biological Chemistry*, Jul. 13, 2001, 276(26):25687-25691.
Azprioz et al., "An *Arabidopsis* Brassinosteroid-Dependent Mutant Is Blocked in Cell Elongation," *The Plant Cell*, 1998, 10:219-230.
Barendse et al., "The role of Endogenous Gibberellins During Fruit and Seed Development: Studies on Gibberellin-Deficient Genotypes of *Arabidopsis thaliana*," *Physiol. Plant*, 1986, 67:315-319.
Bishop et al., "The Tomato *Dwarf* Gene Isolated by Heterologous Transposon Tagging Encodes the First Member of a New Cytochrome P450 Family," *Plant Cell*, 1996, 8:959-969.
Bishop and Koncz, "Brassinosteroids and Plant Steroid Hormone Signaling," *The Plant Cell*, (Supplement) 2002, S97-S110.
Bonner et al., "Reduction in the rate of DNA reassociation by sequence divergence" *J. Mol. Biol.*, 1973, 81:123.
Branch, "A good antisense molecule is hard to find," *TIBS*, 23:45-50.
Choe et al., "*Arabidopsis* dwarf mutants define eight genes involved in brassinosteroid biosynthesis and signal transduction," *Plant Biology*, 1998, p. 10, Annual Meeting of the American Society of Plant Physiologists, Madison, WI, Jun. 27-Jul. 1, 1998.
Choe et al., "*Arabidopsis* dwarf mutants define the genes involved in brassinosteroid biosynthesis," *Plant Biology*, 1998, p. 133, Annual Meeting of the American Society of Plant Physiologists, Madison, WI, Jun. 27-Jul. 1, 1998.
Choe et al., "The *Arabidopsis dwarf1* Mutant is Defective in the Conversion of 24-Methylenecholesterol to Campesterol in Brassinosteroid Biosynthesis," *Plant Physiol.*, 1999, 119:897-907.
Choe et al., "Overexpression of *DWARF4* in the brassinosteroid biosynthetic pathway results in increased vegetative growth and seed yield in *Arabidopsis*," *The Plant Journal*, 2001, 26(6):573-582.

(Continued)

*Primary Examiner* — Vinod Kumar
(74) *Attorney, Agent, or Firm* — Fish & Richardson P.C.

(57) ABSTRACT

Isolated polynucleotides, polypeptides, and transgenic plants are described. The transgenic plants can exhibit one or more altered phenotypic characteristics relative to a control plant, including increased height, increased seed weight, increased photosynthetic rates, decreased levels of campestanol, or increased levels of 6-deoxocathasterone.

25 Claims, 2 Drawing Sheets

OTHER PUBLICATIONS

Choe et al., "The *DWF4* Gene of *Arabidopsis* Encodes a Cytochrome P450 That Mediates Multiple 22α-Hydroxylation Steps in Brassinosteroid Biosynthesis," *The Plant Cell*, 1998, 10:231-243.

Choi et al., "An Alternative Brassinolide Biosynthetic Pathway Via Late C-6 Oxidation," *Phytochemistry*, 1997, 44(4):609-613.

Chory et al., "A Role for Cytokinins in De-Etiolation in *Arabidopsis*," *Plant Physiol.*, 1994, 104:339-347.

Chory et al., "*Arabidopsis thaliana* Mutant That Develops as a Light-Growm Plant in the Absence of Light," *Cell*, 1989, 58:991-999.

Clouse et al., "A Brassinosteroid-Insensitive Mutant in *Arabidopsis thaliana* Exhibits Multiple Defects in Growth and Development," *Plant Physiol.*, 1996, 111:671-678.

Deng and Quail, "Genetic and Phenotype Characterization of *cop 1* Mutants of *Arabidopsis thaliana*," *The Plant Journal*, 1992, 2(1):83-95.

Deng, "Fresh View of Light Signal Transduction in Plants," *Cell*, 1994, 76:423-426.

Feldmann et al., "A Dwarf Mutant of *Arabidopsis* Generated by T-DNA Insertion Mutagenesis," *Science*, 1989, 243:1351-1354.

Feldmann, "Cytochrome P450s as genes for crop improvement," *Current Opinion in Plant Biology*, 2001, 4:162-167.

Finnegan et al., Reduced DNA methylation in *Arabidopsis thaliana* results in abnormal plant development, *Proc. Natl. Acad. Sci. USA*, 1996, 93:8449-8454.

Fujioka and Sakurai, "Biosynthesis and Metabolism of Brassinosteroids," *Physiologia Plantarum*, 1997, 100:710-715.

Fujioka and Sakurai, "Brassinosteroids," *Nat. Prod. Rep.*, 1997, 14:1-10.

Fujioka et al., "Identification of Castasterone, 6-Deoxocastasterone, Typhasterol and 6-Deoxotyphasterol from the Shoots of *Arabidopsis thaliana*," *Plant Cell Physiol.*, 1996, 37(8):1201-1203.

Fujioka et al., "The *Arabidopsis deetiolated2* Mutant is Blocked Early in Brassinosteroid Biosynthesis," *Plant Cell*, 1997, 9:1951-1962.

Fujioka et al., "An early C-22 oxidation branch in the brassinosteroid biosynthetic pathway," *Plant Physiol.*, 2002, 130:930-939.

Gachotte et al., "An *Arabidopsis* mutant deficient in sterol biosynthesis: heterologous complementation by *ERG 3* encoding a Δ7-sterol-C-5-desaturase from yeast," *The Plant Journal*, 1995, 8(3):407-416.

Grove et al., "Brassinolide, a Plant Growth-Promoting Steroid Isolated From *Brassica napus* Pollen," *Nature*, 1979, 281:216-217.

Guatelli et al., "Isothermal, in vitro amplification of nucleic acids by a multienzyme reation modeled after retroviral replication" *Proc. Natl. Acad. Sci. USA*, 1990, 87:1874-1878.

He et al., "BZR1 is a transcriptional repressor with dual roles in brassinosteroid homeostasis and growth responses," *Science*, 2005, 307:1634-1638.

Hong et al., "A rice brassinosteroid-deficient mutant, *ebisu dwarf* (d2), is caused by a loss of function of a new member of cytochrome P450," *Plant Cell*, 2003, 15:2900-2910.

Hou et al., "A New Class of *Arabidopsis* Constitutive Photomorphogenic Genes Involved in Regulating Cotyledon Development," *Plant Cell*, 1993, 5:329-339.

Hwang and Goodman, "An *Arabidopsis thaliana* root-specific kinase homolog is induced by dehydration, ABA, and NaCl" *Plant J.*, 1995, 8:37.

Hyrup et al., "Peptide Nucleic Acids (PNA): Synthesis, Properties and Potential Applications" *Bioorgan. Med. Chem.*, 1996, 4(1):5-23.

Kankel et al., "*Arabidopsis* MET1 Cytosine Methyltransferase Mutants," *Genetics*, 2003, 163:1109-1122.

Kauschmann et al., "Genetic Evidence for an Essential Role of Brassinosteroids in Plant Development," *Plant Journal*, 1996, 9:701-713.

Kim et al., "A 20 nucleotide upstream element is essential for the nopaline synthase (nos) promoter activity," *Plant Molecular Biology*, 1994, 24:105-117.

Koornneef and Van der Veen, "Induction and Analysis of Gibberellin Sensitive Mutants in *Arabidopsis thaliana* (L.) Heynh," *Theor. Appl. Genet.*, 1980, 58:257-263.

Koornneef et al., "A Gibberellin Insensitive Mutant of *Arabidopsis thaliana*," *Physiol. Plant*, 1985, 65:33-39.

Lewis, *Genetic Engineering News*, 1992, 12:1.

Li and Chory, "A Putative Leucine-Rich Repeat Receptor Kinase Involved in Brassinosteroid Signal Transduction," *Cell*, 1997, 90:929-938.

Li et al., "A Role for Brassinosteroids in Light-Dependent Development of *Arabidopsis*," *Science*, 1996, 272:398-401.

Li et al., "Conservation Function Between Mammalian and Plant Steroid 5α-Reductases," *Proc. Natl. Acad. Sci. USA*, 1997, 94:3554-3559.

Mandava, "Plant Growth-Promoting Brassinosteroids," *Annu. Rev. Plant Physiol. Plant Mol. Biol.*, 1988, 39:23-52.

Mitchell et al., "Brassins-a New Family of Plant Hormones from Rape Pollen," *Nature*, 1970, 225:1065-1066.

Mushegian and Koonin, "A Putative FAD-Binding Domain in a Distinct Group of Oxidases Including a Protein Involved in Plant Development," *Protein Science*, 1995, 4:1243-1244.

Nebert et al., "Corrigendum The P450 Superfamily: Update on New Sequences, Gene Mapping, and Recommended Nomenclature," *DNA and Cell Biology*, 1991, 10(5):397-398.

Nebert et al., "P450 Gene Nomenclature Based on Evolution," *Methods Enzymol.*, 1991, 206:3-11.

Nebert et al., "The P450 Superfamily: Update on New Sequences, Gene Mapping, and Recommended Nomenclature," *DNA and Cell Biology*, 1991a, 10(1):1-14.

Nelson et al., "P450 superfamily: update on new sequences, gene mapping, accession Nos. and nomenclature," *Pharmacogenetics*, 1996, 6(1):1-42.

Noguchi et al., "Biosynthetic Pathways of Brassinolide in *Arabidopsis*," *Plant Physiology*, 2000, 124:201-209.

Nomura et al., "Blockage of Brassinosteroid Biosynthesis and Sensitivity Causes Dwarfism in Garden Pea," *Plant Physiol.*, 1997, 113:31-37.

Rees, "Biosynthesis of Ecdysone," *Comprehensive Insect Physiology, Biochemistry and Pharmacology*, 1985, Kerkut and Gilbert (eds.), Oxford, Pergamon Press, pp. 249-293.

Ronemus et al., "Demethylation-Induced Developmental Pleiotropy in *Arabidopsis*," *Science*, 1996, 273:654-656.

Sakurai and Fujioka, "Studies on Biosynthesis of Brassinosteroids," *Biosci. Biotechnol. Biochem.*, 1997, 61:757-762.

Stam et al,. "The Silence of Genes in Transgenic Plants," *Annals of Botany*, 1997, 79:3-12.

Summerton and Weller, "Morpholino Antisense Oligomer: Design, Preparation, and Properties" *Antisense Nucleic Acid Drug Dev.*, 1997, 7(3):187-195.

Szekeres et al., "Brassinosteroids Rescue the Deficiency of CYP90, a Cytochrome P450, Controlling Cell Elongation and De-etiolation in *Arabidopsis*," *Cell*, 1996, 85:171-182.

Takahashi et al., "The DIMINUTO Gene of *Arabidopsis* is Involved in Regulating Cell Elongation," *Genes & Development*, 1995, 9:97-107.

Talon et al., "Endogenous Gibberellins in *Arabidopsis thaliana* and Possible Steps Blocked in the Biosynthetic Pathways of the Semidwarf *ga4* and *ga5* Mutants," *Proc. Natl. Acad. Sci. USA*, 1990, 87:7983-7987.

Tanabe et al., "A novel cytochrome P450 is implicated in brassinosteroid biosynthesis via the characterization of a rice dwarf mutant, *dwart11*, with reduced seed length," *Plant Cell*, 2005, 17:776-790.

Timpte et al., "Effects of the *axr2* Mutation of *Arabidopsis* on Cell Shape in Hypocotyl and Inflorescence," *Planta*, 1992, 188:271-278.

Timpte et al., "The *axr2-1* Mutation of *Arabidopsis thaliana* is a Gain-of-Function Mutation that Disrupts an Early Step in Auxin Response," *Genetics*, 1994, 138:1239-1249.

van der Krol et al., "Antisense genes in plants: an overview," *Gene*, 1988, 72:45-50.

Vinkenoog et al., "Hypomethylation Promotes Autonomous Endosperm Development and Rescues Postfertilization Lethality in *fie* Mutants," *The Plant Cell*, 2000, 12:2271-2282.

Waycott et al., "Phenotypic Characterization of the *dwarf-4* Mutant of Lettuce," *Can. J. Bot.*, 1994, 72:1541-1549.

Wei and Deng, "*COP9*: A New Genetic Locus Involved in Light-Regulated Development and Gene Expression in *Arabidopsis*," *Plant Cell*, 1992, 4:1507-1518.

Wei et al., "*Arabidopsis COP8, COP10*, and *COP11* Genes are Involved in Repression of Photomorphogenic Development in Darkness," *Plant Cell*, 1994, 6:629-643.

Weiss, "Hot Prospect for New Gene Amplifier," *Science*, 1991, 254:1292-1293.

Yokata, "The Structure, Biosynthesis and Function of Brassinosteroids," *Trends Plant Sci.*, 1997, 2(4):137-143.

Chapple, "Molecular-Genetic Analysis of Plant Cytochrome P450-Dependent Monooxygenases," *Annu. Rev. Plant Physiol. Plant Mol. Biol.*, 1998, 49:311-43.

Nelson, "Cytochrome P450 Nomenclature," *Methods in Molecular Biology*, 1998, 107:15-24.

Ashikari et al., Cytokinin oxidase regulates rice grain production, *Science*, 2005, 309: 741-745.

Benjamini and Hochberg, "Controlling the false discovery rate: A practical and powerful approach to multiple testing," *J. R. Stat. Soc.*, 1995, 57: 289-300.

Boisnard-Lorig et al., "Dynamic analyses of the expression of the HISTONE::YFP fusion protein in *Arabidopsis* show that syncytial endosperm is divided in mitotic domains," *Plant Cell*, 2001, 13:495-509.

Bouvier-Nave et al., "Two families of sterol methyltransferases are involved in the first and the second methylation steps of plant sterol biosynthesis," *Eur. J. Biochem*, 1998, 256: 88-96.

Buerkle et al., "The H+-sucrose cotransporter NtSUT1 is essential for sugar export from tobacco leaves," *Plant Physiol.*, 1998, 118: 59-68.

Dhaubhadel et al., "Brassinosteroid functions to protect the translational machinery and heat-shock protein synthesis following thermal stress," *Plant J.*, 2002, 29(6): 681-691.

Fritzius et al., "Induction of *ApL3* expression by trehalose complements the starch-deficient *Aribidopsis* mutant *adg2-1* lacking ApL1, the large subunit of ADP-glucose pyrophosphorylase," *Plant Physiol.*, 2001, 126: 883-889.

Fujii et al., "Growth-regulating action of brassinolide in rice plants," In Brassinosteroids: Chemistry, Bioactivity, and Applications (Washington DC, American Chemical Society, 1991), 306-311.

Garcia-Lorenzo et al., "Degradation of the main photosystem II light-harvesting complex," *Photochem. Photobiol. Sci.*, 2005, 4: 1065-1071.

Hiei et al., "Efficient transformation of rice (*Oryza sativa L.*) mediated by *Agrobacterium* and sequence analysis of the boundaries of the T-DNA," *The Plant J.*, 1994, 6 (2): 271-282.

Hong et al., "The rice *brassinosteroid-deficient dwarf 2* mutant, defective in the rice homolog of *Arabidopsis* DIMINUTO/DWARF1, is rescued by the endogenously accumulated alternative bioactive brassinosteroid, dolichosterone," *The Plant Cell*, 2005, 17: 2243-2254.

Horton, "Prospects for crop improvement through the genetic manipulation of photosynthesis: morphological and biochemical aspects of light capture," *J. Exp. Bot.*, 2000, 51: 475-785.

Johansson et al., "Molecular cloning and characterization of cDNA encoding poplar UDP-glucose dehydrogenase, a key gene of hemicellulose/pectin formation," *Biochem. Biophys. Acta*, 2002, 1573: 53-58.

Johnson, et al., "Spatial control of transgene expression in rice (*Oryza sativa L.*) using the GAL4 enhancer trapping system," *The Plant J.* 2005, 41: 779-789.

Kleczkowski et al., "UDP-glucose pyrophosphorylase. An old protein with new tricks," *Plant Physiol.*, 2004, 134: 912-918.

Knoester et al., "Ethylene-insensitive tobacco lacks nonhost resistance against soil-borne fungi," *Proc. Natl. Acad. Sci., USA*, 1998, 95: 1933-1937.

Kolbe et al., Trehalose 6-phosphate regulates starch synthesis via posttranslational redox activation of ADP-glucose pyrophosphorylase, *Proc. Natl. Acad. Sci.*, 2005, 102 (31): 11118-11123.

Laplaze et al., "GAL4-GFP enhancer trap lines for genetic manipulation of lateral root development in *Arabidopsis thaliana*," *J. Exp. Bot.*, 2005, 56 (419): 2433-2442.

Li et al., "Control of tillering in rice," *Nature* 2003, 422: 618-621.

Livak and Schmittgen, "Analysis of relative gene expression data using real-time quantitative PCR and the $2^{-\Delta\Delta C_T}$ method," *Methods* 2001, 25: 402-408.

Misson et al., "A genome-wide transcriptional analysis using *Arabidopsis thaliana* Affymetrix gene chips determined plant responses to phosphate deprivation," *Proc. Natl. Acad. Sci.*, 2005, 102 (33):11934-11939.

Muessig et al., "Brassinosteroid-regulated gene expression," *Plant Physiol.*, 2002, 129: 1241-1251.

Nam et al., "BRI1/BAK1, a receptor kinase pair mediating brassinosteroid signaling," *Cell*, 2002, 110: 203-212.

Nemhauser et al., "Interdependency of brassinosteroid and auxin signaling in *Arabidopsis*," *PLoS Biology*, 2004, 2(9): 1460-1471.

Noguchi et al., "Brassinosteroid-insensitive dwarf mutants of *Arabidopsis* accumulate brassinosteroids," *Plant Physiol.*, 1999, 121: 743-752.

Ramraj et al., "Effects of 28-homobrassinolide on yields of wheat, rice, groundnut, mustard, potato and cotton," *J. Agric. Sci.*, 1997, 128: 405-413.

Sakamoto and Matsuoka, "Generating high-yielding varieties by genetic manipulation of plant architecture," *Curr. Opin. Biotechnol.*, 2004, 15: 144-147.

Sakamoto et al., "Erect leaves caused by brassinosteroid deficiency increase biomass production and grain yield in rice," *Nat. Biotechnol.*, 2006, 24 (1): 105-109.

Sasaki et al., "Green revolution: A mutant gibberellin-synthesis gene in rice," *Nature* 2002, 416:701-702.

Satoh et al., "Starch-branching enzyme I-deficient mutation specifically affects the structure and properties of starch in rice endosperm," *Plant Physiol.*, 2003, 133: 1111-1121.

Shimada et al., "Brassinosteroid-6-oxidases from *Arabidopsis* and tomato catalyze multiple C-6 oxidations in brassinosteroid biosynthesis," *Plant Physiol.*, 2001, 126: 770-779.

Smart et al., "Delayed leaf senescence in tobacco plants transformed with *tmr*, a gene for cytokinin production in *Agrobacterium*," *Plant Cell*, 1991, 3: 647-656.

Smidansky et al., "Enhanced ADP-glucose pyrophosphorylase activity in wheat endosperm increases seed yield," *Proc. Natl. Acad. Sci.*, 2002, 99(3): 1724-1729.

Smith and Nelson, "Relationship between seed-filling period and yield among soybean broadening lines," *Crop Sci.*, 1986, 26: 469-472.

Smyth et al., "Use of within-array replicate spots for assessing differential expression in microarray experiments," *Bioinformatics*, 2005, 21(9): 2067-2075.

Symons and Reid, "Brassinosteroids do not undergo long-distance transport in pea. Implications for the regulation of endogenous brassinosteroid levels," *Plant Physiol.*, 2004, 135: 2196-2206.

Takeda et al., "The *OsTB1* gene negatively regulates lateral branching in rice," *Plant J.*, 2003, 33:513-5200

Wang et al., "Structure, expression and promoter activity of two polyubiquitin genes from rice (*Oryza sativa L.*)," *Plant Sci.*, 2000, 156: 201-211.

Wang et al., "Micro-array analysis of the nitrate response in *Arabidopsis* roots and shoots reveals over 1,000 rapidly responding genes and new linkages to glucose, trehalose-6-phosphate, iron, and sulfate metabolism," *Plant Physiol.*, 2003, 132: 556-567.

Wingler et al., "Trehalose induces the ADP-glucose pyrophosphorylase gene, *ApL3*, and starch synthesis in *Arabidopsis*," *Plant Physiol.*, 2000, 124: 105-114.

Wood et al., "The *Arabidopsis thaliana* vernalization response requires a polycomb-like protein complex that also includes Vernalization Insensitive 3," *Proc. Natl Acad. Sci*, 2006, 103(39): 1431-14636.

Wu et al., "Promoters of rice seed storage protein genes direct endosperm-specific gene expression in transgenic rice," *Plant Cell Physiol.*, 1998, 39(8): 885-889.

Xu et al., "Expression of the rice *Osgrp1* promoter-*Gus* reporter gene is specifically associated with cell elongation/expansion and differentiation," *Plant Mol. Biol.* 1995, 28: 455-471.

Yokota et al., "Transport and metabolism of brassinosteroids in rice," *In Progress in Plant Growth Regulation*, (Dordrecht, The Netherlands: Kluwer, 1992), 298-305.

Yu et al., "A role for brassinosteroids in the regulation of photosynthesis in *Cucumis sativus*," *J. Exp. Bot.*, 2004, 55(399): 1135-1143.

Zhang and Guarente, "The yeast activator HAP1—a GAL4 family member—binds DNA in a directly repeated orientation," *Genes& Dev.*, 1994, 8: 2110-2119.

Zou et al., "Characterizations and fine mapping of a mutant gene for high tillering and dwarf in rice (*Oryza sativa L*)," *Planta* 2005, 222: 604-612.

International Search Report and Written Opinion for Corresponding PCT Application No. PCT/US2005/013706, mailed Mar. 21, 2006, (15 Pages).

International Preliminary Report on Patentability for Corresponding PCT Application No. PCT/US2005/013706, mailed Nov. 2, 2006, (8 Pages).

* cited by examiner

FIG. 1

```
M(F,M)(E,M)<1>(E,G)<1>H(T,V)L(L,A)<1>L<0-
2>(L,R)(L,A)(L,W)(P,A)SLLtLaL(F,N)(L,H)(I,F)L(L,P)(K,L)(R,L)(R,L)N<1>
+<1-
5>P(P,R)G<2>GWP(F,L)aGET<1>(G,R)rL<1>(P,A)(Y,H)<1>t(T,N)taG<1>Fa(Q,E)
(Q,D)H<1>t+YG+ar+S<1>LF(G,C)(E,T)(P,R)TaVS(A,C)D(A,Q)(G,D)LN+rILQNE(G
,E)RLF(E,Q)CSYPR(S,P)I(G,H)GILGK(W,S)SMLVaaGn<1>H+<1>aR<1>atL(N,A)(F,
L)at(H,S)<1>+L+<2>(L,Y)L<1>naE+(H,I)tL<1>Va<1>tW<3>t<1-
7>(F,V)t(A,F)(Q,C)<1>(E,Q)A+KFtF(N,S)aa(A,V)K<1>aata(D,S)P(G,E)E(E,P)
(E,V)T(E,A)(Q,R)a<2>nratFMKGaaS(A,F)PL(N,Y)aPGT(A,P)Y<1>KAa<1>tR(A,E)
<1>I(L,S)<2>a(E,K)(R,G)(K,I)a(E,K)ER<1-
34>(D,G)D(L,F)L(G,D)(W,V)<1>L(K,S)<1>(S,N)(N,E)LS<1>E(Q,E)(I,K)a(D,S)
(L,F)aL(S,D)(L,S)L(F,L)tG(H,Y)ETtSa(A,L)ata(A,V)arFL<2>(C,S)(P,A)(K,Q
)(A,D)a<1>(E,L)a+(E,R)EH(L,D)<1>I(A,R)(R,S)<1>(K,Q)<2-
4>E<2>L<1>(W,S)nDYK(K,E)M<1>rTQ(C,Q)VINEtLR(L,C)GNaV+FaHRK(A,V)aKDV+Y
K(G,E)Y(D,L)IPSGWKaLPV<1>tAVHL(D,N)<1>S(R,L)(Y,H)<1>(Q,D)(P,A)p<1>FpP
(W,C)RW<3-21>r(M,T)PrGGG(P,T)RLC(A,P)GSELAKaE(M,T)A(V,F)FaHHLV
```

SEQUENCE LISTING

<160> NUMBER OF SEQ ID NOS: 41

<210> SEQ ID NO 1
<211> LENGTH: 513
<212> TYPE: PRT
<213> ORGANISM: Arabidopsis
<220> FEATURE:
<221> NAME/KEY: misc_feature
<222> LOCATION: (1)..(513)
<223> OTHER INFORMATION: Arabidopsis DWF4
<220> FEATURE:
<221> NAME/KEY: misc_feature
<222> LOCATION: (40)..(90)
<223> OTHER INFORMATION: Pfam Name: p450; Pfam Description: Cytochrome P450

<400> SEQUENCE: 1

```
Met Phe Glu Thr Glu His His Thr Leu Leu Pro Leu Leu Leu Pro
1               5                   10                  15

Ser Leu Leu Ser Leu Leu Leu Phe Leu Ile Leu Leu Lys Arg Arg Asn
            20                  25                  30

Arg Lys Thr Arg Phe Asn Leu Pro Pro Gly Lys Ser Gly Trp Pro Phe
        35                  40                  45

Leu Gly Glu Thr Ile Gly Tyr Leu Lys Pro Tyr Thr Ala Thr Thr Leu
    50                  55                  60

Gly Asp Phe Met Gln Gln His Val Ser Lys Tyr Gly Lys Ile Tyr Arg
65                  70                  75                  80

Ser Asn Leu Phe Gly Glu Pro Thr Ile Val Ser Ala Asp Ala Gly Leu
                85                  90                  95

Asn Arg Phe Ile Leu Gln Asn Glu Gly Arg Leu Phe Glu Cys Ser Tyr
            100                 105                 110

Pro Arg Ser Ile Gly Gly Ile Leu Gly Lys Trp Ser Met Leu Val Leu
        115                 120                 125

Val Gly Asp Met His Arg Asp Met Arg Ser Ile Ser Leu Asn Phe Leu
    130                 135                 140

Ser His Ala Arg Leu Arg Thr Ile Leu Leu Lys Asp Val Glu Arg His
145                 150                 155                 160

Thr Leu Phe Val Leu Asp Ser Trp Gln Gln Asn Ser Ile Phe Ser Ala
                165                 170                 175

Gln Asp Glu Ala Lys Lys Phe Thr Phe Asn Leu Met Ala Lys His Ile
            180                 185                 190

Met Ser Met Asp Pro Gly Glu Glu Thr Glu Gln Leu Lys Lys Glu
        195                 200                 205

Tyr Val Thr Phe Met Lys Gly Val Val Ser Ala Pro Leu Asn Leu Pro
    210                 215                 220

Gly Thr Ala Tyr His Lys Ala Leu Gln Ser Arg Ala Thr Ile Leu Lys
225                 230                 235                 240

Phe Ile Glu Arg Lys Met Glu Arg Lys Leu Asp Ile Lys Glu Glu
                245                 250                 255

Asp Gln Glu Glu Glu Glu Val Lys Thr Glu Asp Glu Ala Glu Met Ser
            260                 265                 270

Lys Ser Asp His Val Arg Lys Gln Arg Thr Asp Asp Leu Leu Gly
        275                 280                 285

Trp Val Leu Lys His Ser Asn Leu Ser Thr Glu Gln Ile Leu Asp Leu
    290                 295                 300

Ile Leu Ser Leu Leu Phe Ala Gly His Glu Thr Ser Ser Val Ala Ile
305                 310                 315                 320
```

```
Ala Leu Ala Ile Phe Phe Leu Gln Ala Cys Pro Lys Ala Val Glu Glu
                325                 330                 335

Leu Arg Glu Glu His Leu Glu Ile Ala Arg Ala Lys Lys Glu Leu Gly
            340                 345                 350

Glu Ser Glu Leu Asn Trp Asp Asp Tyr Lys Lys Met Asp Phe Thr Gln
        355                 360                 365

Cys Val Ile Asn Glu Thr Leu Arg Leu Gly Asn Val Val Arg Phe Leu
    370                 375                 380

His Arg Lys Ala Leu Lys Asp Val Arg Tyr Lys Gly Tyr Asp Ile Pro
385                 390                 395                 400

Ser Gly Trp Lys Val Leu Pro Val Ile Ser Ala Val His Leu Asp Asn
                405                 410                 415

Ser Arg Tyr Asp Gln Pro Asn Leu Phe Asn Pro Trp Arg Trp Gln Gln
            420                 425                 430

Gln Asn Asn Gly Ala Ser Ser Gly Ser Gly Ser Phe Ser Thr Trp
        435                 440                 445

Gly Asn Asn Tyr Met Pro Phe Gly Gly Pro Arg Leu Cys Ala Gly
    450                 455                 460

Ser Glu Leu Ala Lys Leu Glu Met Ala Val Phe Ile His His Leu Val
465                 470                 475                 480

Leu Lys Phe Asn Trp Glu Leu Ala Glu Asp Asp Lys Pro Phe Ala Phe
                485                 490                 495

Pro Phe Val Asp Phe Pro Asn Gly Leu Pro Ile Arg Val Ser Arg Ile
            500                 505                 510

Leu

<210> SEQ ID NO 2
<211> LENGTH: 485
<212> TYPE: PRT
<213> ORGANISM: Zea mays
<220> FEATURE:
<221> NAME/KEY: misc_feature
<222> LOCATION: (1)..(485)
<223> OTHER INFORMATION: Ceres CLONE ID no. 234510

<400> SEQUENCE: 2

Met Met Met Met Met Met Ala Gly Glu His Val Leu Ala Ala Leu Gly
1               5                   10                  15

Thr Leu Leu Leu Ala Ser Leu Leu Thr Leu Val Leu Asn His Phe Leu
            20                  25                  30

Pro Leu Leu Leu Asn Pro Lys Ala Pro Arg Gly Ser Phe Gly Trp Pro
        35                  40                  45

Leu Leu Gly Glu Thr Leu Arg Phe Leu Thr Pro His Ala Ser Asn Thr
    50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
                85                  90                  95

Leu Asn His Phe Ile Leu Gln Asn Glu Glu Arg Leu Phe Gln Cys Ser
            100                 105                 110

Tyr Pro Arg Pro Ile His Gly Ile Leu Gly Lys Ser Ser Met Leu Val
        115                 120                 125

Val Leu Gly Glu Asp His Lys Arg Leu Arg Asn Leu Ala Leu Ala Leu
    130                 135                 140

Val Thr Ser Thr Lys Leu Lys Pro Ser Tyr Leu Gly Asp Ile Glu Lys
145                 150                 155                 160
```

Ile Ala Leu His Val Gly Ala Trp Arg Arg His Gly Ser Ser Gly
            165                 170                 175

Gly Val Arg Val Val Ala Phe Cys Glu Glu Ala Arg Lys Phe Ala Phe
        180                 185                 190

Ser Val Ile Val Lys Gln Val Leu Gly Leu Ser Pro Glu Pro Val
    195                 200                 205

Thr Ala Arg Ile Leu Glu Asp Phe Leu Ala Phe Met Lys Gly Leu Ile
210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
                245                 250                 255

Arg Ser Ala Gly Ser Trp Asn Lys Gln Gly Asp Phe Leu Asp Val Leu
            260                 265                 270

Leu Ser Ser Asn Glu Leu Ser Asp Glu Glu Lys Val Ser Phe Val Leu
        275                 280                 285

Asp Ser Leu Leu Gly Gly Tyr Glu Thr Thr Ser Leu Leu Ile Ser Met
    290                 295                 300

Val Val Tyr Phe Leu Gly Gln Ser Ala Gln Asp Leu Asp Leu Val Lys
305                 310                 315                 320

Arg Glu His Asp Ser Ile Arg Ser Asn Lys Gly Lys Glu Glu Cys Leu
                325                 330                 335

Thr Ser Glu Asp Tyr Lys Lys Met Glu Tyr Thr Gln Gln Val Ile Asn
            340                 345                 350

Glu Ala Leu Arg Cys Gly Asn Ile Val Lys Phe Val His Arg Lys Ala
        355                 360                 365

Leu Lys Asp Val Lys Tyr Lys Gly Tyr Leu Ile Pro Ser Gly Trp Lys
    370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
                405                 410                 415

Thr Ser Lys Arg Phe Thr Pro Phe Gly Gly Pro Arg Leu Cys Pro
            420                 425                 430

Gly Ser Glu Leu Ala Lys Val Glu Thr Ala Phe Phe Leu His His Leu
        435                 440                 445

Val Leu Asn Tyr Arg Trp Arg Ile Asp Gly Asp Asp Ile Pro Met Ala
    450                 455                 460

Tyr Pro Tyr Val Glu Phe Gln Arg Gly Leu Pro Ile Glu Ile Glu Pro
465                 470                 475                 480

Thr Ser Pro Glu Ser
                485

```
<210> SEQ ID NO 3
<211> LENGTH: 502
<212> TYPE: PRT
<213> ORGANISM: Zea mays
<220> FEATURE:
<221> NAME/KEY: misc_feature
<222> LOCATION: (1)..(502)
<223> OTHER INFORMATION: Public GI no. 24421687

<400> SEQUENCE: 3
```

Met Ala Ser Ile Thr Ser Glu Leu Leu Phe Phe Leu Pro Phe Ile Leu
1               5                   10                  15

Leu Ala Leu Leu Thr Phe Tyr Thr Thr Thr Val Ala Lys Cys His Gly

-continued

```
            20                  25                  30
Gly His Trp Trp Arg Gly Gly Thr Thr Pro Ala Lys Arg Lys Arg Met
        35                  40                  45
Asn Leu Pro Pro Gly Ala Ala Gly Trp Pro Leu Val Gly Glu Thr Phe
 50                  55                  60
Gly Tyr Leu Arg Ala His Pro Ala Thr Ser Val Gly Arg Phe Met Glu
 65                  70                  75                  80
Gln His Ile Ala Arg Tyr Gly Lys Ile Tyr Arg Ser Ser Leu Phe Gly
                85                  90                  95
Glu Arg Thr Val Val Ser Ala Asp Ala Gly Leu Asn Arg Tyr Ile Leu
                100                 105                 110
Gln Asn Glu Gly Arg Leu Phe Glu Cys Ser Tyr Pro Arg Ser Ile Gly
            115                 120                 125
Gly Ile Leu Gly Lys Trp Ser Met Leu Val Leu Val Gly Asp Pro His
            130                 135                 140
Arg Glu Met Arg Ala Ile Ser Leu Asn Phe Leu Ser Ser Val Arg Leu
145                 150                 155                 160
Arg Ala Val Leu Leu Pro Glu Val Glu Arg His Thr Leu Leu Val Leu
                165                 170                 175
Arg Ala Trp Pro Pro Ser Ser Thr Phe Ser Ala Gln His Gln Ala Lys
            180                 185                 190
Lys Phe Thr Phe Asn Leu Met Ala Lys Asn Ile Met Ser Met Asp Pro
            195                 200                 205
Gly Glu Glu Glu Thr Glu Arg Leu Arg Arg Glu Tyr Ile Thr Phe Met
        210                 215                 220
Lys Gly Val Val Ser Ala Pro Leu Asn Leu Pro Gly Thr Pro Tyr Trp
225                 230                 235                 240
Lys Ala Leu Lys Ser Arg Ala Ala Ile Leu Gly Val Ile Glu Arg Lys
                245                 250                 255
Met Glu Glu Arg Val Glu Lys Leu Ser Lys Glu Asp Ala Ser Val Glu
                260                 265                 270
Gln Asp Asp Leu Leu Gly Trp Ala Leu Lys Gln Ser Asn Leu Ser Lys
            275                 280                 285
Glu Gln Ile Leu Asp Leu Leu Leu Ser Leu Leu Phe Ala Gly His Glu
            290                 295                 300
Thr Ser Ser Met Ala Leu Ala Leu Ala Ile Phe Phe Leu Glu Gly Cys
305                 310                 315                 320
Pro Lys Ala Val Gln Glu Leu Arg Glu Glu His Leu Gly Ile Ala Arg
                325                 330                 335
Arg Gln Arg Leu Arg Gly Glu Cys Lys Leu Ser Trp Glu Asp Tyr Lys
            340                 345                 350
Glu Met Val Phe Thr Gln Cys Val Ile Asn Glu Thr Leu Arg Leu Gly
            355                 360                 365
Asn Val Val Arg Phe Leu His Arg Lys Val Ile Lys Asp Val His Tyr
        370                 375                 380
Lys Gly Tyr Asp Ile Pro Ser Gly Trp Lys Ile Leu Pro Val Leu Ala
385                 390                 395                 400
Ala Val His Leu Asp Ser Ser Leu Tyr Glu Asp Pro Gln Arg Phe Asn
                405                 410                 415
Pro Trp Arg Trp Lys Ser Ser Gly Ser Gly Leu Ala Gln Ser
            420                 425                 430
Ser Ser Phe Met Pro Tyr Gly Gly Gly Thr Arg Leu Cys Ala Gly Ser
            435                 440                 445
```

```
Glu Leu Ala Lys Leu Glu Met Ala Val Phe Leu His His Leu Val Leu
450                 455                 460
Asn Phe Arg Trp Glu Leu Ala Glu Pro Asp Gln Ala Phe Val Phe Pro
465                 470                 475                 480
Phe Val Asp Phe Pro Lys Gly Leu Pro Ile Arg Val His Arg Ile Ala
                485                 490                 495
Gln Asp Asp Glu Gln Glu
            500
```

<210> SEQ ID NO 4
<211> LENGTH: 1035
<212> TYPE: DNA
<213> ORGANISM: Arabidopsis thaliana
<220> FEATURE:
<221> NAME/KEY: misc_feature
<222> LOCATION: (1)..(1035)
<223> OTHER INFORMATION: >DWF4 antisense
<220> FEATURE:
<221> NAME/KEY: CDS
<222> LOCATION: (1)..(1035)
<223> OTHER INFORMATION: Referenced by SEQ ID NO: 1

<400> SEQUENCE: 4

```
atgttcgaaa cagagcatca tactctctta cctcttcttc ttctcccatc gcttttgtct      60
cttcttctct tcttgattct cttgaagaga agaaatagaa aaaccagatt caatctacct     120
ccgggtaaat ccggttggcc atttcttggt gaaaccatcg gttatcttaa accgtacacc     180
gccacaacac tcggtgactt catgcaacaa catgtctcca atatggtaag atatatagat     240
cgaacttgtt tggagaacca acgatcgtat cagctgatgc tggacttaat agattcatat     300
tacaaaacga aggaaggctc tttgaatgta gttatcctag aagtataggt gggattcttg     360
ggaaatggtc gatgcttgtt cttgttggtg acatgcatag agatatgaga agtatctcgc     420
ttaacttctt aagtcacgca cgtcttagaa ctattctact taaagatgtt gagagacata     480
cttttgtttgt tcttgattct tggcaacaaa actctatttt ctctgctcaa gacgaggcca     540
aaaagttacg tttaatctaa tggcgaagca tataatgagt atggatcctg agaagaaga      600
aacagagcaa ttaaagaaag agtatgtaac tttcatgaaa ggagttgtct ctgctcctct     660
aaatctacca ggaactgctt atcataaagc tcttcaggtc acgagcaacg atattgaagt     720
tcattgagag gaaatggaa gagagaaaat tggatatcaa ggaagaagat caagaagaag      780
aagaagtgaa aacagaggat gaagcagaga tgagtaagag tgatcatgtt aggaaacaaa     840
gaacagacga tgatcttttg ggatgggttt tgaaacattc gaattatcg acggagcaaa      900
ttctcgatct cattcttagt ttgttatttg ccggacatga gacttcttct gtagccattg     960
ctcaagagca tcttgagatc gcgagggcca agaaggaact aggagagtca gaattaaatt    1020
gggatgatta caaga                                                     1035
```

<210> SEQ ID NO 5
<211> LENGTH: 1019
<212> TYPE: DNA
<213> ORGANISM: Arabidopsis thaliana
<220> FEATURE:
<221> NAME/KEY: misc_feature
<222> LOCATION: (1)..(1019)
<223> OTHER INFORMATION: Ceres Promoter YP0144
<220> FEATURE:
<221> NAME/KEY: misc_feature
<222> LOCATION: (1)..(1019)
<223> OTHER INFORMATION: Columbia ecotype

<400> SEQUENCE: 5

-continued

| | |
|---|---|
| agtcgattgg aaacgttgca agattattga ttgtgagaag agtgctcaag gtagtactga | 60 |
| tttctgtaaa gctcacggtg gtgggaaacg atgttcttgg ggagatggga aatgtgagaa | 120 |
| atttgctaga ggaaagagcg gtttatgcgc tgcgcataac actattatgt ctcgggagaa | 180 |
| caaagatgga agcaagagcg gtttgattgg accgggactc tttagtggcc ttgttttgg | 240 |
| ctctacttct gatcattctc agtctggagc tagcgctgtc tctgattgta ctgattctgt | 300 |
| tgaacgaata cagtttgaga ataggcagaa gaacaagaag atgatgatac cgatgcaggt | 360 |
| tctagtacct tcatcaatga aatctccaag taattcacat gaaggagaaa caaacatcta | 420 |
| tgacttcatg gttccggagg agagagttca cggcggtggg ctagtaatgt ctttacttgg | 480 |
| tggctccatt gatcgaaact gaaagccatt tatggtaaaa gtgtcacatt ctcagcaaaa | 540 |
| acctgtgtaa agctgtaaaa tgtgtgggaa tctccgaatc tgtttgtagc cggttacgtt | 600 |
| atgctggatc aaaaactcaa gatttgttgg atattgttat gctggatcgg tggtgaaacc | 660 |
| acttcccggt tgctaaataa ataaacgttt tgttttata atcttttca ctaaacggca | 720 |
| gtatgggcct ttagtgggct tcctttaagc gaccaataca atcgtcgcac cggaatctac | 780 |
| taccatttat aggtttattc atgtaaaacc tcggaaaatt tgagagccac aacggtcaag | 840 |
| agacaaaaac aacttgaaga taagggata aggaaggctt cctacatgat ggacaacatt | 900 |
| tctttccaca caaattctca taataaaaat cttataatac aaatacttac gtcataatca | 960 |
| ttcaatctag tccccatgtt ttaaggtcct gtttcttgtc tgatacaaac cattgcact | 1019 |

```
<210> SEQ ID NO 6
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0144
<220> FEATURE:
<221> NAME/KEY: misc_feature
<222> LOCATION: (1)..(1003)
<223> OTHER INFORMATION: Wassilewskija ecotype

<400> SEQUENCE: 6
```

| | |
|---|---|
| aaacgttgca agattattga ttgtgagaaa gagtgctcaa ggtagtactg atttctgtaa | 60 |
| agctcacggt ggtgggaaac gatgttcttg gggagatggg aaatgtgaga aatttgcta | 120 |
| gaggaaagaa gcggtttatg cgctgcgcat aacactatta tgtctcggga gaacaaagat | 180 |
| ggaagcaaga gcggtttgat tggaccggga ctctttagtg gccttgtttt tggctctact | 240 |
| tctgatcatt ctcagtctgg agctagcgct gtctctgatt gtactgattc tgttgaacga | 300 |
| atacagtttg agaataggca gaagaacaag aagatgatga taccgatgca ggttctagta | 360 |
| ccttcatcaa tgaaatctcc aagtaattca catgaaggag aaacaaacat ctatgacttc | 420 |
| atggttccgg aggagagagt tcacggcggt gggctagtaa tgtctttact tggtggctcc | 480 |
| attgatcgaa actgaaagcc atttatggta aaagtgtcac attctcagca aaaacctgtg | 540 |
| taaagctgta aaatgtgtgg gaatctccga atctgtttgt agccggttac gttatgctgg | 600 |
| atcaaaaact caagatttgt tggatattgt tatgctggat cggtggtgaa accacttccc | 660 |
| ggttgctaaa taaatacacg ttttgttttt ataatctttt tcactaaacg gcagtatggg | 720 |
| cctttagtgg gcttccttta agcgaccaat acaatcgtcg caccggaatc tactaccatt | 780 |
| tataggttta ttcatgtaaa acctcggaaa atttgagagc cacaacggtc aagagacaaa | 840 |
| aacaacttga agataaaggg ataaggaagg cttcctacat gatggacaac atttctttcc | 900 |

| acacaaattc tcataataaa aatcttataa tacaaatact tacgtcataa tcattcaatc | 960 |
| tagtccccat gttttaaggt cctgtttctt gtctgataca aat | 1003 |

<210> SEQ ID NO 7
<211> LENGTH: 1144
<212> TYPE: DNA
<213> ORGANISM: Arabidopsis thaliana
<220> FEATURE:
<221> NAME/KEY: misc_feature
<222> LOCATION: (1)..(1144)
<223> OTHER INFORMATION: Ceres Promoter YP0190
<220> FEATURE:
<221> NAME/KEY: misc_feature
<222> LOCATION: (1)..(1144)
<223> OTHER INFORMATION: Columbia ecotype

<400> SEQUENCE: 7

| agtcgattgg gattgttggg gcatgtgtga tgcgtttaac gattctaaca gtatatgaaa | 60 |
| ttatatttt tggtcttgtt atttgtctaa aaacctatat ttttctcgta agaatattgt | 120 |
| aagagttatt tttcgaaaat ttaaataatg attcgatcaa cacttttct cattttatca | 180 |
| aaccccttg attgaataga ccgctaaaac aatttgcttg attggtcttt cttacaacga | 240 |
| ctaagttaca aatgtgactg aaagttaccg atcaaaccca tgaaaaaaac ttgagcccat | 300 |
| ataccttgct atggatttgg cacacagacc aagctttcga agcaactgtt tggttgattc | 360 |
| ggaattgttt tctgataata aataatattt atattattcg ttatgtgttt gtgataggat | 420 |
| aactcggaac ataagcaact ttaacttgtg gcgatgcgag aaccaatgtg aaataggcat | 480 |
| gtgagagacc acattgtccc acagcttttg tcctcttcac ccccgcaatt atattaccat | 540 |
| taattaatca catagttatc gtttttccaaa tcgtaatata catatcgtag ttgttcatct | 600 |
| ttaatctatt ttcggtaatc taacaaaaag aaagatatct cgtagtgaaa atacgaatat | 660 |
| cagtgctttt tatgcaacaa ttatgacatt aggtatcgtt actcaaagtt aaatgaatac | 720 |
| aatctagacg acgcttaaaa aacgaataga tgatggaatc acgacttaac actagaatta | 780 |
| ccatggaata taggcaattt gcgaatttat tcaaccaaac caaaaatcga cagtgttatt | 840 |
| tagtcaaacc ttctaagaaa aagtgaccca tttccaagga acgatgaata aaaaaaccgg | 900 |
| accaatgttg ttccgacata agtcactagt ggcaaagtca taatttagac aaaggaaagg | 960 |
| ggcctttctt gcacaatttt gcatataaga gctctctctc ctcctcgttc cattgcactg | 1020 |
| gtctattcca ctcccactaa acattccttc tctcgctcac tcttctccaa tccttatttt | 1080 |
| atttttgaa agtttaaaat tttatacaac atatcaattt ggggtagaaa aattcgaaag | 1140 |
| aaaa | 1144 |

<210> SEQ ID NO 8
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP0190
<220> FEATURE:
<221> NAME/KEY: misc_feature
<222> LOCATION: (1)..(1002)
<223> OTHER INFORMATION: Wassilewskija ecotype

<400> SEQUENCE: 8

| taaatagtga cattggtaag aagaaaaaaa acactattaa atagtgaaaa aatggtttat | 60 |
| aactctctta attaacatta cttattattg ctagcaccta aaatctccca caaaatattt | 120 |

-continued

| | |
|---|---|
| gttgtaaaac acaaatttac aaaatgattt tgtttttaaa ttagtaacac atgttcatat | 180 |
| atacgttaat aagaacatac cctatatgat tttatataaa aaaatttctt tgagacgtct | 240 |
| tattctttt tctttaataa tatgcaattg tgagagtttg gatttgaatg gtagcattag | 300 |
| aagcaaactt gaaccaaaca tatttcatga agtcaaactt gaaccaatgt gatcactaat | 360 |
| cacagtgttc gcagtgtaag gcatcagaaa atagaagaag ggacatagct atgaatcata | 420 |
| taatcttgac acatgtttta taggttttag gtgtgtatgc taacaaaaaa tgagacagct | 480 |
| ttcttctaat agacttaata tttgggctaa atgtaccaca gttgtgaatt tcttacaaaa | 540 |
| atgggccgag ctacaaaaaa ctacaggccc actctcaact cttatcaaac gacagcgttt | 600 |
| tactttttta aaagcacaca cttttttgttt ggtgtcggtg acggtgagtt tcgtccgctc | 660 |
| ttcctttaaa ttgaagcaac ggttttgatc cgatcaaatc caacggtgct gattacacaa | 720 |
| agcccgagac gaaaacgttg actattaagt taggttttaa tctcagccgt taatctacaa | 780 |
| atcaacggtt ccctgtaaaa cgaatcttcc ttccttcttc acttccgcgt cttctctctc | 840 |
| aatcacctca aaaaaatcga tttcatcaaa atattcaccc gcccgaattt gactctccga | 900 |
| tcatcgtctc cgaatctaga tcgacgagat caaaacccta gaaatctaaa tcggaatgag | 960 |
| aaattgattt tgatacgaat tagggatctg tgtgttgagg ac | 1002 |

<210> SEQ ID NO 9
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 9

| | |
|---|---|
| tttcgatcct cttctttttt aggtttcttg atttgatgat cgccgccagt agagccgtcg | 60 |
| tcggaagttt cagagattaa aaccatcacc gtgtgagttg gtagcgaatt aacggaaagt | 120 |
| ctaagtcaag attttttaaa aagaaattta tgtgtgaaaa gaagccgttg tgtatattta | 180 |
| tataatttag aaaatgtttc atcattttaa ttaaaaaatt aataatttgt agaagaaaga | 240 |
| agcatttttt atacataaat catttacctt ctttactgtg ttttttcttca cttacttcat | 300 |
| ttttactttt ttacaaaaaa gtgaaaagta aattacgtaa ttggtaacat aaattcactt | 360 |
| taaatttgca tatgttttgt tttcttcgga aactatatcg aaaagcaaac ggaaagaact | 420 |
| tcacaaaaaa ccctagctaa ctaaagacgc atgtgttctt cttattcttc atatatcctc | 480 |
| tgtttcttgt gttctgtttt gagtcttaca ttttcaatat ctgactctga ttactatatc | 540 |
| taaaagggaa catgaagaac ttgagaccat gttaaactgt acaatgcctt caaacatggc | 600 |
| taactaaaga tacattagat ggctttacag tgtgtaatgc ttattatctt taggtttttt | 660 |
| aaatcccttg tattaagtta tttaccaaat tatgttcttg tactgcttat tggcttggtt | 720 |
| gttgtgtgct ttgtaaacaa caccctttggc tttatttcat cctttgtaaa cctactggtc | 780 |
| tttgttcagc tcctcttgga agtgagtttg tatgcctgga acgggtttta atggagtgtt | 840 |
| tatcgacaaa aaaaaaatgt agcttttgaa atcacagaga gtagttttat attcaaatta | 900 |
| catgcatgca actaagtagc aacaaagttg atatggccga gttggtctaa ggcgccagat | 960 |
| taaggttctg gtccgaaagg gcgtgggttc aaatcccact gtcaacattc tcttttttctc | 1020 |
| aaattaatat ttttctgcct caatggttca ggcccaatta tactagacta ctatcgcgac | 1080 |
| taaaatagg actagccgaa ttgatccggc ccagtatcag ttgtgtatca ccacgttatt | 1140 |

| | |
|---|---:|
| tcaaatttca aactaaggga taaagatgtc atttgacata tgagatattt ttttgctcca | 1200 |
| ctgagatatt tttctttgtc caagataaa atatcttttc tcgcatcgtc gtctttccat | 1260 |
| ttgcgcatta aaccaaaaag tgtcacgtga tatgtcccca accactacga attttaacta | 1320 |
| cagatttaac catggttaaa ccagaattca cgtaaaccga ctctaaacct agaaaatatc | 1380 |
| taaaccttgg ttaatatctc agccccctta taaataacga gacttcgtct acatcgttct | 1440 |
| acacatctca ctgctcacta ctctcactgt aatcccttag atcttctttt caaatttcac | 1500 |
| cattgcactg gatg | 1514 |

<210> SEQ ID NO 10
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0050
<220> FEATURE:
<221> NAME/KEY: misc_feature
<222> LOCATION: (1)..(999)
<223> OTHER INFORMATION: Columbia ecotype

<400> SEQUENCE: 10

| | |
|---|---:|
| tacttgaggg aaacatcata tttttaaacc ttgtctcagt aagctaacac acacccttg | 60 |
| tgattactta tccatgttta tccacaagaa tgcagttgga ttgagatatt ttcttctttg | 120 |
| ttgaaatcag gcctcaaggt gttcatgtgg tctgcaaaaa aattcccaaa ataaagata | 180 |
| gtgacatctg aaatcgataa tggattagac gaagagtttc gtgttattcc ttggtatggg | 240 |
| cgggtttggg gacagatatt ttggcacaga cgaggactag gccactgtgg tcctgcagca | 300 |
| ttaggtgtcc cttccatgtc ctgcattaca ttttattgat ggattcatca ccctatctac | 360 |
| tacaacggct acacaaacta tgaagagttt tgtttactaa taaatgccca agtgaggggt | 420 |
| cgatcgaacc cgggacacgt ttttcagttt accatataga attatccttg gaacccttga | 480 |
| tactccataa aacatcacca cctctgttgt catctcatga atccaggttc aaacctagtc | 540 |
| tctctctccc tagtgggagg tatatggcca ctgggccaat gatgacaaaa tgcaaaaaaa | 600 |
| ataaaataca tttgggttca ttatctaaaa tatctcttgt gtttgtaagt tttggttgca | 660 |
| cactcgtgtg gttgaagtgt gtgtgagagg tactatacaa tacactctgc ttttgttttg | 720 |
| tacctatctc tttctcttct ccacatatcc aagactttgg ggataaagct gagatcattg | 780 |
| gttgccattt ggttgtgtag aagcaatcac ccatttgctt tatccgaggt tgataaattt | 840 |
| cctcgggttc tccttctgac acgtatgaca aattctaata gtatattcct cgtagatatt | 900 |
| acctatatat tctcaatagt tgcaggtact taaggctttg tcttggcatc ctcgtcctct | 960 |
| tcagcaaaac tcgtctctct tgcactccaa aaagcaacc | 999 |

<210> SEQ ID NO 11
<211> LENGTH: 458
<212> TYPE: DNA
<213> ORGANISM: Arabidopsis thaliana
<220> FEATURE:
<221> NAME/KEY: misc_feature
<222> LOCATION: (1)..(458)
<223> OTHER INFORMATION: Ceres Promoter YP0050
<220> FEATURE:
<221> NAME/KEY: misc_feature
<222> LOCATION: (1)..(458)
<223> OTHER INFORMATION: Wassilewskija ecotype

<400> SEQUENCE: 11

| | |
|---|---|
| aatctgatct ctagtccagt cgattggtac ttgagggaaa catcatattt ttaaaccttg | 60 |
| tctcagtaag ctaacacaca ccccttgtga ttacttatcc atgtttatcc acaagaatgc | 120 |
| agttggattg agatattttc ttctttgttg aaatcaggcc tcaaggtgtt catgtggtct | 180 |
| gcaaaaaaat tcccaaaaat aaagatagtg acatctgaaa tcgataatgg attagacgaa | 240 |
| gagtttcgtg ttattccttg gtatgggcgg gtttggggac agatattttg gcacagacga | 300 |
| ggactaggcc actgtggtcc tgcagcatta ggtgtccctt ccatgtcctg cattacattt | 360 |
| tattgatgga ttcatcaccc tatctactac aacggctaca caaactatga gagttttgt | 420 |
| ttactaataa atgcccaagt gaggggtcga tcgaaccc | 458 |

<210> SEQ ID NO 12
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 12

| | |
|---|---|
| gtgggtaaaa gtatccttct ttgtgcattt ggtattttta agcatgtaat aagaaaaacc | 60 |
| aaaatagacg gctggtattt aataaaagga gactaatgta tgtatagtat atgatttgtg | 120 |
| tggaatataa taaagttgta aaatatagat gtgaagcgag tatctatctt ttgactttca | 180 |
| aaggtgatcg atcgtgttct ttgtgatagt tttggtcgtc ggtctacaag tcaacaacca | 240 |
| ccttgaagtt ttcgcgtctc ggtttcctct tcgcatctgg tatccaatag catacatata | 300 |
| ccagtgcgga aaatggcgaa gactagtggg cttgaaccat aaggtttggc cccaatacgg | 360 |
| attccaaaca acaagcctag cgcagtcttt tgggatgcat aagactaaac tgtcgcagtg | 420 |
| atagacgtaa gatatatcga cttgattgga atcgtctaag ctaataagtt taccttgacc | 480 |
| gtttatagtt gcgtcaacgt ccttatggag attgatgccc atcaaataaa cctgaaaatc | 540 |
| catcaccatg accaccataa actcccttgc tgccgctgct ttggcttgag caaggtgttt | 600 |
| ccttgtaaag ctccgatctt tggataaagt gttccacttt ttgcaagtag ctctgacccc | 660 |
| tctcagagat gtcaccggaa tcttagacag aacctcctct gccaaatcac ttggaagatc | 720 |
| ggacaatgtc atcattttg caggtaattt ctccttcgtt gctgctttgg cttgagcacg | 780 |
| gtgcttcttt gtaaagctcc gatctttgga taagagcgga tcggaatcct ctaggaggtg | 840 |
| ccagtcccctt gacctattaa tttatagaag gttttagtgt attttgttcc aatttcttct | 900 |
| ctaacttaac aaataacaac tgcctcatag tcatgggctt caaattttat cgcttggtgt | 960 |
| atttcgttat ttgcaaggcc ttggcccatt tgagcccaa taactaaatc tagccttttc | 1020 |
| agaccggaca tgaacttcgc atattggcgt aactgtgcag ttttaccttt ttcggatcag | 1080 |
| acaagatcag atttagacca cccaacaata gtcagtcata tttgacaacc taagctagcc | 1140 |
| gacactacta aaaagcaaac aaaagaagaa ttctatgttg tcattttacc ggtggcaagt | 1200 |
| ggacccttct ataaaagagt aaagagacag cctgtgtgtg tataatctct aattatgttc | 1260 |
| accgacacaa tcacacaaac ccttctctaa tcacacaact tcttcatgat ttacgacatt | 1320 |
| aattatcatt aactctttaa attcacttta catgctcaaa aatatctaat ttgcagcatt | 1380 |
| aatttgagta ccgataacta ttattataat cgtcgtgatt cgcaatcttc ttcattagat | 1440 |
| gctgtcaagt tgtactcgca cgcggtggtc cagtgaagca aatccaacgg tttaaaacct | 1500 |
| tcttacattt ctagatctaa tctgaaccgt cagatatcta gatctcattg tctgaacaca | 1560 |

```
gttagatgaa actgggaatg aatctggacg aaattacgat cttacaccaa ccccctcgac      1620
gagctcgtat atataaagct tatacgctcc tccttcacct tcgtactact actaccacca      1680
catttcttta gctcaacctt cattactaat ctccttttaa ggtatgttca cttttcttcg      1740
attcatactt tctcaagatt cctgcatttc tgtagaattt gaaccaagtg tcgattttg       1800 tttgagagaa gtgttgattt atagatctgg ttattgaatc tagattccaa ttttttaattg    1860 attcgagttt gttatgtgtg tttatactac ttctcattga tcttgtttga tttctctgct     1920
ctgtattagg tttctttcgt gaatcagatc ggaa                                 1954
```

<210> SEQ ID NO 13
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0633

<400> SEQUENCE: 13

```
ttaatctgag tcctaaaaac tgttatactt aacagttaac gcatgatttg atggaggagc       60
catagatgca attcaatcaa actgaaattt ctgcaagaat ctcaaacacg gagatctcaa      120
agtttgaaag aaaatttatt tcttcgactc aaaacaaact tacgaaattt aggtagaact      180
tatatacatt atattgtaat ttttttgtaac aaaatgtttt tattattatt atagaatttt    240
actggttaaa ttaaaaatga atagaaaagg tgaattaaga ggagagagga ggtaaacatt      300
ttcttctatt ttttcatatt ttcaggataa attattgtaa aagtttacaa gatttccatt      360
tgactagtgt aaatgaggaa tattctctag taagatcatt atttcatcta cttcttttat     420
cttctaccag tagaggaata aacaatattt agctcctttg taaatacaaa ttaattttcg     480
ttcttgacat cattcaattt taattttacg tataaaataa aagatcatac ctattagaac     540
gattaaggag aaatacaatt cgaatgagaa ggatgtgccg tttgttataa taaacagcca     600
cacgacgtaa acgtaaaatg accacatgat gggccaatag acatggaccg actactaata    660
atagtaagtt acatttttagg atggaataaa tatcataccg acatcagttt gaaagaaaag    720
ggaaaaaaag aaaaaataaa taaaagatat actaccgaca tgagttccaa aaagcaaaaa     780
aaaagatcaa gccgacacag acacgcgtag agagcaaaat gactttgacg tcacaccacg    840
aaaacagacg cttcatacgt gtcccttat ctctctcagt ctctctataa acttagtgag      900
accctcctct gttttactca caaatatgca aactagaaaa caatcatcag gaataaaggg    960
tttgattact tctattggaa agaaaaaaat ctttggaaaa                           1000
```

<210> SEQ ID NO 14
<211> LENGTH: 2003
<212> TYPE: DNA
<213> ORGANISM: Arabidopsis thaliana
<220> FEATURE:
<221> NAME/KEY: misc_feature
<222> LOCATION: (1)..(2003)
<223> OTHER INFORMATION: Ceres Promoter 32449

<400> SEQUENCE: 14

```
ttcttcaggt cttctctgta gctctgttac ttctatcaca gttatcgggt atttgagaaa       60
aaagagttag ctaaaatgaa tttctccata taatcatggt ttactacagg tttacttgat      120
tcgcgttagc tttatctgca tccaaagttt tttccatgat gttatgtcat atgtgatacc      180
gttactatgt ttataacttt atacagtctg gttcactgga gtttctgtga ttatgttgag      240
```

```
tacatactca ttcatccttt ggtaactctc aagtttaggt tgtttgaatt gcctctgttg      300
tgatacttat tgtctattgc atcaatcttc taatgcacca ccctagacta tttgaacaaa      360
gagctgtttc attcttaaac ctctgtgtct ccttgctaaa tggtcatgct ttaatgtctt      420
cacctgtctt tctcttctat agatatgtag tcttgctaga tagttagttc tacagctctc      480
ttttgtagtc ttgttagaga gttagttgag atattacctc ttaaaagtat ccttgaacgc      540
tttccggtta tgaccaattt gttgtagctc cttgtaagta gaacttactg ggaccagcga      600
gacagtttat gtgaatgttc atgcttaagt gtcgaacgta tctatctcta ctatagctct      660
gtagtcttgt tagacagtta gttttatatc tccattttt tgtagtcttg ctagttgaga       720
tattacctct tctcttcaaa gtatccttga acgctcaccg gttatgaaat ctctacacta      780
tagctctgta gtcttgctag atagttagtt ctttagctct ctttttgtag cctagttctt      840
tagctctcct tttgtagcct tgctacagag taagatggga tattacctcc ttgaacgctc      900
tccggttatg accaatttgt tgtagctcct tgtaagtaga acttaggata gagtgagtca      960
actttaagaa agaacctagt atgtggcata accagattgc aggctctgtc tcggctacag     1020
taacgtaact ctatagctct ttgtttttgtt cagaaagaac cagtgattgg atgattcgtc    1080
cttagaaact ggacctaaca acagtcattg gctttgaaat caagccacaa caatgcctat     1140
atgaaccgtc catttcattt atccgtttca aaccagccca ttacatttcg tcccattgat     1200
aaccaaaagc ggttcaatca gattatgttt taattttacc aaattcttta tgaagtttaa     1260
attatactca cattaaaagg attattggat aatgtaaaaa ttctgaacaa ttactgattt     1320
tggaaaatta acaaatattc tttgaaatag aagaaaaagc ctttttcctt ttgacaacaa    1380
catataaaat catactccca ttaaaaagat tttaatgtaa aattctgaat ataagatatt     1440
ttttacaaca acaaccaaaa atatttattt ttttcctttt ttacagcaac aagaaggaaa     1500
aacttttttt tttgtcaaga aaggggaga ttatgtaaac agataaaaca gggaaaataa     1560
ctaaccgaac tctcttaatt aacatcttca ataaggaaa attatgatcc gcatatttag     1620
gaagatcaat gcattaaaac aacttgcacg tggaaagaga gactatacgc tccacacaag    1680
ttgcactaat ggtacctctc acaaaccaat caaaatactg aataatgcca acgtgtacaa    1740
attagggttt tacctcacaa ccatcgaaca ttctcgaaac attttaaaca gcctggcgcc    1800
atagatctaa actctcatcg accaattttt gaccgtccga tggaaactct agcctcaacc    1860
caaaactcta tataaagaaa tcttttcctt cgttattgct taccaaatac aaaccctagc    1920
cgccttattc gtcttcttcg ttctctagtt ttttcctcag tctctgttct tagatcccctt   1980 gtagtttcca aatcttccga taa                                            2003
```

<210> SEQ ID NO 15
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0158

<400> SEQUENCE: 15

```
ttattagatt aatagattgc attgcattgc ttgtgctttc aatttacaaa ttgtctccca       60
actccatcga cacatctctt tttgtgtata taagattcag acttgttata ttttttttat      120
aaatatgtta ttagcatctt aagttaaatt gatttttat atctgcatta aggattacac      180
gactatattt gcgattgtgt gttggttaaa atataattta ggattgtctt taactacatt      240
```

-continued

```
taggattata tgactatatt tggttaaata taaaatctag ctgtgattat tagtattcaa    300
aaataagtag cctaaccaat taaaacaacg gctattgggg caaattagaa cattttagtg    360
tgtccaaaat ataatggtca ttaggtcata ttcctcctag cttcatcgca gcataattga    420
atgattgcct tatttagaag agcttttcca ctttcccaaa atctaggtgg gatctttttg    480
ttttgacctt cattttttctt gtttaccatt tttagctaaa ttatttacga ttacaaaaga    540
tatcaaaagt tggatcataa tacaatttat agacttactg tagaaaattc gtatgtacaa    600
gtacaacaaa ttcttcataa taaatttga aaattctatt acaaatgttg taagaaatag    660
aatttgaaat atatataaac taaggagaaa aaaaagaga acatgcattg ctctagtcag    720
agtggaccaa catcaacgag ataagataac ataaaaacca actcaccata actaaaaaca    780
tcccaagaga tccaacgatt catatcaaac acaaaaacat cgaacgatca gatttaaacc    840
atctctggta tctccaaaac acaaacactt ttttttttct tttgtctgaa tggaacaaaa    900
gcatgcgaca tctctgtgtc tttatcttct ctctcctctt cttgaaaaac tgaacccttta    960 attctttctt cacatctcct ttagctttct gaagctgcta                          1000
```

<210> SEQ ID NO 16
<211> LENGTH: 1100
<212> TYPE: DNA
<213> ORGANISM: Arabidopsis thaliana
<220> FEATURE:
<221> NAME/KEY: misc_feature
<222> LOCATION: (1)..(1100)
<223> OTHER INFORMATION: Ceres Promoter YP0214

<400> SEQUENCE: 16

```
ccagtcgatt ggcgcctcgc atgcctatca tatttaaccg tcaataatgg atttggcggt     60
tttggtaggc cgggtcaacc ggattaaaag aaaacggttt ggagtccttc cttgcaattg    120
aattttcaca cattcgggtt ttgtgatttc tctgtcataa tgggcccggc acatatggtt    180
cataacccat gtgggcctat ggtataattt ttccaattaa aactattgtt aggtcgataa    240
aacaaaaaac aataaaaacg agtggaatac acataccaaa aagaatgtga tgaacattag    300
taattttatt ttgatggtta atgaaaaaca aaataaatgc atcttggcat cttccgttgg    360
aaagcgcaaa tagggcagat tttcagacag atatcactat gatgggggt gagagaaaga    420 aaacgaggcg tacctaatgt aacactactt aattagtcgt tagttatagg actttttttt    480
tgtttgggcc tagttatagg atcataaggt aaaaatgaag aatgaatatt agattagtag    540
gagctaatga tggagttaag tatgcacgtg taagaactgg gaagtgaaac ctcctgtatg    600
gtgaagaaac tatacaacaa agcccttgt tggtgtatac gtattaattt ttattcttt     660 atcacaagcg atacgtatct taagacataa taaatatata tcttactcat aataaatatc    720
ttaagatata tatacagtat acacctgtat atatataata aataggcata tagtagaaat    780
taatatgagt tgttgttgtt gcaaatatat aaatcaatca aaagatttaa acccaccat     840 tcaatcttgg taagtaacga aaaaaaggg aagcaagaag aaccacagaa aagggggcta    900
acaactagac acgtagatct tcatctgccc gtccatctaa cctaccacac tctcatcttc    960 ttttcccgt gtcagtttgt tatataagct ctcactctcc ggtatatttc cccattgcac    1020
tggacactct catcttcttt ttcccgtgtc agtttgttat ataagctctc actctccggt    1080
atatttcccc attgcactgg                                                1100
```

<210> SEQ ID NO 17
<211> LENGTH: 999
<212> TYPE: DNA

<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0380

<400> SEQUENCE: 17

```
acaagtacca ttcactttt tacttttcaa tgtatacaat catcatgtga taaaaaaaaa    60
aatgtaacca atcaacacac tgagatacgg ccaaaaaatg gtaatacata aatgtttgta   120
ggttttgtaa tttaaatact ttagttaagt tatgatttta ttattttttgc ttatcactta   180
tacgaaatca tcaatctatt ggtatctctt aatcccgctt tttaatttcc accgcacacg   240
caaatcagca aatggttcca gccacgtgca tgtgaccaca tattgtggtc acagtactcg   300
tccttttttt ttcttttgta atcaataaat ttcaatccta aaacttcaca cattgagcac   360
gtcggcaacg ttagctccta aatcataacg agcaaaaaag ttcaaattag ggtatatgat   420
caattgatca tcactacatg tctacataat taatatgtat tcaaccggtc ggtttgttga   480
tactcatagt taagtatata tgtgctaatt agaattagga tgaatcagtt cttgcaaaca   540
actacggttt catataatat gggagtgtta tgtacaaaat gaaagaggat ggatcattct   600
gagatgttat gggctcccag tcaatcatgt tttgctcgca tatgctatct tttgagtctc   660
ttcctaaact catagaataa gcacgttggt ttttccacc gtcctcctcg tgaacaaaag    720
tacaattaca ttttagcaaa ttgaaaataa ccacgtggat ggaccatatt atatgtgatc   780
atattgcttg tcgtcttcgt tttcttttaa atgtttacac cactacttcc tgacacgtgt   840
ccctattcac atcatccttg ttatatcgtt ttacttataa aggatcacga acaccaaaac   900
atcaatgtgt acgtcttttg cataagaaga aacagagagc attatcaatt attaacaatt   960
acacaagaca gcgagattgt aaaagagtaa gagagagag                          999
```

<210> SEQ ID NO 18
<211> LENGTH: 669
<212> TYPE: DNA
<213> ORGANISM: Arabidopsis thaliana
<220> FEATURE:
<221> NAME/KEY: misc_feature
<222> LOCATION: (1)..(669)
<223> OTHER INFORMATION: Ceres Promoter PT0848

<400> SEQUENCE: 18

```
tctctttaaa tcagttaact aaccgtttat atatttacga taaggtttga agagattatt    60
gataaaataa tacatttcat aatcccgcgt tcaaccgttt aaagtaacat ttaagttgac   120
tatatctaat ttttttttcca ttaaatatgg agctggtaaa ctttatcaac ttctaaaaag   180
tgtaacaaca aaaattaggt caatcacaat tctgttttttt ttattatttt ggattgactt   240
ccaattgcaa atagtcttag tgatcaccat tatcatacat atatacatca agtaggtttc   300
atcatgatat accacaaagt atttgacaag ccatatggtt ttggatcaaa aagtcggtcc   360
aaaattaatg ttttatgtgc aagaaccgac ccattgtaca cacgtgttaa catcttcaag   420
actttcatct ctattttttct tttggtcatt aagatacccca ttgatccgaa tctgttacat   480
tcccacctac ttttttaatt tttactatcc actccaaatt aaacacaacc gatgatttta   540
ataattggaa gcttttaaaa atatttcaaa acaagcctct ttgtgtttgt ctatatatat   600
acacgtaata agaaggtgaa tgaatctcac agcttacttg ttctaaggct tccaataacg   660
aaaacagta                                                           669
```

<210> SEQ ID NO 19

<211> LENGTH: 3379
<212> TYPE: DNA
<213> ORGANISM: Arabidopsis thaliana
<220> FEATURE:
<221> NAME/KEY: misc_feature
<222> LOCATION: (1)..(3379)
<223> OTHER INFORMATION: Ceres CDNA ID no. 23507479
<220> FEATURE:
<221> NAME/KEY: misc_feature
<222> LOCATION: (1)..(3379)
<223> OTHER INFORMATION: At_DWF4

<400> SEQUENCE: 19

```
taagatatat agatcgaact tgtttggaga accaacgatc gtatcagctg atgctggact    60
taatagattc atattacaaa acgaaggaag gctcttttgaa tgtagttatc ctagaagtat   120
aggtgggatt cttgggaaat ggtcgatgct tgttcttgtt ggtgacatgc atagagatat   180
gagaagtatc tcgcttaact tcttaagtca cgcacgtctt agaactattc tacttaaaga   240
tgttgagaga catactttgt ttgttcttga ttccttggcaa caaaactcta ttttctctgc   300
tcaagacgag gccaaaaagg ttttattttt tatctttat tttgctaaat tttttgttt     360
atgaatcttt agagtttcta acttttttt ttttaattga acagtttacg tttaatctaa   420
tggcgaagca tataatgagt atggatcctg agaagaaga aacagagcaa ttaaagaaag    480
agtatgtaac tttcatgaaa ggagttgtct ctgctcctct aaatctacca ggaactgctt   540
atcataaagc tcttcaggta catttatttt tttttgctgt aaagtcacaa actctcatta   600
taggttttta attttatttt atgtgttaaa taaaatatct aaaatggttg tgtagtcacg   660
agcaacgata ttgaagttca ttgagaggaa aatggaagag agaaaattgg atatcaagga   720
agaagatcaa gaagaagaag aagtgaaaac agaggatgaa gcagagatga gtaagagtga   780
tcatgttagg aaacaaagaa cagacgatga tcttttggga tgggttttga acattcgaa    840
tttatcgacg gagcaaattc tcgatctcat tcttagtttg ttatttgccg acatgagac    900
ttcttctgta gccattgctc tcgctatctt cttcttgcaa gcttgcccta aagccgttga   960
agagcttagg gtaagataat tataacagca caagttaatt actaccaaat tgttacgtat  1020
tatataagtt attatagaat tattctatta gaatatacga tgaaaaaagt atgtatattt  1080
aattgtcact aatttttatgt ttattgattt atacttttga aggaagagca tcttgagatc  1140
gcgagggcca agaaggaact aggagagtca gaattaaatt gggatgatta caagaaaatg  1200
gactttactc aatgtgtatg ttactatcat tctcattatt tattctatgt tcatatgatt  1260
tatgatgaaa ccaaaattat tgattttttt tttggtgtgt gtgaaggtta taaatgaaac  1320
tcttcgattg ggaaatgtag ttaggttttt gcatcgcaaa gcactcaaag atgttcggta  1380
caaaggtaaa actttacgta caaaattttt aaataatgaa atccggaata ttgaaatctt  1440
attggatgaa aaatattaaa ataatttaca tttcttaatg ttggaaaaaa ggatacgata  1500
tccctagtgg gtggaaagtg ttaccggtga tctcagccgt acatttggat aattctcgtt  1560
atgaccaacc taatctcttt aatccttgga gatggcaaca ggtaaataaa aagtttctct  1620
cgttaactat cgaaaattag tgtatagttt tttcatctat tgcatgaata gatacgtcct  1680
acgtgattta cctatctata gatactatac gagaactatt aatctggcaa aaactttta   1740
ttattattat ctttcaagtt agatcttaac acgtcatgga tcattgatca catgaaagca  1800
tataaattaa aaataagaga gagaaagaga cgtgttggtg taagtgtacg tgaagacaat  1860
taattagtag gatggtatgt ctttaatgac gtaggagctg cctaaatatt cttataatcg  1920
tgaccgttga tttattatta gtcacggctt tgatacaatt taagatttga cggacgatgg  1980
```

```
taccacggct tgacggatc tcacacgccc gatgacttgt acgtgcgtta gattctgcca      2040
cgttgactgg ttttaatact tagatttata actctattaa ttataacaac tatcaaatcg      2100
gcgaattaga gaaatatact atatagtatt attatgatta ttatgagata atactttatg      2160
aaataagata ataatggtag tcatgatgtt atagtgagtg gggaaggtaa gaggtggtga      2220
gagatgatta atgacccac gtggtgtggt gccaacaagc acgtgttctt cttccttttt       2280
tcttcccaac ttcttttttt gggggtttat tgtgatttat aaaatcggtt tgtcgttttt      2340
ttttgtgacg agcagcaaaa caacggagcg tcatcgtcag gaagtggtag ttttcgacg       2400
tggggaaaca actacatgcc gtttggagga gggccaaggc tatgtgctgg ttcagagcta      2460
gccaagttag aaatggcagt gtttattcat catctagttc ttaaattcaa ttgggaatta      2520
gcagaagatg atcaaccatt tgcttttcct tttgttgatt ttcctaacgg tttgcctatt      2580
agggtttctc gtattctgta aaaaaaaaaa aagatgaaag tattttatt ctcttctttt       2640
ttttttgata attttaaatc atttttttg cccaatgata tataaaaatt tggataaata       2700
atattattgg atattcgttt tttagttcgg gtttgagaaa agggtttcga ctttcgaaag      2760
tggacgatgt atatagattg ggagctaggt tgagtctttg acatttgta ttggatgttg       2820
ttgattatta gtgtcgacac tattaaacct taaatgggct ttctataagg cccaattata      2880
ttacgattat aacaaagtga caacttttac ttcgttttg atccgaagca ataacaaatt       2940
gtcaaatacc aaacacaaga attatgtaaa cactcgtgtg tgtctagtgg gaaatcattg      3000
ggctggagac tgaacatcag aacacaagaa acctgtcaat tatggataca cctcctatga     3060
cggtttccaa actttatctt gattcttatc gtgttacatt gacacaaaga gttaggtgtc     3120
aaaaggacta atgaataac aatagctctc aggataagaa ggttcataaa atggtttctt      3180
tattttgaga agaaagagag aggagctttt actgtttctt gggtcctatt cctttaaatg     3240
agagggtttc gttttactt cttctatctc atcatctta ggatcctctt ctagacgagt       3300
aaagtaatcc tcgttaccaa gcaatggtct catcttttga agacaggtct tttccaagtc     3360
ctagttcagg ccaaagctt                                                   3379
```

<210> SEQ ID NO 20
<211> LENGTH: 1913
<212> TYPE: DNA
<213> ORGANISM: Zea mays
<220> FEATURE:
<221> NAME/KEY: misc_feature
<222> LOCATION: (1)..(1913)
<223> OTHER INFORMATION: Ceres CDNA ID no. 23784066
<220> FEATURE:
<221> NAME/KEY: misc_feature
<222> LOCATION: (1)..(1913)
<223> OTHER INFORMATION: Also known as Ceres CLONE ID no. 234510
<220> FEATURE:
<221> NAME/KEY: misc_feature
<222> LOCATION: (1)..(1913)
<223> OTHER INFORMATION: Zm_DWF4

<400> SEQUENCE: 20

```
aaagagagaa gggagaggcg agggagctca ccaggagaga ggggcctgtg cgtgagcatt        60
gagcaaagca aaggaagcag tacatacata catatttctc tcgctcgctc gcagagaggc       120
ccggccggcc ggctccatgc aacaagggag gacgacgagc ggtggcggtg ggcgatgatg       180
atgatgatga tggcggggga gcacgtgctg gccgctctgg gcaccctact gctggcctcg       240
ctcctgaccc tggtgctgaa ccacttcctg cccttgcttc tgaacccaa ggcccccagg        300
ggaagcttcg ggtggccgct cctcggcgag acgctcaggt tcctcacgcc gcacgcctcc       360
```

-continued

| | |
|---|---|
| aacacgctgg gcggcttcct cgaggatcac tgctccaggt atgggcgggt gttcaagtcc | 420 |
| cacctgttct gcaccccgac ggtggtgtcc tgcgaccagg acctcaacca cttcatcctg | 480 |
| cagaacgagg agcggctgtt ccagtgcagc tacccgaggc cgatccatgg catcctgggc | 540 |
| aagtcctcca tgctcgtcgt cctgggcgag accacaagc gcctcaggaa cctggccctc | 600 |
| gccctcgtca cctccaccaa gctcaagccc agctacctag gcgacatcga agatcgcg | 660 |
| ctgcacgtcg tcggcgcatg gcgacggcac ggcagcagcg gcggcgtcag ggtcgtcgca | 720 |
| ttctgcgagg aggcaagaaa gttcgcattc agtgtgatag tgaagcaggt gctggggctg | 780 |
| tcgccagagg agccggtcac tgcaaggata ctggaggact tcctggcctt catgaaggga | 840 |
| ctcatctcct tccccctcta catcccaggg accccatatg ccaaggctgt ccgggcgaga | 900 |
| gagaggatat ccagcactgt gaagggcatc atcaaggagc ggaggagcgc tgggtcatgg | 960 |
| aacaagcagg gcgacttcct tgacgtgctg ctgtcaagca acgagctatc tgacgaggag | 1020 |
| aaagtgagct ttgtgctgga ctccctgctg gagggtatg agaccacctc gctcctcatc | 1080 |
| tccatggtcg tttatttcct tggccagtct gctcaagatc tggacctggt taagagggag | 1140 |
| cacgacagca taagatccaa caaaggcaag gaggagtgct tgacttcaga agactacaag | 1200 |
| aagatggaat atacccaaca agtcatcaac gaggcgctga gatgcggcaa catcgtcaag | 1260 |
| ttcgtccacc ggaaggcgct gaaagacgtc aaatacaaag agtatctgat tccatctggc | 1320 |
| tggaaggtcc taccggtctt cactgccgtt catctgaacc cctcacttca tggagacgcg | 1380 |
| cagcagtttc agccctgtag gtgggagggc acaagccaag ggacaagcaa gaggtttaca | 1440 |
| ccgttcggtg gtggccccg gctctgccca ggatcagagc tcgctaaagt ggagactgct | 1500 |
| ttcttcctcc atcaccttgt cctcaattat agatggagaa ttgatggcga tgacattcca | 1560 |
| atggcatacc cgtatgtgga gtttcagaga ggtctgccaa tagaaatcga gccaacgtcc | 1620 |
| cctgaatctt gactgtcctg gagctacagc catcagttat cacaccagag agaaaagggg | 1680 |
| aaggtgcatg gagtatacat gaatggtcag tgacagatct cacaagtgaa ggaacactga | 1740 |
| gggcgcgtgc tagtagctag catatgaggc agctgagact gtaatttaat gtacatggtg | 1800 |
| tagatatatt ttgtccatgg caattgcttg aagtggctga ttcacttcac cctgtaaaac | 1860 |
| attctccagt ggtttcaact gctatcctat aaaaaagaag ggccctgtg ttt | 1913 |

<210> SEQ ID NO 21
<211> LENGTH: 1509
<212> TYPE: DNA
<213> ORGANISM: Oryza sativa
<220> FEATURE:
<221> NAME/KEY: misc_feature
<222> LOCATION: (1)..(1509)
<223> OTHER INFORMATION: Ceres CDNA ID no. 6784682
<220> FEATURE:
<221> NAME/KEY: misc_feature
<222> LOCATION: (1)..(1509)
<223> OTHER INFORMATION: Os_DWF4

<400> SEQUENCE: 21

| | |
|---|---|
| atggcgtcca taaccagcga gctgctcttc tttctcccct tcatcctcct tgccctgctc | 60 |
| acgttctaca ccaccaccgt ggccaaatgc cacggcgggc actggtggcg aggtgggacg | 120 |
| acgccggcga agaggaagcg gatgaacctg ccgcccggcg ccgccgggtg ccgctcgtc | 180 |
| ggcgagacgt tcggctacct ccgcgcccac cccgccacct ccgtcggccg cttcatggag | 240 |
| cagcacatcg cacggtacgg gaagatatac cggtcgagcc tgttcgggga gcggacggtg | 300 |
| gtgtcggcgg acgcggggct caaccggtac atcctgcaga acgaggggag gctgttcgag | 360 |

```
tgcagctacc cgcgcagcat cggcggcatc ctgggcaagt ggtccatgct ggtcctcgtc    420
ggggacccgc accgcgagat gcgcgccatc tccctcaact tcctctcctc cgtccgcctc    480
cgcgccgtcc tcctccccga ggtcgagcgc cacaccctcc tcgtcctccg cgcctggctc    540
ccttcctcca ccttctccgc tcagcaccaa gccaagaagt tcacgttcaa cctgatggcg    600
aagaacataa tgagcatgga cccggggag gaagagacgg agcggctgcg gcgggagtac     660
atcaccttca tgaagggcgt ggtctccgcg ccgctcaacc tgcccgggac gccctactgg    720
aaggctctca agtcgcgtgc tgccattctc ggagtaatag agaggaaaat ggaagagcgg    780
gttgagaagc tgagcaagga ggatgcaagc gtagagcaag acgatcttct cggatgggct    840
ctgaaacaat ctaaccttcc aaaagagcaa atcctggacc tcttgctgag cttgctcttc    900
gccgggcacg agacgtcgtc catggcgctc gccctcgcca tcttcttcct tgaaggctgc    960
cccaaggctg tccaagaact gagggaggag catcttggga ttgcaaggag acaaaggcta   1020
agaggggagt gcaaattgag ctgggaagac tacaaagaga tggttttcac gcaatgtgtc   1080
ataaacgaga cgttgcggct aggaaacgtg gtcaggttcc tgcaccggaa ggtcatcaag   1140
gacgtgcact acaagggtta tgacattcca agcggatgga agatcctgcc ggtgttagcc   1200
gcggtgcatc tggactcgtc cctgtacgag gaccccagc gcttcaatcc ctggagatgg    1260
aagagtagcg gatcatccgg cggcttggct cagagcagca gcttcatgcc gtacggcggc   1320
gggacgcggc tgtgcgccgg gtcggagctc gcgaagctgg agatggccgt gttcttgcac   1380
cacctggtgc tcaacttcag gtgggagctc gccgagccgg accaagcctt cgtcttcccc   1440
ttcgtcgact tccccaaggg ccttcccatt agggttcata gaattgcaca ggatgatgag   1500
caggagtaa                                                           1509
```

<210> SEQ ID NO 22
<211> LENGTH: 512
<212> TYPE: PRT
<213> ORGANISM: Artificial Sequence
<220> FEATURE:
<221> NAME/KEY: misc_feature
<222> LOCATION: (1)..(512)
<223> OTHER INFORMATION: Ortholog_#1_to_At_DWF4

<400> SEQUENCE: 22

```
Met Phe Glu Thr Glu His His Thr Val Leu Pro Leu Leu Leu Pro Ser
1               5                   10                  15

Leu Leu Ser Leu Leu Leu Phe Leu Ile Leu Leu Lys Arg Arg Asn Arg
            20                  25                  30

Lys Thr Arg Phe Asn Leu Pro Pro Gly Lys Ser Gly Trp Pro Phe Leu
        35                  40                  45

Gly Glu Thr Ile Gly Tyr Pro Lys Pro Tyr Thr Ala Thr Thr Leu Gly
    50                  55                  60

Asp Phe Met Gln Gln His Val Ser Lys Tyr Gly Lys Ile Tyr Arg Ser
65                  70                  75                  80

Asn Leu Phe Gly Glu Pro Thr Ile Val Ser Ala Asp Ala Gly Leu Asn
                85                  90                  95

Arg Phe Ile Leu Gln Asn Glu Gly Arg Leu Phe Glu Cys Ser Tyr Pro
            100                 105                 110

Arg Ser Ile Gly Gly Ile Leu Gly Lys Trp Ser Met Leu Val Leu Val
        115                 120                 125

Gly Asp Met His Arg Asp Met Arg Ser Ile Ser Leu Asn Phe Leu Ser
    130                 135                 140

His Ala Arg Leu Arg Thr Ile Leu Leu Lys Asp Val Glu Arg His Thr
```

```
              145                 150                 155                 160
Leu Phe Val Leu Asp Ser Trp Gln Gln Asn Ser Ile Phe Ser Ala Arg
                165                 170                 175

Asp Glu Ala Lys Lys Phe Thr Phe Asn Leu Met Ala Lys His Ile Met
            180                 185                 190

Ser Met Asp Pro Gly Glu Glu Thr Glu Gln Leu Lys Lys Glu Tyr
            195                 200                 205

Val Thr Phe Met Lys Gly Val Ser Ala Pro Leu Asn Leu Pro Gly
            210                 215                 220

Thr Ala Tyr His Lys Ala Leu Gln Ser Arg Ala Thr Ile Leu Lys Phe
225                 230                 235                 240

Ile Glu Arg Lys Met Glu Glu Arg Lys Leu Asp Ile Lys Glu Glu Asp
                245                 250                 255

Gln Glu Glu Glu Val Lys Thr Glu Asp Glu Ala Glu Val Ser Lys
                260                 265                 270

Ser Asp His Val Arg Lys Gln Arg Thr Asp Asp Leu Leu Gly Trp
            275                 280                 285

Val Leu Lys His Ser Asn Leu Ser Thr Glu Gln Ile Leu Asp Leu Ile
            290                 295                 300

Leu Ser Leu Leu Phe Ala Gly His Glu Thr Ser Ser Val Ala Ile Ala
305                 310                 315                 320

Leu Ala Ile Phe Phe Leu Gln Ala Cys Pro Lys Ala Val Glu Glu Leu
                325                 330                 335

Arg Glu Glu His Leu Glu Ile Ala Arg Ala Lys Lys Gly Leu Gly Glu
            340                 345                 350

Ser Glu Leu Asn Trp Asp Asp Tyr Lys Lys Met Asp Phe Thr Gln Cys
            355                 360                 365

Val Ile Asn Glu Thr Leu Arg Leu Gly Asn Val Val Arg Phe Leu His
            370                 375                 380

Arg Lys Ala Leu Lys Asp Val Arg Tyr Lys Gly Tyr Asp Ile Pro Ser
385                 390                 395                 400

Gly Trp Lys Val Leu Pro Val Ile Ser Ala Val His Leu Asp Asn Ser
                405                 410                 415

Arg Tyr Asp Gln Pro Asn Leu Phe Asn Pro Trp Arg Trp Gln Gln Gln
            420                 425                 430

Asn Asn Gly Ala Ser Ser Ser Gly Ser Phe Ser Thr Trp Gly
            435                 440                 445

Asn Asn Tyr Met Pro Phe Gly Gly Pro Arg Leu Cys Ala Gly Ser
            450                 455                 460

Glu Leu Ala Lys Leu Glu Met Ala Val Phe Ile His His Leu Val Leu
465                 470                 475                 480

Lys Phe Asn Trp Glu Leu Ala Glu Asp Asp Gln Pro Phe Ala Phe Pro
                485                 490                 495

Phe Val Asp Phe Pro Asn Gly Leu Pro Ile Arg Val Ser Arg Ile Leu
            500                 505                 510

<210> SEQ ID NO 23
<211> LENGTH: 512
<212> TYPE: PRT
<213> ORGANISM: Artificial Sequence
<220> FEATURE:
<221> NAME/KEY: misc_feature
<222> LOCATION: (1)..(512)
<223> OTHER INFORMATION: Ortholog_#2_to_At_DWF4

<400> SEQUENCE: 23
```

-continued

```
Met Phe Glu Thr Glu His His Thr Val Leu Pro Leu Leu Pro Ser
 1               5                  10                  15

Leu Leu Ser Leu Leu Phe Leu Ile Leu Val Lys Arg Arg Asn Arg
             20                  25                  30

Lys Thr Arg Phe Asn Leu Pro Pro Gly Lys Ser Gly Trp Pro Phe Leu
             35                  40                  45

Gly Glu Thr Ile Gly Tyr Pro Lys Pro Tyr Thr Ala Thr Thr Leu Gly
         50                  55                  60

Asp Phe Met Gln Gln His Val Ser Lys Tyr Gly Lys Ile Tyr Arg Ser
 65                  70                  75                  80

Asn Leu Phe Gly Glu Pro Thr Ile Val Ser Ala Asp Ala Gly Leu Asn
                 85                  90                  95

Arg Phe Ile Leu Gln Asn Glu Gly Arg Leu Phe Glu Cys Ser Tyr Pro
             100                 105                 110

Arg Ser Ile Gly Gly Ile Leu Gly Lys Trp Ser Met Leu Val Leu Val
             115                 120                 125

Gly Asp Met His Arg Asp Met Arg Ser Ile Ser Leu Asn Phe Leu Ser
 130                 135                 140

His Ala Arg Leu Arg Thr Ile Leu Leu Lys Asp Val Glu Arg His Thr
145                  150                 155                 160

Leu Phe Val Leu Asp Ser Trp Gln Gln Asn Ser Ile Phe Ser Ala Arg
                 165                 170                 175

Asp Glu Ala Lys Lys Phe Thr Phe Asn Leu Met Ala Lys His Ile Met
             180                 185                 190

Ser Met Asp Pro Gly Glu Glu Thr Glu Gln Leu Lys Lys Glu Tyr
             195                 200                 205

Val Thr Phe Met Lys Gly Val Val Ser Ala Pro Leu Asn Leu Pro Gly
 210                 215                 220

Thr Ala Tyr His Lys Ala Leu Gln Ser Arg Ala Thr Ile Leu Lys Phe
225                  230                 235                 240

Ile Glu Arg Lys Met Glu Arg Lys Leu Asp Ile Lys Glu Glu Asp
                 245                 250                 255

Gln Glu Glu Glu Val Lys Thr Glu Asp Glu Ala Glu Val Ser Lys
             260                 265                 270

Ser Asp His Val Arg Lys Gln Arg Thr Asp Asp Leu Leu Gly Trp
             275                 280                 285

Val Leu Lys His Ser Asn Leu Ser Thr Glu Gln Ile Leu Asp Leu Ile
 290                 295                 300

Leu Ser Leu Leu Phe Ala Gly His Glu Thr Ser Ser Val Ala Ile Ala
305                  310                 315                 320

Leu Ala Ile Phe Phe Leu Gln Ala Cys Pro Lys Ala Val Glu Glu Leu
                 325                 330                 335

Arg Glu Glu His Leu Glu Ile Ala Arg Ala Lys Lys Glu Leu Gly Glu
             340                 345                 350

Ser Glu Leu Asn Trp Asp Asp Tyr Lys Lys Met Asp Phe Thr Gln Cys
             355                 360                 365

Val Ile Asn Glu Thr Leu Arg Leu Gly Asn Val Arg Phe Leu His
 370                 375                 380

Arg Lys Ala Leu Lys Asp Val Arg Tyr Lys Gly Tyr Asp Ile Pro Ser
385                  390                 395                 400

Gly Trp Lys Val Leu Pro Val Ile Ser Ala Val His Leu Asp Asn Ser
                 405                 410                 415

Arg Tyr Asp Gln Pro Asn Leu Phe Asn Pro Trp Arg Trp Gln Gln Gln
             420                 425                 430
```

Asn Asn Gly Ala Ser Ser Gly Ser Gly Ser Phe Ser Thr Trp Gly
            435                 440                 445

Asn Asn Tyr Met Pro Phe Gly Gly Pro Arg Leu Cys Ala Gly Ser
        450                 455                 460

Glu Leu Ala Lys Leu Glu Met Ala Val Phe Ile His His Leu Val Leu
465                 470                 475                 480

Lys Phe Asn Trp Glu Leu Ala Glu Asp Gln Pro Phe Ala Phe Pro
                485                 490                 495

Phe Val Asp Phe Pro Asn Gly Leu Pro Ile Arg Val Ser Arg Ile Leu
            500                 505                 510

<210> SEQ ID NO 24
<211> LENGTH: 512
<212> TYPE: PRT
<213> ORGANISM: Artificial Sequence
<220> FEATURE:
<221> NAME/KEY: misc_feature
<222> LOCATION: (1)..(512)
<223> OTHER INFORMATION: Ortholog_#3_to_At_DWF4

<400> SEQUENCE: 24

Met Phe Glu Thr Glu His His Thr Val Leu Pro Leu Leu Pro Ser
1               5                   10                  15

Leu Leu Ser Leu Leu Leu Phe Leu Ile Leu Val Lys Arg Arg Asn Arg
                20                  25                  30

Lys Thr Arg Phe Asn Leu Pro Pro Gly Lys Ser Gly Trp Pro Phe Leu
            35                  40                  45

Gly Glu Thr Ile Gly Tyr Pro Lys Pro Tyr Thr Ala Thr Thr Leu Gly
    50                  55                  60

Asp Phe Met Gln Gln His Val Ser Lys Tyr Gly Lys Ile Tyr Arg Ser
65              70                  75                      80

Asn Leu Phe Gly Glu Pro Thr Ile Val Ser Ala Asp Ala Gly Leu Asn
                85                  90                  95

Arg Phe Ile Leu Gln Asn Glu Gly Arg Leu Phe Glu Cys Ser Tyr Pro
            100                 105                 110

Arg Ser Ile Gly Gly Ile Leu Gly Lys Trp Ser Met Leu Val Leu Val
        115                 120                 125

Gly Asp Met His Arg Asp Met Arg Ser Ile Ser Leu Asn Phe Leu Ser
130                 135                 140

His Ala Arg Leu Arg Thr Ile Leu Leu Lys Asp Val Glu Arg His Thr
145                 150                 155                 160

Leu Phe Val Leu Asp Ser Trp Gln Gln Asn Ser Ile Phe Ser Ala Arg
                165                 170                 175

Asp Glu Ala Lys Lys Phe Thr Phe Asn Leu Met Ala Lys His Ile Met
            180                 185                 190

Ser Met Asp Pro Gly Glu Glu Glu Thr Glu Gln Leu Lys Lys Glu Tyr
        195                 200                 205

Val Thr Phe Met Lys Gly Val Val Ser Ala Pro Leu Asn Leu Pro Gly
    210                 215                 220

Thr Ala Tyr His Lys Ala Leu Gln Ser Arg Ala Thr Ile Leu Lys Phe
225                 230                 235                 240

Ile Glu Arg Lys Met Glu Glu Arg Lys Leu Asp Ile Lys Glu Glu Asp
                245                 250                 255

Gln Glu Glu Glu Glu Met Lys Thr Glu Asp Glu Ala Glu Val Ser Lys
            260                 265                 270

Ser Asp His Val Arg Lys Gln Arg Thr Asp Asp Asp Leu Leu Gly Trp

```
                275                 280                 285
Val Leu Lys His Ser Asn Leu Ser Thr Glu Gln Ile Leu Asp Leu Ile
        290                 295                 300

Leu Ser Leu Leu Phe Ala Gly His Glu Thr Ser Ser Val Ala Ile Ala
305                 310                 315                 320

Leu Ala Ile Phe Phe Leu Gln Ala Cys Pro Lys Ala Val Glu Glu Leu
                325                 330                 335

Arg Glu Glu His Leu Glu Ile Ala Arg Ala Lys Lys Glu Leu Gly Glu
                340                 345                 350

Ser Glu Leu Asn Trp Asp Asp Tyr Lys Lys Met Asp Phe Thr Gln Cys
                355                 360                 365

Val Ile Asn Glu Thr Leu Arg Leu Gly Asn Val Val Arg Phe Leu His
        370                 375                 380

Arg Lys Ala Leu Lys Asp Val Arg Tyr Lys Gly Tyr Asp Ile Pro Ser
385                 390                 395                 400

Gly Trp Lys Val Leu Pro Val Ile Ser Ala Val His Leu Asp Asn Ser
                405                 410                 415

Arg Tyr Asp Gln Pro Asn Leu Phe Asn Pro Trp Arg Trp Gln Gln Gln
                420                 425                 430

Asn Asn Gly Ala Ser Ser Gly Ser Gly Ser Phe Ser Thr Trp Gly
        435                 440                 445

Asn Asn Tyr Met Pro Phe Gly Gly Pro Arg Leu Cys Ala Gly Ser
450                 455                 460

Glu Leu Ala Lys Leu Glu Met Ala Val Phe Ile His His Leu Val Leu
465                 470                 475                 480

Lys Phe Asn Trp Glu Leu Ala Glu Asp Asp Gln Pro Phe Ala Phe Pro
                485                 490                 495

Phe Val Asp Phe Pro Asn Gly Leu Pro Ile Arg Val Ser Arg Ile Leu
                500                 505                 510

<210> SEQ ID NO 25
<211> LENGTH: 512
<212> TYPE: PRT
<213> ORGANISM: Artificial Sequence
<220> FEATURE:
<221> NAME/KEY: misc_feature
<222> LOCATION: (1)..(512)
<223> OTHER INFORMATION: Ortholog_#4_to_At_DWF4

<400> SEQUENCE: 25

Met Phe Glu Thr Glu His His Thr Val Leu Pro Leu Leu Pro Ser
1               5                   10                  15

Leu Leu Ser Leu Leu Leu Phe Leu Ile Leu Val Lys Arg Arg Asn Arg
                20                  25                  30

Lys Thr Arg Phe Asn Leu Pro Pro Gly Lys Ser Gly Trp Pro Phe Leu
            35                  40                  45

Gly Glu Thr Ile Gly Tyr Pro Lys Pro Tyr Thr Ala Thr Thr Leu Gly
        50                  55                  60

Asp Phe Met Gln Gln His Val Ser Lys Tyr Gly Lys Ile Tyr Arg Ser
65                  70                  75                  80

Asn Leu Phe Gly Glu Pro Thr Ile Val Ser Ala Asp Ala Gly Leu Asn
                85                  90                  95

Arg Phe Ile Leu Gln Asn Glu Gly Arg Leu Phe Glu Cys Ser Tyr Pro
                100                 105                 110

Arg Ser Ile Gly Gly Ile Leu Gly Lys Trp Ser Met Leu Val Leu Val
            115                 120                 125
```

```
Gly Asp Met His Arg Asp Met Arg Ser Ile Ser Leu Asn Phe Leu Ser
        130                 135                 140

His Ala Arg Leu Arg Thr Ile Leu Leu Lys Asp Val Glu Arg His Thr
145                 150                 155                 160

Leu Phe Val Leu Asp Ser Trp Gln Gln Asn Ser Ile Phe Ser Ala Arg
                165                 170                 175

Asp Glu Ala Lys Lys Phe Thr Phe Asn Leu Met Ala Lys His Ile Met
            180                 185                 190

Ser Met Asp Pro Gly Glu Glu Thr Glu Gln Leu Lys Lys Glu Tyr
        195                 200                 205

Val Thr Phe Met Lys Gly Val Val Ser Ala Pro Leu Asn Leu Pro Gly
210                 215                 220

Thr Ala Tyr His Lys Ala Leu Gln Ser Arg Ala Thr Ile Leu Lys Phe
225                 230                 235                 240

Ile Glu Arg Lys Met Glu Glu Arg Lys Leu Asp Ile Lys Glu Glu Asp
                245                 250                 255

Gln Glu Glu Glu Met Lys Thr Glu Asp Glu Ala Glu Met Ser Lys
            260                 265                 270

Ser Asp His Val Arg Lys Gln Arg Thr Asp Asp Leu Leu Gly Trp
        275                 280                 285

Val Leu Lys His Ser Asn Leu Ser Thr Glu Gln Ile Leu Asp Leu Ile
290                 295                 300

Leu Ser Leu Leu Phe Ala Gly His Glu Thr Ser Ser Val Ala Ile Ala
305                 310                 315                 320

Leu Ala Ile Phe Phe Leu Gln Ala Cys Pro Lys Ala Val Glu Glu Leu
                325                 330                 335

Arg Glu Glu His Leu Glu Ile Ala Arg Ala Lys Lys Glu Leu Gly Glu
            340                 345                 350

Ser Glu Leu Asn Trp Asp Asp Tyr Lys Lys Met Asp Phe Thr Gln Cys
        355                 360                 365

Val Ile Asn Glu Thr Leu Arg Leu Gly Asn Val Val Arg Phe Leu His
370                 375                 380

Arg Lys Ala Leu Lys Asp Val Arg Tyr Lys Gly Tyr Asp Ile Pro Ser
385                 390                 395                 400

Gly Trp Lys Val Leu Pro Val Ile Ser Ala Val His Leu Asp Asn Ser
                405                 410                 415

Arg Tyr Asp Gln Pro Asn Leu Phe Asn Pro Trp Arg Trp Gln Gln Gln
            420                 425                 430

Asn Asn Gly Ala Ser Ser Ser Gly Ser Gly Ser Phe Ser Thr Trp Gly
        435                 440                 445

Asn Asn Tyr Met Pro Phe Gly Gly Gly Pro Arg Leu Cys Ala Gly Ser
450                 455                 460

Glu Leu Ala Lys Leu Glu Met Ala Val Phe Ile His His Leu Val Leu
465                 470                 475                 480

Lys Phe Asn Trp Glu Leu Ala Glu Asp Gln Pro Phe Ala Phe Pro
                485                 490                 495

Phe Val Asp Phe Pro Asn Gly Leu Pro Ile Arg Val Ser Arg Ile Leu
            500                 505                 510

<210> SEQ ID NO 26
<211> LENGTH: 512
<212> TYPE: PRT
<213> ORGANISM: Artificial Sequence
<220> FEATURE:
<221> NAME/KEY: misc_feature
<222> LOCATION: (1)..(512)
```

<223> OTHER INFORMATION: Ortholog_#5_to_At_DWF4

<400> SEQUENCE: 26

```
Met Phe Glu Thr Glu His His Thr Val Leu Pro Leu Leu Pro Ser
1               5                   10                  15

Leu Leu Ser Leu Leu Phe Leu Ile Leu Val Lys Arg Arg Asn Arg
            20                  25                  30

Lys Thr Arg Phe Asn Leu Pro Pro Gly Lys Ser Gly Trp Pro Phe Leu
        35                  40                  45

Gly Glu Thr Ile Gly Tyr Pro Lys Pro Tyr Thr Ala Thr Thr Leu Gly
    50                  55                  60

Asp Phe Met Gln Gln His Val Ser Lys Tyr Gly Lys Ile Tyr Arg Ser
65                  70                  75                  80

Asn Leu Phe Gly Glu Pro Thr Ile Val Ser Ala Asp Ala Gly Leu Asn
                85                  90                  95

Arg Phe Ile Leu Gln Asn Glu Gly Arg Leu Phe Glu Cys Ser Tyr Pro
            100                 105                 110

Arg Ser Ile Gly Gly Ile Leu Gly Lys Trp Ser Met Leu Val Leu Val
        115                 120                 125

Gly Asp Met His Arg Asp Met Arg Ser Ile Ser Leu Asn Phe Leu Ser
130                 135                 140

His Ala Arg Leu Arg Thr Ile Leu Leu Lys Asp Val Glu Arg His Thr
145                 150                 155                 160

Leu Phe Val Leu Asp Ser Trp Gln Gln Asn Ser Ile Phe Ser Ala Arg
                165                 170                 175

Asp Glu Ala Lys Lys Phe Thr Phe Asn Leu Met Ala Lys His Ile Met
            180                 185                 190

Ser Met Asp Pro Gly Glu Glu Glu Thr Glu Gln Leu Lys Lys Glu Tyr
        195                 200                 205

Val Thr Phe Met Lys Gly Val Val Ser Ala Pro Leu Asn Leu Pro Gly
    210                 215                 220

Thr Ala Tyr His Lys Ala Leu Gln Ser Arg Ala Thr Ile Leu Lys Phe
225                 230                 235                 240

Ile Glu Arg Lys Met Glu Glu Arg Lys Leu Asp Ile Lys Glu Glu Asp
                245                 250                 255

Gln Glu Glu Glu Glu Met Lys Thr Glu Asp Glu Ala Glu Met Ser Lys
            260                 265                 270

Ser Asp His Ile Arg Lys Gln Arg Thr Asp Asp Leu Leu Gly Trp
        275                 280                 285

Val Leu Lys His Ser Asn Leu Ser Thr Glu Gln Ile Leu Asp Leu Ile
    290                 295                 300

Leu Ser Leu Leu Phe Ala Gly His Glu Thr Ser Ser Val Ala Ile Ala
305                 310                 315                 320

Leu Ala Ile Phe Phe Leu Gln Ala Cys Pro Lys Ala Val Glu Glu Leu
                325                 330                 335

Arg Glu Glu His Leu Glu Ile Ala Arg Ala Lys Lys Glu Leu Gly Glu
            340                 345                 350

Ser Glu Leu Asn Trp Asp Asp Tyr Lys Lys Met Asp Phe Thr Gln Cys
        355                 360                 365

Val Ile Asn Glu Thr Leu Arg Leu Gly Asn Val Arg Phe Leu His
    370                 375                 380

Arg Lys Ala Leu Lys Asp Val Arg Tyr Lys Gly Tyr Asp Ile Pro Ser
385                 390                 395                 400

Gly Trp Lys Val Leu Pro Val Ile Ser Ala Val His Leu Asp Asn Ser
```

```
                    405                 410                 415
Arg Tyr Asp Gln Pro Asn Leu Phe Asn Pro Trp Arg Trp Gln Gln Gln
                420                 425                 430

Asn Asn Gly Ala Ser Ser Gly Ser Gly Ser Phe Ser Thr Trp Gly
            435                 440                 445

Asn Asn Tyr Met Pro Phe Gly Gly Pro Arg Leu Cys Ala Gly Ser
        450                 455                 460

Glu Leu Ala Lys Leu Glu Met Ala Val Phe Ile His His Leu Val Leu
465                 470                 475                 480

Lys Phe Asn Trp Glu Leu Ala Glu Asp Gln Pro Phe Ala Phe Pro
                485                 490                 495

Phe Val Asp Phe Pro Asn Gly Leu Pro Ile Arg Val Ser Arg Ile Leu
                500                 505                 510

<210> SEQ ID NO 27
<211> LENGTH: 512
<212> TYPE: PRT
<213> ORGANISM: Artificial Sequence
<220> FEATURE:
<221> NAME/KEY: misc_feature
<222> LOCATION: (1)..(512)
<223> OTHER INFORMATION: Ortholog_#6_to_At_DWF4

<400> SEQUENCE: 27

Met Phe Glu Thr Glu His His Thr Val Leu Pro Leu Leu Leu Pro Ser
1               5                   10                  15

Leu Leu Ser Leu Leu Leu Phe Leu Ile Leu Val Lys Arg Arg Asn Arg
                20                  25                  30

Lys Thr Arg Phe Asn Leu Pro Pro Gly Lys Ser Gly Trp Pro Phe Leu
            35                  40                  45

Gly Glu Thr Ile Gly Tyr Pro Lys Pro Tyr Thr Ala Thr Thr Leu Gly
        50                  55                  60

Asp Phe Met Gln Gln His Val Ser Lys Tyr Gly Lys Ile Tyr Arg Ser
65                  70                  75                  80

Asn Leu Phe Gly Glu Pro Thr Ile Val Ser Ala Asp Ala Gly Leu Asn
                85                  90                  95

Arg Phe Ile Leu Gln Asn Glu Gly Arg Leu Phe Glu Cys Ser Tyr Pro
            100                 105                 110

Arg Ser Ile Gly Gly Ile Leu Gly Lys Trp Ser Met Leu Val Leu Val
        115                 120                 125

Gly Asp Met His Arg Asp Met Arg Ser Ile Ser Leu Asn Phe Leu Ser
130                 135                 140

His Ala Arg Leu Arg Thr Ile Leu Leu Lys Asp Val Glu Arg His Thr
145                 150                 155                 160

Leu Phe Val Leu Asp Ser Trp Gln Gln Asn Ser Ile Phe Ser Ala Arg
                165                 170                 175

Asp Glu Ala Lys Lys Phe Thr Phe Asn Leu Met Ala Lys His Ile Met
            180                 185                 190

Ser Met Asp Pro Gly Glu Glu Glu Thr Glu Gln Leu Lys Lys Glu Tyr
        195                 200                 205

Val Thr Phe Met Lys Gly Val Val Ser Ala Pro Leu Asn Leu Pro Gly
    210                 215                 220

Thr Ala Tyr His Lys Ala Leu Gln Ser Arg Ala Thr Ile Leu Lys Phe
225                 230                 235                 240

Ile Glu Arg Lys Met Glu Glu Arg Lys Leu Asp Ile Lys Glu Glu Asp
                245                 250                 255
```

```
Gln Glu Glu Glu Met Lys Thr Glu Asp Glu Ala Glu Met Ser Lys
            260                 265                 270

Ser Asp His Ile Arg Lys Gln Arg Thr Asp Asp Leu Leu Gly Trp
        275                 280                 285

Val Leu Lys His Ser Asn Leu Ser Thr Glu Gln Ile Leu Asp Leu Ile
        290                 295                 300

Leu Ser Leu Leu Phe Ala Gly His Glu Thr Ser Ser Val Ala Ile Ala
305                 310                 315                 320

Leu Ala Ile Phe Phe Leu Gln Ala Cys Pro Lys Ala Val Glu Glu Leu
                325                 330                 335

Arg Glu Glu His Leu Glu Ile Ala Arg Ala Lys Lys Glu Leu Gly Glu
                340                 345                 350

Ser Glu Leu Asn Trp Asp Asp Tyr Lys Lys Met Asp Phe Thr Gln Cys
            355                 360                 365

Val Ile Asn Glu Thr Leu Arg Leu Gly Asn Val Val Arg Phe Leu His
        370                 375                 380

Arg Lys Ala Leu Lys Asp Val Arg Tyr Lys Gly Tyr Asp Ile Pro Ser
385                 390                 395                 400

Gly Trp Lys Val Leu Pro Val Ile Ser Ala Val His Leu Asp Asn Ser
                405                 410                 415

Arg Tyr Asp Gln Pro Asn Leu Phe Asn Pro Trp Arg Trp Gln Gln Gln
                420                 425                 430

Asn Asn Gly Ala Ser Ser Ser Gly Ser Gly Ser Phe Ser Thr Trp Gly
            435                 440                 445

Asn Asn Tyr Met Pro Phe Gly Gly Pro Arg Leu Cys Ala Gly Ser
            450                 455                 460

Glu Leu Ala Lys Leu Glu Met Ala Val Phe Ile His His Leu Val Leu
465                 470                 475                 480

Lys Phe Asn Trp Glu Leu Ala Glu Asp Asp Gln Pro Phe Ala Phe Pro
                485                 490                 495

Phe Val Asp Phe Pro Asn Gly Leu Pro Ile Arg Val Ser Arg Ile Val
                500                 505                 510

<210> SEQ ID NO 28
<211> LENGTH: 485
<212> TYPE: PRT
<213> ORGANISM: Artificial Sequence
<220> FEATURE:
<221> NAME/KEY: misc_feature
<222> LOCATION: (1)..(485)
<223> OTHER INFORMATION: Ortholog_#1_to_Zm_DWF4

<400> SEQUENCE: 28

Met Met Met Met Ile Met Ala Gly Glu His Val Leu Ala Ala Leu Gly
1               5                   10                  15

Thr Leu Leu Leu Ala Ser Leu Leu Thr Leu Val Leu Asn His Phe Leu
            20                  25                  30

Pro Leu Leu Leu Asn Pro Lys Ala Pro Arg Gly Ser Phe Gly Trp Pro
        35                  40                  45

Leu Leu Gly Glu Thr Leu Arg Phe Leu Thr Pro His Ala Ser Asn Thr
    50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
                85                  90                  95

Leu Asn His Phe Ile Leu Gln Asn Glu Glu Arg Leu Phe Gln Cys Ser
            100                 105                 110
```

Tyr Pro Arg Pro Ile His Gly Ile Leu Gly Lys Ser Ser Met Leu Val
            115                 120                 125

Val Leu Gly Glu Asp His Lys Arg Leu Arg Asn Leu Ala Leu Ala Leu
130                 135                 140

Val Thr Ser Thr Lys Leu Lys Pro Ser Tyr Leu Gly Asp Ile Glu Lys
145                 150                 155                 160

Ile Ala Leu His Val Val Gly Ala Trp Arg Arg His Gly Ser Ser Gly
            165                 170                 175

Gly Val Arg Val Val Ala Phe Cys Glu Glu Ala Arg Lys Phe Ala Phe
            180                 185                 190

Ser Val Ile Val Lys Gln Val Leu Gly Leu Ser Pro Glu Glu Pro Val
            195                 200                 205

Thr Ala Arg Ile Leu Glu Asp Phe Leu Ala Phe Met Lys Gly Leu Ile
210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
            245                 250                 255

Arg Ser Ala Gly Ser Trp Asn Lys Gln Gly Asp Phe Leu Asp Val Leu
            260                 265                 270

Leu Ser Ser Asn Glu Leu Ser Asp Glu Glu Lys Val Ser Phe Val Leu
            275                 280                 285

Asp Ser Leu Leu Gly Gly Tyr Glu Thr Thr Ser Leu Leu Ile Ser Met
290                 295                 300

Val Val Tyr Phe Leu Gly Gln Ser Ala Gln Asp Leu Asp Leu Val Lys
305                 310                 315                 320

Arg Glu His Asp Ser Ile Arg Ser Asn Lys Gly Lys Glu Glu Cys Leu
            325                 330                 335

Thr Ser Glu Asp Tyr Lys Lys Met Glu Tyr Thr Gln Gln Val Ile Asn
            340                 345                 350

Glu Ala Leu Arg Cys Gly Asn Ile Val Lys Phe Val His Arg Lys Ala
            355                 360                 365

Leu Lys Asp Val Lys Tyr Lys Glu Tyr Leu Ile Pro Ser Gly Trp Lys
            370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
            405                 410                 415

Thr Ser Lys Arg Phe Thr Pro Phe Gly Gly Gly Pro Arg Leu Cys Pro
            420                 425                 430

Gly Ser Glu Leu Ala Lys Val Glu Thr Ala Phe Phe Leu His His Leu
            435                 440                 445

Val Leu Asn Tyr Arg Trp Arg Ile Asp Gly Asp Asp Ile Pro Met Ala
450                 455                 460

Tyr Pro Tyr Val Glu Phe Gln Arg Gly Leu Pro Ile Glu Ile Glu Pro
465                 470                 475                 480

Thr Ser Pro Glu Ser

<210> SEQ ID NO 29
<211> LENGTH: 485
<212> TYPE: PRT
<213> ORGANISM: Artificial Sequence
<220> FEATURE:
<221> NAME/KEY: misc_feature
<222> LOCATION: (1)..(485)

<223> OTHER INFORMATION: Ortholog_#2_to_Zm_DWF4

<400> SEQUENCE: 29

```
Met Met Met Met Ile Met Ala Gly Glu His Val Leu Ala Ala Leu Gly
1               5                   10                  15

Thr Leu Leu Leu Ala Ser Leu Leu Thr Leu Val Leu Asn His Phe Val
            20                  25                  30

Pro Leu Leu Leu Asn Pro Lys Ala Pro Arg Gly Ser Phe Gly Trp Pro
        35                  40                  45

Leu Leu Gly Glu Thr Leu Arg Phe Leu Thr Pro His Ala Ser Asn Thr
    50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
                85                  90                  95

Leu Asn His Phe Ile Leu Gln Asn Glu Glu Arg Leu Phe Gln Cys Ser
            100                 105                 110

Tyr Pro Arg Pro Ile His Gly Ile Leu Gly Lys Ser Ser Met Leu Val
        115                 120                 125

Val Leu Gly Glu Asp His Lys Arg Leu Arg Asn Leu Ala Leu Ala Leu
    130                 135                 140

Val Thr Ser Thr Lys Leu Lys Pro Ser Tyr Leu Gly Asp Ile Glu Lys
145                 150                 155                 160

Ile Ala Leu His Val Val Gly Ala Trp Arg Arg His Gly Ser Ser Gly
                165                 170                 175

Gly Val Arg Val Val Ala Phe Cys Glu Glu Ala Arg Lys Phe Ala Phe
            180                 185                 190

Ser Val Ile Val Lys Gln Val Leu Gly Leu Ser Pro Glu Glu Pro Val
        195                 200                 205

Thr Ala Arg Ile Leu Glu Asp Phe Leu Ala Phe Met Lys Gly Leu Ile
    210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
                245                 250                 255

Arg Ser Ala Gly Ser Trp Asn Lys Gln Gly Asp Phe Leu Asp Val Leu
            260                 265                 270

Leu Ser Ser Asn Glu Leu Ser Asp Glu Glu Lys Val Ser Phe Val Leu
        275                 280                 285

Asp Ser Leu Leu Gly Gly Tyr Glu Thr Thr Ser Leu Leu Ile Ser Met
    290                 295                 300

Val Val Tyr Phe Leu Gly Gln Ser Ala Gln Asp Leu Asp Leu Val Lys
305                 310                 315                 320

Arg Glu His Asp Ser Ile Arg Ser Asn Lys Gly Lys Glu Glu Cys Leu
                325                 330                 335

Thr Ser Glu Asp Tyr Lys Lys Met Glu Tyr Thr Gln Gln Val Ile Asn
            340                 345                 350

Glu Ala Leu Arg Cys Gly Asn Ile Val Lys Phe Val His Arg Lys Ala
        355                 360                 365

Leu Lys Asp Val Lys Tyr Lys Gly Tyr Leu Ile Pro Ser Gly Trp Lys
    370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
```

```
                    405                 410                 415
Thr Ser Lys Arg Phe Thr Pro Phe Gly Gly Pro Arg Leu Cys Pro
            420                 425                 430

Gly Ser Glu Leu Ala Lys Val Glu Thr Ala Phe Phe Leu His His Leu
            435                 440                 445

Val Leu Asn Tyr Arg Trp Arg Ile Asp Gly Asp Asp Ile Pro Met Ala
            450                 455                 460

Tyr Pro Tyr Val Glu Phe Gln Arg Gly Leu Pro Ile Glu Ile Glu Pro
465                 470                 475                 480

Thr Ser Pro Glu Ser

<210> SEQ ID NO 30
<211> LENGTH: 485
<212> TYPE: PRT
<213> ORGANISM: Artificial Sequence
<220> FEATURE:
<221> NAME/KEY: misc_feature
<222> LOCATION: (1)..(485)
<223> OTHER INFORMATION: Ortholog_#3_to_Zm_DWF4

<400> SEQUENCE: 30

Met Met Met Met Ile Met Ala Gly Glu His Val Leu Ala Ala Leu Gly
1               5                   10                  15

Thr Leu Leu Leu Ala Ser Leu Leu Thr Leu Val Leu Asn His Phe Val
            20                  25                  30

Pro Val Leu Leu Asn Pro Lys Ala Pro Arg Gly Ser Phe Gly Trp Pro
        35                  40                  45

Leu Leu Gly Glu Thr Leu Arg Phe Leu Thr Pro His Ala Ser Asn Thr
50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
            85                  90                  95

Leu Asn His Phe Ile Leu Gln Asn Glu Glu Arg Leu Phe Gln Cys Ser
        100                 105                 110

Tyr Pro Arg Pro Ile His Gly Ile Leu Gly Lys Ser Ser Met Leu Val
    115                 120                 125

Val Leu Gly Glu Asp His Lys Arg Leu Arg Asn Leu Ala Leu Ala Leu
130                 135                 140

Val Thr Ser Thr Lys Leu Lys Pro Ser Tyr Leu Gly Asp Ile Glu Lys
145                 150                 155                 160

Ile Ala Leu His Val Val Gly Ala Trp Arg Arg His Gly Ser Ser Gly
            165                 170                 175

Gly Val Arg Val Val Ala Phe Cys Glu Glu Ala Arg Lys Phe Ala Phe
        180                 185                 190

Ser Val Ile Val Lys Gln Val Leu Gly Leu Ser Pro Glu Glu Pro Val
    195                 200                 205

Thr Ala Arg Ile Leu Glu Asp Phe Leu Ala Phe Met Lys Gly Leu Ile
210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
            245                 250                 255

Arg Ser Ala Gly Ser Trp Asn Lys Gln Gly Asp Phe Leu Asp Val Leu
        260                 265                 270

Leu Ser Ser Asn Glu Leu Ser Asp Glu Glu Lys Val Ser Phe Val Leu
```

```
                275                 280                 285
Asp Ser Leu Leu Gly Gly Tyr Glu Thr Thr Ser Leu Leu Ile Ser Met
        290                 295                 300

Val Val Tyr Phe Leu Gly Gln Ser Ala Gln Asp Leu Asp Leu Val Lys
305                 310                 315                 320

Arg Glu His Asp Ser Ile Arg Ser Asn Lys Gly Lys Glu Glu Cys Leu
                325                 330                 335

Thr Ser Glu Asp Tyr Lys Lys Met Glu Tyr Thr Gln Gln Val Ile Asn
            340                 345                 350

Glu Ala Leu Arg Cys Gly Asn Ile Val Lys Phe Val His Arg Lys Ala
        355                 360                 365

Leu Lys Asp Val Lys Tyr Lys Glu Tyr Leu Ile Pro Ser Gly Trp Lys
    370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
                405                 410                 415

Thr Ser Lys Arg Phe Thr Pro Phe Gly Gly Pro Arg Leu Cys Pro
            420                 425                 430

Gly Ser Glu Leu Ala Lys Val Glu Thr Ala Phe Phe Leu His His Leu
        435                 440                 445

Val Leu Asn Tyr Arg Trp Arg Ile Asp Gly Asp Ile Pro Met Ala
    450                 455                 460

Tyr Pro Tyr Val Glu Phe Gln Arg Gly Leu Pro Ile Glu Ile Glu Pro
465                 470                 475                 480

Thr Ser Pro Glu Ser

<210> SEQ ID NO 31
<211> LENGTH: 485
<212> TYPE: PRT
<213> ORGANISM: Artificial Sequence
<220> FEATURE:
<221> NAME/KEY: misc_feature
<222> LOCATION: (1)..(485)
<223> OTHER INFORMATION: Ortholog_#4_to_Zm_DWF4

<400> SEQUENCE: 31

Met Met Met Met Ile Met Ala Gly Glu His Val Leu Ala Ala Leu Gly
1               5                   10                  15

Thr Leu Leu Leu Ala Ser Leu Leu Thr Leu Val Leu Asn His Phe Val
            20                  25                  30

Pro Val Val Leu Asn Pro Lys Ala Pro Arg Gly Ser Phe Gly Trp Pro
        35                  40                  45

Leu Leu Gly Glu Thr Leu Arg Phe Leu Thr Pro His Ala Ser Asn Thr
    50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
                85                  90                  95

Leu Asn His Phe Ile Leu Gln Asn Glu Glu Arg Leu Phe Gln Cys Ser
            100                 105                 110

Tyr Pro Arg Pro Ile His Gly Ile Leu Gly Lys Ser Ser Met Leu Val
        115                 120                 125

Val Leu Gly Glu Asp His Lys Arg Leu Arg Asn Leu Ala Leu Ala Leu
    130                 135                 140

Val Thr Ser Thr Lys Leu Lys Pro Ser Tyr Leu Gly Asp Ile Glu Lys
```

```
                145                 150                 155                 160
Ile Ala Leu His Val Val Gly Ala Trp Arg Arg His Gly Ser Ser Gly
            165                 170                 175

Gly Val Arg Val Val Ala Phe Cys Glu Glu Ala Arg Lys Phe Ala Phe
            180                 185                 190

Ser Val Ile Val Lys Gln Val Leu Gly Leu Ser Pro Glu Pro Val
            195                 200                 205

Thr Ala Arg Ile Leu Glu Asp Phe Leu Ala Phe Met Lys Gly Leu Ile
            210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
            245                 250                 255

Arg Ser Ala Gly Ser Trp Asn Lys Gln Gly Asp Phe Leu Asp Val Leu
            260                 265                 270

Leu Ser Ser Asn Glu Leu Ser Asp Glu Lys Val Ser Phe Val Leu
            275                 280                 285

Asp Ser Leu Leu Gly Gly Tyr Glu Thr Thr Ser Leu Leu Ile Ser Met
            290                 295                 300

Val Val Tyr Phe Leu Gly Gln Ser Ala Gln Asp Leu Asp Leu Val Lys
305                 310                 315                 320

Arg Glu His Asp Ser Ile Arg Ser Asn Lys Gly Lys Glu Glu Cys Leu
            325                 330                 335

Thr Ser Glu Asp Tyr Lys Lys Met Glu Tyr Thr Gln Gln Val Ile Asn
            340                 345                 350

Glu Ala Leu Arg Cys Gly Asn Ile Val Lys Phe Val His Arg Lys Ala
            355                 360                 365

Leu Lys Asp Val Lys Tyr Lys Glu Tyr Leu Ile Pro Ser Gly Trp Lys
            370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
            405                 410                 415

Thr Ser Lys Arg Phe Thr Pro Phe Gly Gly Pro Arg Leu Cys Pro
            420                 425                 430

Gly Ser Glu Leu Ala Lys Val Glu Thr Ala Phe Phe Leu His His Leu
            435                 440                 445

Val Leu Asn Tyr Arg Trp Arg Ile Asp Gly Asp Asp Ile Pro Met Ala
            450                 455                 460

Tyr Pro Tyr Val Glu Phe Gln Arg Gly Leu Pro Ile Glu Ile Glu Pro
465                 470                 475                 480

Thr Ser Pro Glu Ser

<210> SEQ ID NO 32
<211> LENGTH: 485
<212> TYPE: PRT
<213> ORGANISM: Artificial Sequence
<220> FEATURE:
<221> NAME/KEY: misc_feature
<222> LOCATION: (1)..(485)
<223> OTHER INFORMATION: Ortholog_#5_to_Zm_DWF4

<400> SEQUENCE: 32

Met Met Met Met Ile Met Ala Gly Glu His Val Leu Ala Ala Leu Gly
1               5                   10                  15

Thr Leu Leu Leu Ala Ser Leu Leu Thr Leu Val Leu Asn His Phe Val
```

```
                  20                  25                  30
Pro Val Val Leu Asn Pro Lys Ala Pro Arg Gly Ser Phe Gly Trp Pro
            35                  40                  45

Leu Leu Gly Glu Thr Leu Arg Phe Leu Thr Pro His Ala Ser Asn Thr
    50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
                85                  90                  95

Leu Asn His Phe Ile Leu Gln Asn Glu Glu Arg Leu Phe Gln Cys Ser
            100                 105                 110

Tyr Pro Arg Pro Ile His Gly Ile Leu Gly Lys Ser Ser Met Leu Val
                115                 120                 125

Val Leu Gly Glu Asp His Lys Arg Leu Arg Asn Leu Ala Leu Ala Leu
            130                 135                 140

Val Thr Ser Thr Lys Leu Lys Pro Ser Tyr Leu Gly Asp Ile Glu Lys
145                 150                 155                 160

Ile Ala Leu His Val Val Gly Ala Trp Arg Arg His Gly Ser Ser Gly
                165                 170                 175

Gly Ile Arg Val Val Ala Phe Cys Glu Glu Ala Arg Lys Phe Ala Phe
                180                 185                 190

Ser Val Ile Val Lys Gln Val Leu Gly Leu Ser Pro Glu Glu Pro Val
            195                 200                 205

Thr Ala Arg Ile Leu Glu Asp Phe Leu Ala Phe Met Lys Gly Leu Ile
            210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
                245                 250                 255

Arg Ser Ala Gly Ser Trp Asn Lys Gln Gly Asp Phe Leu Asp Val Leu
                260                 265                 270

Leu Ser Ser Asn Glu Leu Ser Asp Glu Glu Lys Val Ser Phe Val Leu
            275                 280                 285

Asp Ser Leu Leu Gly Gly Tyr Glu Thr Thr Ser Leu Leu Ile Ser Met
            290                 295                 300

Val Val Tyr Phe Leu Gly Gln Ser Ala Gln Asp Leu Asp Leu Val Lys
305                 310                 315                 320

Arg Glu His Asp Ser Ile Arg Ser Asn Lys Gly Lys Glu Glu Cys Leu
                325                 330                 335

Thr Ser Glu Asp Tyr Lys Lys Met Glu Tyr Thr Gln Gln Val Ile Asn
                340                 345                 350

Glu Ala Leu Arg Cys Gly Asn Ile Val Lys Phe Val His Arg Lys Ala
            355                 360                 365

Leu Lys Asp Val Lys Tyr Lys Gly Tyr Leu Ile Pro Ser Gly Trp Lys
            370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
                405                 410                 415

Thr Ser Lys Arg Phe Thr Pro Phe Gly Gly Pro Arg Leu Cys Pro
                420                 425                 430

Gly Ser Glu Leu Ala Lys Val Glu Thr Ala Phe Phe Leu His His Leu
            435                 440                 445
```

```
Val Leu Asn Tyr Arg Trp Arg Ile Asp Gly Asp Ile Pro Met Ala
    450                 455                 460

Tyr Pro Tyr Val Glu Phe Gln Arg Gly Leu Pro Ile Glu Ile Glu Pro
465                 470                 475                 480

Thr Ser Pro Glu Ser

<210> SEQ ID NO 33
<211> LENGTH: 485
<212> TYPE: PRT
<213> ORGANISM: Artificial Sequence
<220> FEATURE:
<221> NAME/KEY: misc_feature
<222> LOCATION: (1)..(485)
<223> OTHER INFORMATION: Ortholog_#6_to_Zm_DWF4

<400> SEQUENCE: 33

Met Met Met Met Ile Met Ala Gly Glu His Val Leu Ala Ala Leu Gly
1               5                   10                  15

Thr Leu Leu Leu Ala Ser Leu Leu Thr Leu Val Leu Asn His Phe Val
                20                  25                  30

Pro Val Val Leu Asn Pro Lys Ala Pro Arg Gly Ser Phe Gly Trp Pro
            35                  40                  45

Leu Leu Gly Glu Thr Leu Arg Phe Leu Thr Pro His Ala Ser Asn Thr
50                  55                  60

Leu Gly Gly Phe Leu Glu Asp His Cys Ser Arg Tyr Gly Arg Val Phe
65                  70                  75                  80

Lys Ser His Leu Phe Cys Thr Pro Thr Val Val Ser Cys Asp Gln Asp
                85                  90                  95

Leu Asn His Phe Ile Leu Gln Asn Glu Glu Arg Leu Phe Gln Cys Ser
            100                 105                 110

Tyr Pro Arg Pro Ile His Gly Ile Leu Gly Lys Ser Ser Met Leu Val
        115                 120                 125

Val Leu Gly Glu Asp His Lys Arg Leu Arg Asn Leu Ala Leu Ala Leu
130                 135                 140

Val Thr Ser Thr Lys Leu Lys Pro Ser Tyr Leu Gly Asp Ile Glu Lys
145                 150                 155                 160

Ile Ala Leu His Val Val Gly Ala Trp Arg Arg His Gly Ser Ser Gly
                165                 170                 175

Gly Ile Arg Val Val Ala Phe Cys Glu Ala Arg Lys Phe Ala Phe
            180                 185                 190

Ser Val Ile Val Lys Gln Val Leu Gly Leu Ser Pro Gly Glu Pro Val
        195                 200                 205

Thr Ala Arg Ile Leu Glu Asp Phe Leu Ala Phe Met Lys Gly Leu Ile
210                 215                 220

Ser Phe Pro Leu Tyr Ile Pro Gly Thr Pro Tyr Ala Lys Ala Val Arg
225                 230                 235                 240

Ala Arg Glu Arg Ile Ser Ser Thr Val Lys Gly Ile Ile Lys Glu Arg
                245                 250                 255

Arg Ser Ala Gly Ser Trp Asn Lys Gln Gly Asp Phe Leu Asp Val Leu
            260                 265                 270

Leu Ser Ser Asn Glu Leu Ser Asp Glu Glu Lys Val Ser Phe Val Leu
        275                 280                 285

Asp Ser Leu Leu Gly Gly Tyr Glu Thr Thr Ser Leu Leu Ile Ser Met
290                 295                 300

Val Val Tyr Phe Leu Gly Gln Ser Ala Gln Asp Leu Asp Leu Val Lys
305                 310                 315                 320
```

Arg Glu His Asp Ser Ile Arg Ser Asn Lys Gly Lys Glu Cys Leu
            325                 330                 335

Thr Ser Glu Asp Tyr Lys Lys Met Glu Tyr Thr Gln Gln Val Ile Asn
            340                 345                 350

Glu Ala Leu Arg Cys Gly Asn Ile Val Lys Phe Val His Arg Lys Ala
            355                 360                 365

Leu Lys Asp Val Lys Tyr Lys Glu Tyr Leu Ile Pro Ser Gly Trp Lys
            370                 375                 380

Val Leu Pro Val Phe Thr Ala Val His Leu Asn Pro Ser Leu His Gly
385                 390                 395                 400

Asp Ala Gln Gln Phe Gln Pro Cys Arg Trp Glu Gly Thr Ser Gln Gly
            405                 410                 415

Thr Ser Lys Arg Phe Thr Pro Phe Gly Gly Pro Arg Leu Cys Pro
            420                 425                 430

Gly Ser Glu Leu Ala Lys Val Glu Thr Ala Phe Phe Leu His His Leu
            435                 440                 445

Val Leu Asn Tyr Arg Trp Arg Ile Asp Gly Asp Ile Pro Met Ala
            450                 455                 460

Tyr Pro Tyr Val Glu Phe Gln Arg Gly Leu Pro Ile Glu Ile Glu Pro
465                 470                 475                 480

Thr Ser Pro Glu Ala

<210> SEQ ID NO 34
<211> LENGTH: 502
<212> TYPE: PRT
<213> ORGANISM: Artificial Sequence
<220> FEATURE:
<221> NAME/KEY: misc_feature
<222> LOCATION: (1)..(502)
<223> OTHER INFORMATION: Ortholog_#1_to_Os_DWF4

<400> SEQUENCE: 34

Met Ala Ser Ile Thr Ser Glu Val Leu Phe Leu Pro Phe Ile Leu
1               5                   10                  15

Leu Ala Leu Leu Thr Phe Tyr Thr Thr Thr Val Ala Lys Cys His Gly
            20                  25                  30

Gly His Trp Trp Arg Gly Gly Thr Thr Pro Ala Lys Arg Lys Arg Met
            35                  40                  45

Asn Leu Pro Pro Gly Ala Ala Gly Trp Pro Leu Val Gly Glu Thr Phe
50                  55                  60

Gly Tyr Leu Arg Ala His Pro Ala Thr Ser Val Gly Arg Phe Met Glu
65                  70                  75                  80

Gln His Ile Ala Arg Tyr Gly Lys Ile Tyr Arg Ser Ser Leu Phe Gly
            85                  90                  95

Glu Arg Thr Val Val Ser Ala Asp Ala Gly Leu Asn Arg Tyr Ile Leu
            100                 105                 110

Gln Asn Glu Gly Arg Leu Phe Glu Cys Ser Tyr Pro Arg Ser Ile Gly
            115                 120                 125

Gly Ile Leu Gly Lys Trp Ser Met Leu Val Leu Val Gly Asp Pro His
            130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
            165                 170                 175

Arg Ala Trp Leu Pro Ser Ser Thr Phe Ser Ala Gln His Gln Ala Lys
            180                 185                 190

```
Lys Phe Thr Phe Asn Leu Met Ala Lys Asn Ile Met Ser Met Asp Pro
        195                 200                 205
Gly Glu Glu Thr Glu Arg Leu Arg Arg Glu Tyr Ile Thr Phe Met
210                 215                 220
Lys Gly Val Val Ser Ala Pro Leu Asn Leu Pro Gly Thr Pro Tyr Trp
225                 230                 235                 240
Lys Ala Leu Lys Ser Arg Ala Ala Ile Leu Gly Val Ile Glu Arg Lys
                245                 250                 255
Met Glu Glu Arg Val Glu Lys Leu Ser Lys Glu Asp Ala Ser Val Glu
            260                 265                 270
Gln Asp Asp Leu Leu Gly Trp Ala Leu Lys Gln Ser Asn Leu Ser Lys
        275                 280                 285
Glu Gln Ile Leu Asp Leu Leu Leu Ser Leu Leu Phe Ala Gly His Glu
    290                 295                 300
Thr Ser Ser Met Ala Leu Ala Leu Ala Ile Phe Phe Leu Glu Gly Cys
305                 310                 315                 320
Pro Lys Ala Val Gln Glu Leu Arg Glu Glu His Leu Gly Ile Ala Arg
                325                 330                 335
Arg Gln Arg Leu Arg Gly Glu Cys Lys Leu Ser Trp Glu Asp Tyr Lys
            340                 345                 350
Glu Met Val Phe Thr Gln Cys Val Ile Asn Glu Thr Leu Arg Leu Gly
        355                 360                 365
Asn Val Val Arg Phe Leu His Arg Lys Val Ile Lys Asp Val His Tyr
    370                 375                 380
Lys Gly Tyr Asp Ile Pro Ser Gly Trp Lys Ile Leu Pro Val Leu Ala
385                 390                 395                 400
Ala Val His Leu Asp Ser Ser Leu Tyr Glu Asp Pro Gln Arg Phe Asn
                405                 410                 415
Pro Trp Arg Trp Lys Ser Ser Gly Ser Ser Gly Leu Ala Gln Ser
            420                 425                 430
Ser Ser Phe Met Pro Tyr Gly Gly Gly Thr Arg Leu Cys Ala Gly Ser
        435                 440                 445
Glu Leu Ala Lys Leu Glu Met Ala Val Phe Leu His His Leu Val Leu
    450                 455                 460
Asn Phe Arg Trp Glu Leu Ala Glu Pro Asp Gln Ala Phe Val Phe Pro
465                 470                 475                 480
Phe Val Asp Phe Pro Lys Gly Leu Pro Ile Arg Val His Arg Ile Ala
                485                 490                 495
Gln Asp Asp Glu Gln Glu

<210> SEQ ID NO 35
<211> LENGTH: 502
<212> TYPE: PRT
<213> ORGANISM: Artificial Sequence
<220> FEATURE:
<221> NAME/KEY: misc_feature
<222> LOCATION: (1)..(502)
<223> OTHER INFORMATION: Ortholog_#2_to_Os_DWF4

<400> SEQUENCE: 35

Met Ala Ser Ile Thr Ser Glu Val Val Phe Phe Leu Pro Phe Ile Leu
1               5                   10                  15
Leu Ala Leu Leu Thr Phe Tyr Thr Thr Thr Val Ala Lys Cys His Gly
            20                  25                  30
Gly His Trp Trp Arg Gly Gly Thr Thr Pro Ala Lys Arg Lys Arg Met
        35                  40                  45
```

```
Asn Leu Pro Pro Gly Ala Ala Gly Trp Pro Leu Val Gly Glu Thr Phe
 50                  55                  60

Gly Tyr Leu Arg Ala His Pro Ala Thr Ser Val Gly Arg Phe Met Glu
 65                  70                  75                  80

Gln His Ile Ala Arg Tyr Gly Lys Ile Tyr Arg Ser Ser Leu Phe Gly
                 85                  90                  95

Glu Arg Thr Val Val Ser Ala Asp Ala Gly Leu Asn Arg Tyr Ile Leu
            100                 105                 110

Gln Asn Glu Gly Arg Leu Phe Glu Cys Ser Tyr Pro Arg Ser Ile Gly
        115                 120                 125

Gly Ile Leu Gly Lys Trp Ser Met Leu Val Leu Gly Asp Pro His
    130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ala Trp Leu Pro Ser Ser Thr Phe Ser Ala Gln His Gln Ala Lys
                180                 185                 190

Lys Phe Thr Phe Asn Leu Met Ala Lys Asn Ile Met Ser Met Asp Pro
                195                 200                 205

Gly Glu Glu Glu Thr Glu Arg Leu Arg Arg Glu Tyr Ile Thr Phe Met
            210                 215                 220

Lys Gly Val Val Ser Ala Pro Leu Asn Leu Pro Gly Thr Pro Tyr Trp
225                 230                 235                 240

Lys Ala Leu Lys Ser Arg Ala Ala Ile Leu Gly Val Ile Glu Arg Lys
                245                 250                 255

Met Glu Glu Arg Val Glu Lys Leu Ser Lys Glu Asp Ala Ser Val Glu
            260                 265                 270

Gln Asp Asp Leu Leu Gly Trp Ala Leu Lys Gln Ser Asn Leu Ser Lys
        275                 280                 285

Glu Gln Ile Leu Asp Leu Leu Ser Leu Leu Phe Ala Gly His Glu
    290                 295                 300

Thr Ser Ser Met Ala Leu Ala Leu Ala Ile Phe Phe Leu Glu Gly Cys
305                 310                 315                 320

Pro Lys Ala Val Gln Glu Leu Arg Glu Glu His Leu Gly Ile Ala Arg
                325                 330                 335

Arg Gln Arg Leu Arg Gly Glu Cys Lys Leu Ser Trp Glu Asp Tyr Lys
            340                 345                 350

Glu Met Val Phe Thr Gln Cys Val Ile Asn Glu Thr Leu Arg Leu Gly
        355                 360                 365

Asn Val Val Arg Phe Leu His Arg Lys Val Ile Lys Asp Val His Tyr
    370                 375                 380

Lys Gly Tyr Asp Ile Pro Ser Gly Trp Lys Ile Leu Pro Val Leu Ala
385                 390                 395                 400

Ala Val His Leu Asp Ser Ser Leu Tyr Glu Asp Pro Gln Arg Phe Asn
                405                 410                 415

Pro Trp Arg Trp Lys Ser Ser Gly Ser Ser Gly Leu Ala Gln Ser
            420                 425                 430

Ser Ser Phe Met Pro Tyr Gly Gly Thr Arg Leu Cys Ala Gly Ser
        435                 440                 445

Glu Leu Ala Lys Leu Glu Met Ala Val Phe Leu His His Leu Val Leu
    450                 455                 460

Asn Phe Arg Trp Glu Leu Ala Glu Pro Asp Gln Ala Phe Val Phe Pro
465                 470                 475                 480
```

Phe Val Asp Phe Pro Lys Gly Leu Pro Ile Arg Val His Arg Ile Ala
                485                 490                 495

Gln Asp Asp Glu Gln Glu

<210> SEQ ID NO 36
<211> LENGTH: 502
<212> TYPE: PRT
<213> ORGANISM: Artificial Sequence
<220> FEATURE:
<221> NAME/KEY: misc_feature
<222> LOCATION: (1)..(502)
<223> OTHER INFORMATION: Ortholog_#3_to_Os_DWF4

<400> SEQUENCE: 36

Met Ala Ser Ile Thr Ser Glu Val Val Phe Leu Pro Phe Ile Leu
1               5                   10                  15

Leu Ala Leu Leu Thr Phe Tyr Thr Thr Thr Val Ala Lys Cys His Gly
                20                  25                  30

Gly His Trp Trp Arg Gly Gly Thr Thr Pro Ala Lys Arg Lys Arg Met
                35                  40                  45

Asn Leu Pro Pro Gly Ala Ala Gly Trp Pro Leu Val Gly Glu Thr Phe
50                  55                  60

Gly Tyr Leu Arg Ala His Pro Ala Thr Ser Val Gly Arg Phe Met Glu
65                  70                  75                  80

Gln His Ile Ala Arg Tyr Gly Lys Ile Tyr Arg Ser Ser Leu Phe Gly
                85                  90                  95

Glu Arg Thr Val Val Ser Ala Asp Ala Gly Leu Asn Arg Tyr Ile Leu
                100                 105                 110

Gln Asn Glu Gly Arg Leu Phe Glu Cys Ser Tyr Pro Arg Ser Ile Gly
                115                 120                 125

Gly Ile Leu Gly Lys Trp Ser Met Leu Val Leu Val Gly Asp Pro His
130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ala Trp Leu Pro Ser Ser Thr Phe Ser Ala Gln His Gln Ala Lys
                180                 185                 190

Lys Phe Thr Phe Asn Leu Met Ala Lys Asn Ile Met Ser Met Asp Pro
                195                 200                 205

Gly Glu Glu Thr Glu Arg Leu Arg Arg Glu Tyr Ile Thr Phe Met
210                 215                 220

Lys Gly Val Val Ser Ala Pro Leu Asn Leu Pro Gly Thr Pro Tyr Trp
225                 230                 235                 240

Lys Ala Leu Lys Ser Arg Ala Ala Ile Leu Gly Val Ile Glu Arg Lys
                245                 250                 255

Met Glu Glu Arg Val Glu Lys Val Ser Lys Glu Asp Ala Ser Val Glu
                260                 265                 270

Gln Asp Asp Leu Leu Gly Trp Ala Leu Lys Gln Ser Asn Leu Ser Lys
                275                 280                 285

Glu Gln Ile Leu Asp Leu Leu Leu Ser Leu Leu Phe Ala Gly His Glu
                290                 295                 300

Thr Ser Ser Met Ala Leu Ala Leu Ala Ile Phe Phe Leu Glu Gly Cys
305                 310                 315                 320

Pro Lys Ala Val Gln Glu Leu Arg Glu Glu His Leu Gly Ile Ala Arg
                325                 330                 335

```
Arg Gln Arg Leu Arg Gly Glu Cys Lys Leu Ser Trp Glu Asp Tyr Lys
            340                 345                 350

Glu Met Val Phe Thr Gln Cys Val Ile Asn Glu Thr Leu Arg Leu Gly
            355                 360                 365

Asn Val Val Arg Phe Leu His Arg Lys Val Ile Lys Asp Val His Tyr
            370                 375                 380

Lys Gly Tyr Asp Ile Pro Ser Gly Trp Lys Ile Leu Pro Val Leu Ala
385                 390                 395                 400

Ala Val His Leu Asp Ser Ser Leu Tyr Glu Asp Pro Gln Arg Phe Asn
                405                 410                 415

Pro Trp Arg Trp Lys Ser Ser Gly Ser Ser Gly Leu Ala Gln Ser
                420                 425                 430

Ser Ser Phe Met Pro Tyr Gly Gly Gly Thr Arg Leu Cys Ala Gly Ser
                435                 440                 445

Glu Leu Ala Lys Leu Glu Met Ala Val Phe Leu His His Leu Val Leu
    450                 455                 460

Asn Phe Arg Trp Glu Leu Ala Glu Pro Asp Gln Ala Phe Val Phe Pro
465                 470                 475                 480

Phe Val Asp Phe Pro Lys Gly Leu Pro Ile Arg Val His Arg Ile Ala
                485                 490                 495

Gln Asp Asp Glu Gln Glu

<210> SEQ ID NO 37
<211> LENGTH: 502
<212> TYPE: PRT
<213> ORGANISM: Artificial Sequence
<220> FEATURE:
<221> NAME/KEY: misc_feature
<222> LOCATION: (1)..(502)
<223> OTHER INFORMATION: Ortholog_#4_to_Os_DWF4

<400> SEQUENCE: 37

Met Ala Ser Ile Thr Ser Glu Val Val Phe Leu Pro Phe Ile Leu
1               5                   10                  15

Leu Ala Leu Leu Thr Phe Tyr Thr Thr Val Ala Lys Cys His Gly
                20                  25                  30

Gly His Trp Trp Arg Gly Gly Thr Thr Pro Ala Lys Arg Lys Arg Met
            35                  40                  45

Asn Leu Pro Pro Gly Ala Ala Gly Trp Pro Leu Val Gly Glu Thr Phe
    50                  55                  60

Gly Tyr Leu Arg Ala His Pro Ala Thr Ser Val Gly Arg Phe Met Glu
65                  70                  75                  80

Gln His Ile Ala Arg Tyr Gly Lys Ile Tyr Arg Ser Ser Leu Phe Gly
                85                  90                  95

Glu Arg Thr Val Val Ser Ala Asp Ala Gly Leu Asn Arg Tyr Ile Leu
            100                 105                 110

Gln Asn Glu Gly Arg Leu Phe Glu Cys Ser Tyr Pro Arg Ser Ile Gly
        115                 120                 125

Gly Ile Leu Gly Lys Trp Ser Met Leu Val Leu Val Gly Asp Pro His
    130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ala Trp Leu Pro Ser Ser Thr Phe Ser Ala Gln His Gln Ala Lys
            180                 185                 190
```

-continued

Lys Phe Thr Phe Asn Leu Met Ala Lys Asn Ile Met Ser Met Asp Pro
                195                 200                 205

Gly Glu Glu Thr Glu Arg Leu Arg Arg Glu Tyr Ile Thr Phe Met
    210                 215                 220

Lys Gly Val Val Ser Ala Pro Leu Asn Leu Pro Gly Thr Pro Tyr Trp
225                 230                 235                 240

Lys Ala Leu Lys Ser Arg Ala Ala Ile Leu Gly Val Ile Glu Arg Lys
                245                 250                 255

Met Glu Glu Arg Val Glu Lys Val Ser Lys Glu Asp Ala Ser Ile Glu
            260                 265                 270

Gln Asp Asp Leu Leu Gly Trp Ala Leu Lys Gln Ser Asn Leu Ser Lys
        275                 280                 285

Glu Gln Ile Leu Asp Leu Leu Ser Leu Phe Ala Gly His Glu
    290                 295                 300

Thr Ser Ser Met Ala Leu Ala Leu Ala Ile Phe Phe Leu Glu Gly Cys
305                 310                 315                 320

Pro Lys Ala Val Gln Glu Leu Arg Glu Glu His Leu Gly Ile Ala Arg
                325                 330                 335

Arg Gln Arg Leu Arg Gly Glu Cys Lys Leu Ser Trp Glu Asp Tyr Lys
            340                 345                 350

Glu Met Val Phe Thr Gln Cys Val Ile Asn Glu Thr Leu Arg Leu Gly
        355                 360                 365

Asn Val Val Arg Phe Leu His Arg Lys Val Ile Lys Asp Val His Tyr
370                 375                 380

Lys Gly Tyr Asp Ile Pro Ser Gly Trp Lys Ile Leu Pro Val Leu Ala
385                 390                 395                 400

Ala Val His Leu Asp Ser Ser Leu Tyr Glu Asp Pro Gln Arg Phe Asn
                405                 410                 415

Pro Trp Arg Trp Lys Ser Ser Gly Ser Ser Gly Gly Leu Ala Gln Ser
            420                 425                 430

Ser Ser Phe Met Pro Tyr Gly Gly Thr Arg Leu Cys Ala Gly Ser
        435                 440                 445

Glu Leu Ala Lys Leu Glu Met Ala Val Phe Leu His His Leu Val Leu
    450                 455                 460

Asn Phe Arg Trp Glu Leu Ala Glu Pro Asp Gln Ala Phe Val Phe Pro
465                 470                 475                 480

Phe Val Asp Phe Pro Lys Gly Leu Pro Ile Arg Val His Arg Ile Ala
                485                 490                 495

Gln Asp Asp Glu Gln Glu

<210> SEQ ID NO 38
<211> LENGTH: 502
<212> TYPE: PRT
<213> ORGANISM: Artificial Sequence
<220> FEATURE:
<221> NAME/KEY: misc_feature
<222> LOCATION: (1)..(502)
<223> OTHER INFORMATION: Ortholog_#5_to_Os_DWF4

<400> SEQUENCE: 38

Met Ala Ser Ile Thr Ser Glu Val Val Phe Phe Leu Pro Phe Ile Leu
1               5                   10                  15

Leu Ala Leu Leu Thr Phe Tyr Thr Thr Thr Val Ala Lys Cys His Gly
            20                  25                  30

Gly His Trp Trp Arg Gly Gly Thr Thr Pro Ala Lys Arg Lys Arg Met
        35                  40                  45

```
Asn Leu Pro Pro Gly Ala Ala Gly Trp Pro Leu Val Gly Glu Thr Phe
     50                  55                  60

Gly Tyr Leu Arg Ala His Pro Ala Thr Ser Val Gly Arg Phe Met Glu
 65                  70                  75                  80

Gln His Ile Ala Arg Tyr Gly Lys Ile Tyr Arg Ser Ser Leu Phe Gly
                 85                  90                  95

Glu Arg Thr Val Val Ser Ala Asp Ala Gly Leu Asn Arg Tyr Ile Leu
                100                 105                 110

Gln Asn Glu Gly Arg Leu Phe Glu Cys Ser Tyr Pro Arg Ser Ile Gly
            115                 120                 125

Gly Ile Leu Gly Lys Trp Ser Met Leu Val Leu Val Gly Asp Pro His
        130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ala Trp Leu Pro Ser Ser Thr Phe Ser Ala Gln His Gln Ala Lys
            180                 185                 190

Lys Phe Thr Phe Asn Leu Met Ala Lys Asn Ile Met Ser Met Asp Pro
        195                 200                 205

Gly Glu Glu Thr Glu Arg Leu Arg Arg Glu Tyr Ile Thr Phe Met
210                 215                 220

Lys Gly Val Val Ser Ala Pro Leu Asn Leu Pro Gly Thr Pro Tyr Trp
225                 230                 235                 240

Lys Ala Leu Lys Ser Arg Ala Ala Ile Leu Gly Val Ile Glu Arg Lys
                245                 250                 255

Met Glu Glu Arg Val Glu Lys Val Ser Lys Glu Asp Ala Ser Ile Glu
            260                 265                 270

Gln Asp Asp Leu Leu Gly Trp Ala Leu Lys Gln Ser Asn Leu Ser Lys
        275                 280                 285

Glu Gln Ile Leu Asp Leu Leu Leu Ser Leu Leu Phe Ala Gly His Glu
    290                 295                 300

Thr Ser Ser Met Ala Leu Ala Leu Ala Ile Phe Phe Leu Glu Gly Cys
305                 310                 315                 320

Pro Lys Ala Val Gln Glu Leu Arg Glu Glu His Leu Gly Ile Ala Arg
                325                 330                 335

Arg Gln Arg Val Arg Gly Glu Cys Lys Leu Ser Trp Glu Asp Tyr Lys
            340                 345                 350

Glu Met Val Phe Thr Gln Cys Val Ile Asn Glu Thr Leu Arg Leu Gly
        355                 360                 365

Asn Val Val Arg Phe Leu His Arg Lys Val Ile Lys Asp Val His Tyr
    370                 375                 380

Lys Gly Tyr Asp Ile Pro Ser Gly Trp Lys Ile Leu Pro Val Leu Ala
385                 390                 395                 400

Ala Val His Leu Asp Ser Ser Leu Tyr Glu Asp Pro Gln Arg Phe Asn
                405                 410                 415

Pro Trp Arg Trp Lys Ser Ser Gly Ser Ser Gly Leu Ala Gln Ser
            420                 425                 430

Ser Ser Phe Met Pro Tyr Gly Gly Thr Arg Leu Cys Ala Gly Ser
        435                 440                 445

Glu Leu Ala Lys Leu Glu Met Ala Val Phe Leu His His Leu Val Leu
    450                 455                 460

Asn Phe Arg Trp Glu Leu Ala Glu Pro Asp Gln Ala Phe Val Phe Pro
```

-continued

```
              465                 470                 475                 480

Phe Val Asp Phe Pro Lys Gly Leu Pro Ile Arg Val His Arg Ile Ala
                    485                 490                 495

Gln Asp Asp Glu Gln Glu

<210> SEQ ID NO 39
<211> LENGTH: 502
<212> TYPE: PRT
<213> ORGANISM: Artificial Sequence
<220> FEATURE:
<221> NAME/KEY: misc_feature
<222> LOCATION: (1)..(502)
<223> OTHER INFORMATION: Ortholog_#6_to_Os_DWF4

<400> SEQUENCE: 39

Met Ala Ser Ile Thr Ser Glu Val Val Phe Phe Leu Pro Phe Ile Leu
1               5                   10                  15

Leu Ala Leu Leu Thr Phe Tyr Thr Thr Thr Val Ala Lys Cys His Gly
                20                  25                  30

Gly His Trp Trp Arg Gly Gly Thr Thr Pro Ala Lys Arg Lys Arg Met
            35                  40                  45

Asn Leu Pro Pro Gly Ala Ala Gly Trp Pro Leu Val Gly Glu Thr Phe
50                  55                  60

Gly Tyr Leu Arg Ala His Pro Ala Thr Ser Val Gly Arg Phe Met Glu
65                  70                  75                  80

Gln His Ile Ala Arg Tyr Gly Lys Ile Tyr Arg Ser Ser Leu Phe Gly
                85                  90                  95

Glu Arg Thr Val Val Ser Ala Asp Ala Gly Leu Asn Arg Tyr Ile Leu
            100                 105                 110

Gln Asn Glu Gly Arg Leu Phe Glu Cys Ser Tyr Pro Arg Ser Ile Gly
        115                 120                 125

Gly Ile Leu Gly Lys Trp Ser Met Leu Val Leu Val Gly Asp Pro His
    130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ala Trp Leu Pro Ser Ser Thr Phe Ser Ala Gln His Gln Ala Lys
            180                 185                 190

Lys Phe Thr Phe Asn Leu Met Ala Lys Asn Ile Met Ser Met Asp Pro
        195                 200                 205

Gly Glu Glu Glu Thr Glu Arg Leu Arg Arg Glu Tyr Ile Thr Phe Met
    210                 215                 220

Lys Gly Val Val Ser Ala Pro Leu Asn Leu Pro Gly Thr Pro Tyr Trp
225                 230                 235                 240

Lys Ala Leu Lys Ser Arg Ala Ala Ile Leu Gly Val Ile Glu Arg Lys
                245                 250                 255

Met Glu Glu Arg Val Glu Lys Val Ser Lys Glu Asp Ala Ser Ile Glu
            260                 265                 270

Gln Asp Asp Leu Leu Gly Trp Ala Leu Lys Gln Ser Asn Leu Ser Lys
        275                 280                 285

Glu Gln Ile Leu Asp Leu Leu Ser Leu Phe Ala Gly His Glu
    290                 295                 300

Thr Ser Ser Met Ala Leu Ala Leu Ala Ile Phe Phe Leu Glu Gly Cys
305                 310                 315                 320

Pro Lys Ala Val Gln Glu Leu Arg Glu Glu His Leu Gly Ile Ala Arg
```

```
                        325                 330                 335
Arg Gln Arg Val Arg Gly Glu Cys Lys Leu Ser Trp Glu Asp Tyr Lys
                340                 345                 350

Glu Met Val Phe Thr Gln Cys Val Ile Asn Glu Thr Leu Arg Leu Gly
            355                 360                 365

Asn Val Val Arg Phe Leu His Arg Lys Val Ile Lys Asp Val His Tyr
        370                 375                 380

Lys Gly Tyr Asp Ile Pro Ser Gly Trp Lys Ile Leu Pro Val Leu Ala
385                 390                 395                 400

Ala Val His Leu Asp Ser Ser Leu Tyr Glu Asp Pro Gln Arg Phe Asn
                405                 410                 415

Pro Trp Arg Trp Lys Ser Ser Gly Ser Ser Gly Leu Ala Gln Ser
            420                 425                 430

Ser Ser Phe Met Pro Tyr Gly Gly Thr Arg Leu Cys Ala Gly Ser
        435                 440                 445

Glu Leu Ala Lys Leu Glu Met Ala Val Phe Leu His His Leu Val Leu
450                 455                 460

Asn Phe Arg Trp Glu Leu Ala Glu Pro Asp Gln Ala Phe Val Phe Pro
465                 470                 475                 480

Phe Val Asp Phe Pro Lys Gly Leu Pro Ile Arg Val His Arg Leu Ala
                485                 490                 495

Gln Asp Asp Glu Gln Glu

<210> SEQ ID NO 40
<211> LENGTH: 502
<212> TYPE: PRT
<213> ORGANISM: Oryza sativa

<400> SEQUENCE: 40

Met Ala Ser Ile Thr Ser Glu Leu Leu Phe Phe Leu Pro Phe Ile Leu
1               5                   10                  15

Leu Ala Leu Leu Thr Phe Tyr Thr Thr Thr Val Ala Lys Cys His Gly
            20                  25                  30

Gly His Trp Trp Arg Gly Gly Thr Thr Pro Ala Lys Arg Lys Arg Met
        35                  40                  45

Asn Leu Pro Pro Gly Ala Ala Gly Trp Pro Leu Val Gly Glu Thr Phe
50                  55                  60

Gly Tyr Leu Arg Ala His Pro Ala Thr Ser Val Gly Arg Phe Met Glu
65                  70                  75                  80

Gln His Ile Ala Arg Tyr Gly Lys Ile Tyr Arg Ser Ser Leu Phe Gly
                85                  90                  95

Glu Arg Thr Val Val Ser Ala Asp Ala Gly Leu Asn Arg Tyr Ile Leu
            100                 105                 110

Gln Asn Glu Gly Arg Leu Phe Glu Cys Ser Tyr Pro Arg Ser Ile Gly
        115                 120                 125

Gly Ile Leu Gly Lys Trp Ser Met Leu Val Leu Val Gly Asp Pro His
130                 135                 140

Arg Glu Met Arg Ala Ile Ser Leu Asn Phe Leu Ser Ser Val Arg Leu
145                 150                 155                 160

Arg Ala Val Leu Leu Pro Glu Val Glu Arg His Thr Leu Leu Val Leu
                165                 170                 175

Arg Ala Trp Leu Pro Ser Ser Thr Phe Ser Ala Gln His Gln Ala Lys
            180                 185                 190

Lys Phe Thr Phe Asn Leu Met Ala Lys Asn Ile Met Ser Met Asp Pro
        195                 200                 205
```

Gly Glu Glu Glu Thr Glu Arg Leu Arg Arg Glu Tyr Ile Thr Phe Met
    210                 215                 220
Lys Gly Val Val Ser Ala Pro Leu Asn Leu Pro Gly Thr Pro Tyr Trp
225                 230                 235                 240
Lys Ala Leu Lys Ser Arg Ala Ala Ile Leu Gly Val Ile Glu Arg Lys
                245                 250                 255
Met Glu Glu Arg Val Glu Lys Leu Ser Lys Glu Asp Ala Ser Val Glu
            260                 265                 270
Gln Asp Asp Leu Leu Gly Trp Ala Leu Lys Gln Ser Asn Leu Ser Lys
        275                 280                 285
Glu Gln Ile Leu Asp Leu Leu Ser Leu Leu Phe Ala Gly His Glu
    290                 295                 300
Thr Ser Ser Met Ala Leu Ala Leu Ala Ile Phe Phe Leu Glu Gly Cys
305                 310                 315                 320
Pro Lys Ala Val Gln Glu Leu Arg Glu Glu His Leu Gly Ile Ala Arg
                325                 330                 335
Arg Gln Arg Leu Arg Gly Glu Cys Lys Leu Ser Trp Glu Asp Tyr Lys
            340                 345                 350
Glu Met Val Phe Thr Gln Cys Val Ile Asn Glu Thr Leu Arg Leu Gly
        355                 360                 365
Asn Val Val Arg Phe Leu His Arg Lys Val Ile Lys Asp Val His Tyr
    370                 375                 380
Lys Gly Tyr Asp Ile Pro Ser Gly Trp Lys Ile Leu Pro Val Leu Ala
385                 390                 395                 400
Ala Val His Leu Asp Ser Ser Leu Tyr Glu Asp Pro Gln Arg Phe Asn
                405                 410                 415
Pro Trp Arg Trp Lys Ser Ser Gly Ser Gly Gly Leu Ala Gln Ser Ser
            420                 425                 430
Ser Phe Met Pro Tyr Gly Gly Gly Thr Arg Leu Cys Ala Gly Ser Glu
        435                 440                 445
Leu Ala Lys Glu Leu Glu Met Ala Val Phe Leu His Leu Val Leu
    450                 455                 460
Asn Phe Arg Trp Glu Leu Ala Glu Pro Asp Gln Ala Phe Val Phe Pro
465                 470                 475                 480
Phe Val Asp Phe Pro Lys Gly Leu Pro Ile Arg Val His Arg Ile Ala
                485                 490                 495
Gln Asp Asp Glu Gln Glu
            500

```
<210> SEQ ID NO 41
<211> LENGTH: 488
<212> TYPE: PRT
<213> ORGANISM: Artificial Sequence
<220> FEATURE:
<223> OTHER INFORMATION: Synthetic consensus sequence
<220> FEATURE:
<221> NAME/KEY: MOD_RES
<222> LOCATION: (2)..(2)
<223> OTHER INFORMATION: Phe or Met
<220> FEATURE:
<221> NAME/KEY: MOD_RES
<222> LOCATION: (3)..(3)
<223> OTHER INFORMATION: Glu or Met
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
```

```
<223> OTHER INFORMATION: Glu or Gly
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Thr or Val
<220> FEATURE:
<221> NAME/KEY: MOD_RES
<222> LOCATION: (10)..(10)
<223> OTHER INFORMATION: Leu or Ala
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid; This region may encompass 0-2
      residues
<220> FEATURE:
<221> NAME/KEY: MOD_RES
<222> LOCATION: (15)..(15)
<223> OTHER INFORMATION: Leu or Arg
<220> FEATURE:
<221> NAME/KEY: MOD_RES
<222> LOCATION: (16)..(16)
<223> OTHER INFORMATION: Leu or Ala
<220> FEATURE:
<221> NAME/KEY: MOD_RES
<222> LOCATION: (17)..(17)
<223> OTHER INFORMATION: Leu or Trp
<220> FEATURE:
<221> NAME/KEY: MOD_RES
<222> LOCATION: (18)..(18)
<223> OTHER INFORMATION: Pro or Ala
<220> FEATURE:
<221> NAME/KEY: MOD_RES
<222> LOCATION: (22)..(22)
<223> OTHER INFORMATION: Ala, Gly, Ser or Thr
<220> FEATURE:
<221> NAME/KEY: MOD_RES
<222> LOCATION: (24)..(24)
<223> OTHER INFORMATION: Ile, Val, Leu or Met
<220> FEATURE:
<221> NAME/KEY: MOD_RES
<222> LOCATION: (26)..(26)
<223> OTHER INFORMATION: Phe or Asn
<220> FEATURE:
<221> NAME/KEY: MOD_RES
<222> LOCATION: (27)..(27)
<223> OTHER INFORMATION: Leu or His
<220> FEATURE:
<221> NAME/KEY: MOD_RES
<222> LOCATION: (28)..(28)
<223> OTHER INFORMATION: Ile or Phe
<220> FEATURE:
<221> NAME/KEY: MOD_RES
<222> LOCATION: (30)..(30)
<223> OTHER INFORMATION: Leu or Pro
<220> FEATURE:
<221> NAME/KEY: MOD_RES
<222> LOCATION: (31)..(31)
<223> OTHER INFORMATION: Lys or Leu
<220> FEATURE:
<221> NAME/KEY: MOD_RES
<222> LOCATION: (32)..(33)
<223> OTHER INFORMATION: Arg or Leu
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (36)..(36)
<223> OTHER INFORMATION: Lys, Arg or His
<220> FEATURE:
<221> NAME/KEY: MOD_RES
```

```
<222> LOCATION: (37)..(41)
<223> OTHER INFORMATION: Any amino acid; This region may encompass 1-5
      residues
<220> FEATURE:
<221> NAME/KEY: MOD_RES
<222> LOCATION: (43)..(43)
<223> OTHER INFORMATION: Pro or Arg
<220> FEATURE:
<221> NAME/KEY: MOD_RES
<222> LOCATION: (45)..(46)
<223> OTHER INFORMATION: Any amino acid
<220> FEATURE:
<221> NAME/KEY: MOD_RES
<222> LOCATION: (50)..(50)
<223> OTHER INFORMATION: Phe or Leu
<220> FEATURE:
<221> NAME/KEY: MOD_RES
<222> LOCATION: (51)..(51)
<223> OTHER INFORMATION: Ile, Val, Leu or Met
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (56)..(56)
<223> OTHER INFORMATION: Gly or Arg
<220> FEATURE:
<221> NAME/KEY: MOD_RES
<222> LOCATION: (57)..(57)
<223> OTHER INFORMATION: Phe, Tyr or Trp
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (60)..(60)
<223> OTHER INFORMATION: Pro or Ala
<220> FEATURE:
<221> NAME/KEY: MOD_RES
<222> LOCATION: (61)..(61)
<223> OTHER INFORMATION: Tyr or His
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (63)..(63)
<223> OTHER INFORMATION: Ala, Gly, Ser or Thr
<220> FEATURE:
<221> NAME/KEY: MOD_RES
<222> LOCATION: (64)..(64)
<223> OTHER INFORMATION: Thr or Asn
<220> FEATURE:
<221> NAME/KEY: MOD_RES
<222> LOCATION: (65)..(65)
<223> OTHER INFORMATION: Ala, Gly, Ser or Thr
<220> FEATURE:
<221> NAME/KEY: MOD_RES
<222> LOCATION: (66)..(66)
<223> OTHER INFORMATION: Ile, Val, Leu or Met
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Ile, Val, Leu or Met
<220> FEATURE:
<221> NAME/KEY: MOD_RES
<222> LOCATION: (71)..(71)
<223> OTHER INFORMATION: Gln or Glu
<220> FEATURE:
<221> NAME/KEY: MOD_RES
<222> LOCATION: (72)..(72)
<223> OTHER INFORMATION: Gln or Asp
<220> FEATURE:
```

-continued

```
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (75)..(75)
<223> OTHER INFORMATION: Ala, Gly, Ser or Thr
<220> FEATURE:
<221> NAME/KEY: MOD_RES
<222> LOCATION: (76)..(76)
<223> OTHER INFORMATION: Lys, Arg or His
<220> FEATURE:
<221> NAME/KEY: MOD_RES
<222> LOCATION: (79)..(79)
<223> OTHER INFORMATION: Lys, Arg or His
<220> FEATURE:
<221> NAME/KEY: MOD_RES
<222> LOCATION: (80)..(80)
<223> OTHER INFORMATION: Ile, Val, Leu or Met
<220> FEATURE:
<221> NAME/KEY: MOD_RES
<222> LOCATION: (81)..(81)
<223> OTHER INFORMATION: Phe, Tyr or Trp
<220> FEATURE:
<221> NAME/KEY: MOD_RES
<222> LOCATION: (82)..(82)
<223> OTHER INFORMATION: Lys, Arg or His
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (87)..(87)
<223> OTHER INFORMATION: Gly or Cys
<220> FEATURE:
<221> NAME/KEY: MOD_RES
<222> LOCATION: (88)..(88)
<223> OTHER INFORMATION: Glu or Thr
<220> FEATURE:
<221> NAME/KEY: MOD_RES
<222> LOCATION: (89)..(89)
<223> OTHER INFORMATION: Pro or Arg
<220> FEATURE:
<221> NAME/KEY: MOD_RES
<222> LOCATION: (91)..(91)
<223> OTHER INFORMATION: Ile, Val, Leu or Met
<220> FEATURE:
<221> NAME/KEY: MOD_RES
<222> LOCATION: (94)..(94)
<223> OTHER INFORMATION: Ala or Cys
<220> FEATURE:
<221> NAME/KEY: MOD_RES
<222> LOCATION: (96)..(96)
<223> OTHER INFORMATION: Ala or Gln
<220> FEATURE:
<221> NAME/KEY: MOD_RES
<222> LOCATION: (97)..(97)
<223> OTHER INFORMATION: Gly or Asp
<220> FEATURE:
<221> NAME/KEY: MOD_RES
<222> LOCATION: (100)..(100)
<223> OTHER INFORMATION: Lys, Arg or His
<220> FEATURE:
<221> NAME/KEY: MOD_RES
<222> LOCATION: (101)..(101)
<223> OTHER INFORMATION: Phe, Tyr or Trp
<220> FEATURE:
<221> NAME/KEY: MOD_RES
<222> LOCATION: (107)..(107)
<223> OTHER INFORMATION: Gly or Glu
<220> FEATURE:
<221> NAME/KEY: MOD_RES
<222> LOCATION: (111)..(111)
<223> OTHER INFORMATION: Glu or Gln
<220> FEATURE:
<221> NAME/KEY: MOD_RES
<222> LOCATION: (117)..(117)
<223> OTHER INFORMATION: Ser or Pro
<220> FEATURE:
```

-continued

```
<221> NAME/KEY: MOD_RES
<222> LOCATION: (119)..(119)
<223> OTHER INFORMATION: Gly or His
<220> FEATURE:
<221> NAME/KEY: MOD_RES
<222> LOCATION: (125)..(125)
<223> OTHER INFORMATION: Trp or Ser
<220> FEATURE:
<221> NAME/KEY: MOD_RES
<222> LOCATION: (130)..(131)
<223> OTHER INFORMATION: Ile, Val, Leu or Met
<220> FEATURE:
<221> NAME/KEY: MOD_RES
<222> LOCATION: (133)..(133)
<223> OTHER INFORMATION: Asp or Glu
<220> FEATURE:
<221> NAME/KEY: MOD_RES
<222> LOCATION: (134)..(134)
<223> OTHER INFORMATION: Any amino acid
<220> FEATURE:
<221> NAME/KEY: MOD_RES
<222> LOCATION: (136)..(136)
<223> OTHER INFORMATION: Lys, Arg or His
<220> FEATURE:
<221> NAME/KEY: MOD_RES
<222> LOCATION: (137)..(137)
<223> OTHER INFORMATION: Any amino acid
<220> FEATURE:
<221> NAME/KEY: MOD_RES
<222> LOCATION: (138)..(138)
<223> OTHER INFORMATION: Ile, Val, Leu or Met
<220> FEATURE:
<221> NAME/KEY: MOD_RES
<222> LOCATION: (140)..(140)
<223> OTHER INFORMATION: Any amino acid
<220> FEATURE:
<221> NAME/KEY: MOD_RES
<222> LOCATION: (141)..(141)
<223> OTHER INFORMATION: Ile, Val, Leu or Met
<220> FEATURE:
<221> NAME/KEY: MOD_RES
<222> LOCATION: (142)..(142)
<223> OTHER INFORMATION: Ala, Gly, Ser or Thr
<220> FEATURE:
<221> NAME/KEY: MOD_RES
<222> LOCATION: (144)..(144)
<223> OTHER INFORMATION: Asn or Ala
<220> FEATURE:
<221> NAME/KEY: MOD_RES
<222> LOCATION: (145)..(145)
<223> OTHER INFORMATION: Phe or Leu
<220> FEATURE:
<221> NAME/KEY: MOD_RES
<222> LOCATION: (146)..(146)
<223> OTHER INFORMATION: Ile, Val, Leu or Met
<220> FEATURE:
<221> NAME/KEY: MOD_RES
<222> LOCATION: (147)..(147)
<223> OTHER INFORMATION: Ala, Gly, Ser or Thr
<220> FEATURE:
<221> NAME/KEY: MOD_RES
<222> LOCATION: (148)..(148)
<223> OTHER INFORMATION: His or Ser
<220> FEATURE:
<221> NAME/KEY: MOD_RES
<222> LOCATION: (149)..(149)
<223> OTHER INFORMATION: Any amino acid
<220> FEATURE:
<221> NAME/KEY: MOD_RES
<222> LOCATION: (150)..(150)
<223> OTHER INFORMATION: Lys, Arg or His
<220> FEATURE:
<221> NAME/KEY: MOD_RES
<222> LOCATION: (152)..(152)
<223> OTHER INFORMATION: Lys, Arg or His
<220> FEATURE:
<221> NAME/KEY: MOD_RES
<222> LOCATION: (153)..(154)
<223> OTHER INFORMATION: Any amino acid
<220> FEATURE:
```

```
<221> NAME/KEY: MOD_RES
<222> LOCATION: (155)..(155)
<223> OTHER INFORMATION: Leu or Tyr
<220> FEATURE:
<221> NAME/KEY: MOD_RES
<222> LOCATION: (157)..(157)
<223> OTHER INFORMATION: Any amino acid
<220> FEATURE:
<221> NAME/KEY: MOD_RES
<222> LOCATION: (158)..(158)
<223> OTHER INFORMATION: Asp or Glu
<220> FEATURE:
<221> NAME/KEY: MOD_RES
<222> LOCATION: (159)..(159)
<223> OTHER INFORMATION: Ile, Val, Leu or Met
<220> FEATURE:
<221> NAME/KEY: MOD_RES
<222> LOCATION: (161)..(161)
<223> OTHER INFORMATION: Lys, Arg or His
<220> FEATURE:
<221> NAME/KEY: MOD_RES
<222> LOCATION: (162)..(162)
<223> OTHER INFORMATION: His or Ile
<220> FEATURE:
<221> NAME/KEY: MOD_RES
<222> LOCATION: (163)..(163)
<223> OTHER INFORMATION: Ala, Gly, Ser or Thr
<220> FEATURE:
<221> NAME/KEY: MOD_RES
<222> LOCATION: (165)..(165)
<223> OTHER INFORMATION: Any amino acid
<220> FEATURE:
<221> NAME/KEY: MOD_RES
<222> LOCATION: (167)..(167)
<223> OTHER INFORMATION: Ile, Val, Leu or Met
<220> FEATURE:
<221> NAME/KEY: MOD_RES
<222> LOCATION: (168)..(168)
<223> OTHER INFORMATION: Any amino acid
<220> FEATURE:
<221> NAME/KEY: MOD_RES
<222> LOCATION: (169)..(169)
<223> OTHER INFORMATION: Ala, Gly, Ser or Thr
<220> FEATURE:
<221> NAME/KEY: MOD_RES
<222> LOCATION: (171)..(173)
<223> OTHER INFORMATION: Any amino acid
<220> FEATURE:
<221> NAME/KEY: MOD_RES
<222> LOCATION: (174)..(174)
<223> OTHER INFORMATION: Ala, Gly, Ser or Thr
<220> FEATURE:
<221> NAME/KEY: MOD_RES
<222> LOCATION: (175)..(181)
<223> OTHER INFORMATION: Any amino acid; This region may encompass 1-7
      residues
<220> FEATURE:
<221> NAME/KEY: MOD_RES
<222> LOCATION: (182)..(182)
<223> OTHER INFORMATION: Phe or Val
<220> FEATURE:
<221> NAME/KEY: MOD_RES
<222> LOCATION: (183)..(183)
<223> OTHER INFORMATION: Ala, Gly, Ser or Thr
<220> FEATURE:
<221> NAME/KEY: MOD_RES
<222> LOCATION: (184)..(184)
<223> OTHER INFORMATION: Ala or Phe
<220> FEATURE:
<221> NAME/KEY: MOD_RES
<222> LOCATION: (185)..(185)
<223> OTHER INFORMATION: Gln or Cys
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (187)..(187)
<223> OTHER INFORMATION: Glu or Gln
```

```
-continued

<220> FEATURE:
<221> NAME/KEY: MOD_RES
<222> LOCATION: (189)..(189)
<223> OTHER INFORMATION: Lys, Arg or His
<220> FEATURE:
<221> NAME/KEY: MOD_RES
<222> LOCATION: (192)..(192)
<223> OTHER INFORMATION: Ala, Gly, Ser or Thr
<220> FEATURE:
<221> NAME/KEY: MOD_RES
<222> LOCATION: (194)..(194)
<223> OTHER INFORMATION: Asn or Ser
<220> FEATURE:
<221> NAME/KEY: MOD_RES
<222> LOCATION: (195)..(196)
<223> OTHER INFORMATION: Ile, Val, Leu or Met
<220> FEATURE:
<221> NAME/KEY: MOD_RES
<222> LOCATION: (197)..(197)
<223> OTHER INFORMATION: Ala or Val
<220> FEATURE:
<221> NAME/KEY: MOD_RES
<222> LOCATION: (199)..(199)
<223> OTHER INFORMATION: Any amino acid
<220> FEATURE:
<221> NAME/KEY: MOD_RES
<222> LOCATION: (200)..(201)
<223> OTHER INFORMATION: Ile, Val, Leu or Met
<220> FEATURE:
<221> NAME/KEY: MOD_RES
<222> LOCATION: (202)..(202)
<223> OTHER INFORMATION: Ala, Gly, Ser or Thr
<220> FEATURE:
<221> NAME/KEY: MOD_RES
<222> LOCATION: (203)..(203)
<223> OTHER INFORMATION: Ile, Val, Leu or Met
<220> FEATURE:
<221> NAME/KEY: MOD_RES
<222> LOCATION: (204)..(204)
<223> OTHER INFORMATION: Asp or Ser
<220> FEATURE:
<221> NAME/KEY: MOD_RES
<222> LOCATION: (206)..(206)
<223> OTHER INFORMATION: Gly or Glu
<220> FEATURE:
<221> NAME/KEY: MOD_RES
<222> LOCATION: (208)..(208)
<223> OTHER INFORMATION: Glu or Pro
<220> FEATURE:
<221> NAME/KEY: MOD_RES
<222> LOCATION: (209)..(209)
<223> OTHER INFORMATION: Glu or Val
<220> FEATURE:
<221> NAME/KEY: MOD_RES
<222> LOCATION: (211)..(211)
<223> OTHER INFORMATION: Glu or Ala
<220> FEATURE:
<221> NAME/KEY: MOD_RES
<222> LOCATION: (212)..(212)
<223> OTHER INFORMATION: Gln or Arg
<220> FEATURE:
<221> NAME/KEY: MOD_RES
<222> LOCATION: (213)..(213)
<223> OTHER INFORMATION: Ile, Val, Leu or Met
<220> FEATURE:
<221> NAME/KEY: MOD_RES
<222> LOCATION: (214)..(215)
<223> OTHER INFORMATION: Any amino acid
<220> FEATURE:
<221> NAME/KEY: MOD_RES
<222> LOCATION: (216)..(216)
<223> OTHER INFORMATION: Asp or Glu
<220> FEATURE:
<221> NAME/KEY: MOD_RES
<222> LOCATION: (217)..(217)
<223> OTHER INFORMATION: Phe, Tyr or Trp
<220> FEATURE:
<221> NAME/KEY: MOD_RES
<222> LOCATION: (218)..(218)
<223> OTHER INFORMATION: Ile, Val, Leu or Met
```

```
-continued

<220> FEATURE:
<221> NAME/KEY: MOD_RES
<222> LOCATION: (219)..(219)
<223> OTHER INFORMATION: Ala, Gly, Ser or Thr
<220> FEATURE:
<221> NAME/KEY: MOD_RES
<222> LOCATION: (224)..(225)
<223> OTHER INFORMATION: Ile, Val, Leu or Met
<220> FEATURE:
<221> NAME/KEY: MOD_RES
<222> LOCATION: (227)..(227)
<223> OTHER INFORMATION: Ala or Phe
<220> FEATURE:
<221> NAME/KEY: MOD_RES
<222> LOCATION: (230)..(230)
<223> OTHER INFORMATION: Asn or Tyr
<220> FEATURE:
<221> NAME/KEY: MOD_RES
<222> LOCATION: (231)..(231)
<223> OTHER INFORMATION: Ile, Val, Leu or Met
<220> FEATURE:
<221> NAME/KEY: MOD_RES
<222> LOCATION: (235)..(235)
<223> OTHER INFORMATION: Ala or Pro
<220> FEATURE:
<221> NAME/KEY: MOD_RES
<222> LOCATION: (237)..(237)
<223> OTHER INFORMATION: Any amino acid
<220> FEATURE:
<221> NAME/KEY: MOD_RES
<222> LOCATION: (240)..(240)
<223> OTHER INFORMATION: Ile, Val, Leu or Met
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (242)..(242)
<223> OTHER INFORMATION: Ala, Gly, Ser or Thr
<220> FEATURE:
<221> NAME/KEY: MOD_RES
<222> LOCATION: (244)..(244)
<223> OTHER INFORMATION: Ala or Glu
<220> FEATURE:
<221> NAME/KEY: MOD_RES
<222> LOCATION: (245)..(245)
<223> OTHER INFORMATION: Any amino acid
<220> FEATURE:
<221> NAME/KEY: MOD_RES
<222> LOCATION: (247)..(247)
<223> OTHER INFORMATION: Leu or Ser
<220> FEATURE:
<221> NAME/KEY: MOD_RES
<222> LOCATION: (248)..(249)
<223> OTHER INFORMATION: Any amino acid
<220> FEATURE:
<221> NAME/KEY: MOD_RES
<222> LOCATION: (250)..(250)
<223> OTHER INFORMATION: Ile, Val, Leu or Met
<220> FEATURE:
<221> NAME/KEY: MOD_RES
<222> LOCATION: (251)..(251)
<223> OTHER INFORMATION: Glu or Lys
<220> FEATURE:
<221> NAME/KEY: MOD_RES
<222> LOCATION: (252)..(252)
<223> OTHER INFORMATION: Arg or Gly
<220> FEATURE:
<221> NAME/KEY: MOD_RES
<222> LOCATION: (253)..(253)
<223> OTHER INFORMATION: Lys or Ile
<220> FEATURE:
<221> NAME/KEY: MOD_RES
<222> LOCATION: (254)..(254)
<223> OTHER INFORMATION: Ile, Val, Leu or Met
<220> FEATURE:
<221> NAME/KEY: MOD_RES
<222> LOCATION: (255)..(255)
<223> OTHER INFORMATION: Glu or Lys
```

```
<220> FEATURE:
<221> NAME/KEY: MOD_RES
<222> LOCATION: (258)..(291)
<223> OTHER INFORMATION: Any amino acid; This region may encompass 1-34
      residues
<220> FEATURE:
<221> NAME/KEY: MOD_RES
<222> LOCATION: (292)..(292)
<223> OTHER INFORMATION: Asp or Gly
<220> FEATURE:
<221> NAME/KEY: MOD_RES
<222> LOCATION: (294)..(294)
<223> OTHER INFORMATION: Leu or Phe
<220> FEATURE:
<221> NAME/KEY: MOD_RES
<222> LOCATION: (296)..(296)
<223> OTHER INFORMATION: Gly or Asp
<220> FEATURE:
<221> NAME/KEY: MOD_RES
<222> LOCATION: (297)..(297)
<223> OTHER INFORMATION: Trp or Val
<220> FEATURE:
<221> NAME/KEY: MOD_RES
<222> LOCATION: (298)..(298)
<223> OTHER INFORMATION: Any amino acid
<220> FEATURE:
<221> NAME/KEY: MOD_RES
<222> LOCATION: (300)..(300)
<223> OTHER INFORMATION: Lys or Ser
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (302)..(302)
<223> OTHER INFORMATION: Ser or Asn
<220> FEATURE:
<221> NAME/KEY: MOD_RES
<222> LOCATION: (303)..(303)
<223> OTHER INFORMATION: Asn or Glu
<220> FEATURE:
<221> NAME/KEY: MOD_RES
<222> LOCATION: (306)..(306)
<223> OTHER INFORMATION: Any amino acid
<220> FEATURE:
<221> NAME/KEY: MOD_RES
<222> LOCATION: (308)..(308)
<223> OTHER INFORMATION: Gln or Glu
<220> FEATURE:
<221> NAME/KEY: MOD_RES
<222> LOCATION: (309)..(309)
<223> OTHER INFORMATION: Ile or Lys
<220> FEATURE:
<221> NAME/KEY: MOD_RES
<222> LOCATION: (310)..(310)
<223> OTHER INFORMATION: Ile, Val, Leu or Met
<220> FEATURE:
<221> NAME/KEY: MOD_RES
<222> LOCATION: (311)..(311)
<223> OTHER INFORMATION: Asp or Ser
<220> FEATURE:
<221> NAME/KEY: MOD_RES
<222> LOCATION: (312)..(312)
<223> OTHER INFORMATION: Leu or Phe
<220> FEATURE:
<221> NAME/KEY: MOD_RES
<222> LOCATION: (313)..(313)
<223> OTHER INFORMATION: Ile, Val, Leu or Met
<220> FEATURE:
<221> NAME/KEY: MOD_RES
<222> LOCATION: (315)..(315)
<223> OTHER INFORMATION: Ser or Asp
<220> FEATURE:
<221> NAME/KEY: MOD_RES
<222> LOCATION: (316)..(316)
<223> OTHER INFORMATION: Leu or Ser
<220> FEATURE:
<221> NAME/KEY: MOD_RES
<222> LOCATION: (318)..(318)
```

-continued

```
<223> OTHER INFORMATION: Phe or Leu
<220> FEATURE:
<221> NAME/KEY: MOD_RES
<222> LOCATION: (319)..(319)
<223> OTHER INFORMATION: Ala, Gly, Ser or Thr
<220> FEATURE:
<221> NAME/KEY: MOD_RES
<222> LOCATION: (321)..(321)
<223> OTHER INFORMATION: His or Tyr
<220> FEATURE:
<221> NAME/KEY: MOD_RES
<222> LOCATION: (324)..(324)
<223> OTHER INFORMATION: Ala, Gly, Ser or Thr
<220> FEATURE:
<221> NAME/KEY: MOD_RES
<222> LOCATION: (326)..(326)
<223> OTHER INFORMATION: Ile, Val, Leu or Met
<220> FEATURE:
<221> NAME/KEY: MOD_RES
<222> LOCATION: (327)..(327)
<223> OTHER INFORMATION: Ala or Leu
<220> FEATURE:
<221> NAME/KEY: MOD_RES
<222> LOCATION: (328)..(328)
<223> OTHER INFORMATION: Ile, Val, Leu or Met
<220> FEATURE:
<221> NAME/KEY: MOD_RES
<222> LOCATION: (329)..(329)
<223> OTHER INFORMATION: Ala, Gly, Ser or Thr
<220> FEATURE:
<221> NAME/KEY: MOD_RES
<222> LOCATION: (330)..(330)
<223> OTHER INFORMATION: Ile, Val, Leu or Met
<220> FEATURE:
<221> NAME/KEY: MOD_RES
<222> LOCATION: (331)..(331)
<223> OTHER INFORMATION: Ala or Val
<220> FEATURE:
<221> NAME/KEY: MOD_RES
<222> LOCATION: (332)..(332)
<223> OTHER INFORMATION: Ile, Val, Leu or Met
<220> FEATURE:
<221> NAME/KEY: MOD_RES
<222> LOCATION: (333)..(333)
<223> OTHER INFORMATION: Phe, Tyr or Trp
<220> FEATURE:
<221> NAME/KEY: MOD_RES
<222> LOCATION: (336)..(337)
<223> OTHER INFORMATION: Any amino acid
<220> FEATURE:
<221> NAME/KEY: MOD_RES
<222> LOCATION: (338)..(338)
<223> OTHER INFORMATION: Cys or Ser
<220> FEATURE:
<221> NAME/KEY: MOD_RES
<222> LOCATION: (339)..(339)
<223> OTHER INFORMATION: Pro or Ala
<220> FEATURE:
<221> NAME/KEY: MOD_RES
<222> LOCATION: (340)..(340)
<223> OTHER INFORMATION: Lys or Gln
<220> FEATURE:
<221> NAME/KEY: MOD_RES
<222> LOCATION: (341)..(341)
<223> OTHER INFORMATION: Ala or Asp
<220> FEATURE:
<221> NAME/KEY: MOD_RES
<222> LOCATION: (342)..(342)
<223> OTHER INFORMATION: Ile, Val, Leu or Met
<220> FEATURE:
<221> NAME/KEY: MOD_RES
<222> LOCATION: (343)..(343)
<223> OTHER INFORMATION: Any amino acid
<220> FEATURE:
<221> NAME/KEY: MOD_RES
<222> LOCATION: (344)..(344)
<223> OTHER INFORMATION: Glu or Leu
<220> FEATURE:
<221> NAME/KEY: MOD_RES
<222> LOCATION: (345)..(345)
```

```
<223> OTHER INFORMATION: Ile, Val, Leu or Met
<220> FEATURE:
<221> NAME/KEY: MOD_RES
<222> LOCATION: (346)..(346)
<223> OTHER INFORMATION: Lys, Arg or His
<220> FEATURE:
<221> NAME/KEY: MOD_RES
<222> LOCATION: (347)..(347)
<223> OTHER INFORMATION: Glu or Arg
<220> FEATURE:
<221> NAME/KEY: MOD_RES
<222> LOCATION: (350)..(350)
<223> OTHER INFORMATION: Leu or Asp
<220> FEATURE:
<221> NAME/KEY: MOD_RES
<222> LOCATION: (351)..(351)
<223> OTHER INFORMATION: Any amino acid
<220> FEATURE:
<221> NAME/KEY: MOD_RES
<222> LOCATION: (353)..(353)
<223> OTHER INFORMATION: Ala or Arg
<220> FEATURE:
<221> NAME/KEY: MOD_RES
<222> LOCATION: (354)..(354)
<223> OTHER INFORMATION: Arg or Ser
<220> FEATURE:
<221> NAME/KEY: MOD_RES
<222> LOCATION: (355)..(355)
<223> OTHER INFORMATION: Any amino acid
<220> FEATURE:
<221> NAME/KEY: MOD_RES
<222> LOCATION: (356)..(356)
<223> OTHER INFORMATION: Lys or Gln
<220> FEATURE:
<221> NAME/KEY: MOD_RES
<222> LOCATION: (357)..(360)
<223> OTHER INFORMATION: Any amino acid; This region may encompass 2-4
      residues
<220> FEATURE:
<221> NAME/KEY: MOD_RES
<222> LOCATION: (362)..(363)
<223> OTHER INFORMATION: Any amino acid
<220> FEATURE:
<221> NAME/KEY: MOD_RES
<222> LOCATION: (365)..(365)
<223> OTHER INFORMATION: Any amino acid
<220> FEATURE:
<221> NAME/KEY: MOD_RES
<222> LOCATION: (366)..(366)
<223> OTHER INFORMATION: Trp or Ser
<220> FEATURE:
<221> NAME/KEY: MOD_RES
<222> LOCATION: (367)..(367)
<223> OTHER INFORMATION: Asp or Glu
<220> FEATURE:
<221> NAME/KEY: MOD_RES
<222> LOCATION: (371)..(371)
<223> OTHER INFORMATION: Lys or Glu
<220> FEATURE:
<221> NAME/KEY: MOD_RES
<222> LOCATION: (373)..(373)
<223> OTHER INFORMATION: Any amino acid
<220> FEATURE:
<221> NAME/KEY: MOD_RES
<222> LOCATION: (374)..(374)
<223> OTHER INFORMATION: Phe, Tyr or Trp
<220> FEATURE:
<221> NAME/KEY: MOD_RES
<222> LOCATION: (377)..(377)
<223> OTHER INFORMATION: Cys or Gln
<220> FEATURE:
<221> NAME/KEY: MOD_RES
<222> LOCATION: (382)..(382)
<223> OTHER INFORMATION: Ala, Gly, Ser or Thr
<220> FEATURE:
<221> NAME/KEY: MOD_RES
<222> LOCATION: (385)..(385)
<223> OTHER INFORMATION: Leu or Cys
<220> FEATURE:
<221> NAME/KEY: MOD_RES
```

```
<222> LOCATION: (388)..(388)
<223> OTHER INFORMATION: Ile, Val, Leu or Met
<220> FEATURE:
<221> NAME/KEY: MOD_RES
<222> LOCATION: (390)..(390)
<223> OTHER INFORMATION: Lys, Arg or His
<220> FEATURE:
<221> NAME/KEY: MOD_RES
<222> LOCATION: (392)..(392)
<223> OTHER INFORMATION: Ile, Val, Leu or Met
<220> FEATURE:
<221> NAME/KEY: MOD_RES
<222> LOCATION: (396)..(396)
<223> OTHER INFORMATION: Ala or Val
<220> FEATURE:
<221> NAME/KEY: MOD_RES
<222> LOCATION: (397)..(397)
<223> OTHER INFORMATION: Ile, Val, Leu or Met
<220> FEATURE:
<221> NAME/KEY: MOD_RES
<222> LOCATION: (401)..(401)
<223> OTHER INFORMATION: Lys, Arg or His
<220> FEATURE:
<221> NAME/KEY: MOD_RES
<222> LOCATION: (404)..(404)
<223> OTHER INFORMATION: Gly or Glu
<220> FEATURE:
<221> NAME/KEY: MOD_RES
<222> LOCATION: (406)..(406)
<223> OTHER INFORMATION: Asp or Leu
<220> FEATURE:
<221> NAME/KEY: MOD_RES
<222> LOCATION: (413)..(413)
<223> OTHER INFORMATION: Ile, Val, Leu or Met
<220> FEATURE:
<221> NAME/KEY: MOD_RES
<222> LOCATION: (417)..(417)
<223> OTHER INFORMATION: Any amino acid
<220> FEATURE:
<221> NAME/KEY: MOD_RES
<222> LOCATION: (418)..(418)
<223> OTHER INFORMATION: Ala, Gly, Ser or Thr
<220> FEATURE:
<221> NAME/KEY: MOD_RES
<222> LOCATION: (423)..(423)
<223> OTHER INFORMATION: Asp or Asn
<220> FEATURE:
<221> NAME/KEY: MOD_RES
<222> LOCATION: (424)..(424)
<223> OTHER INFORMATION: Any amino acid
<220> FEATURE:
<221> NAME/KEY: MOD_RES
<222> LOCATION: (426)..(426)
<223> OTHER INFORMATION: Arg or Leu
<220> FEATURE:
<221> NAME/KEY: MOD_RES
<222> LOCATION: (427)..(427)
<223> OTHER INFORMATION: Tyr or His
<220> FEATURE:
<221> NAME/KEY: MOD_RES
<222> LOCATION: (428)..(428)
<223> OTHER INFORMATION: Any amino acid
<220> FEATURE:
<221> NAME/KEY: MOD_RES
<222> LOCATION: (429)..(429)
<223> OTHER INFORMATION: Gln or Asp
<220> FEATURE:
<221> NAME/KEY: MOD_RES
<222> LOCATION: (430)..(430)
<223> OTHER INFORMATION: Pro or Ala
<220> FEATURE:
<221> NAME/KEY: MOD_RES
<222> LOCATION: (431)..(431)
<223> OTHER INFORMATION: Asn or Gln
<220> FEATURE:
<221> NAME/KEY: MOD_RES
<222> LOCATION: (432)..(432)
<223> OTHER INFORMATION: Any amino acid
<220> FEATURE:
<221> NAME/KEY: MOD_RES
```

```
<222> LOCATION: (434)..(434)
<223> OTHER INFORMATION: Asn or Gln
<220> FEATURE:
<221> NAME/KEY: MOD_RES
<222> LOCATION: (436)..(436)
<223> OTHER INFORMATION: Trp or Cys
<220> FEATURE:
<221> NAME/KEY: MOD_RES
<222> LOCATION: (439)..(459)
<223> OTHER INFORMATION: Any amino acid; This region may encompass 3-21
      residues
<220> FEATURE:
<221> NAME/KEY: MOD_RES
<222> LOCATION: (460)..(460)
<223> OTHER INFORMATION: Phe, Tyr or Trp
<220> FEATURE:
<221> NAME/KEY: MOD_RES
<222> LOCATION: (461)..(461)
<223> OTHER INFORMATION: Met or Thr
<220> FEATURE:
<221> NAME/KEY: MOD_RES
<222> LOCATION: (463)..(463)
<223> OTHER INFORMATION: Phe, Tyr or Trp
<220> FEATURE:
<221> NAME/KEY: MOD_RES
<222> LOCATION: (467)..(467)
<223> OTHER INFORMATION: Pro or Thr
<220> FEATURE:
<221> NAME/KEY: MOD_RES
<222> LOCATION: (471)..(471)
<223> OTHER INFORMATION: Ala or Pro
<220> FEATURE:
<221> NAME/KEY: MOD_RES
<222> LOCATION: (478)..(478)
<223> OTHER INFORMATION: Ile, Val, Leu or Met
<220> FEATURE:
<221> NAME/KEY: MOD_RES
<222> LOCATION: (480)..(480)
<223> OTHER INFORMATION: Met or Thr
<220> FEATURE:
<221> NAME/KEY: MOD_RES
<222> LOCATION: (482)..(482)
<223> OTHER INFORMATION: Val or Phe
<220> FEATURE:
<221> NAME/KEY: MOD_RES
<222> LOCATION: (484)..(484)
<223> OTHER INFORMATION: Ile, Val, Leu or Met

<400> SEQUENCE: 41

Met Xaa Xaa Xaa Xaa His Xaa Leu Xaa Xaa Leu Xaa Xaa Xaa Xaa
1               5                   10                  15

Xaa Xaa Ser Leu Leu Xaa Leu Xaa Leu Xaa Xaa Leu Xaa Xaa Xaa
                20                  25                  30

Xaa Asn Xaa Xaa Xaa Xaa Xaa Xaa Pro Xaa Gly Xaa Xaa Gly Trp
            35                  40                  45

Pro Xaa Xaa Gly Glu Thr Xaa Xaa Xaa Leu Xaa Xaa Xaa Xaa Xaa
    50                  55                  60

Xaa Xaa Gly Xaa Phe Xaa Xaa Xaa His Xaa Xaa Xaa Tyr Gly Xaa
65                  70                  75                  80

Xaa Xaa Ser Xaa Leu Phe Xaa Xaa Xaa Thr Xaa Val Ser Xaa Asp Xaa
                85                  90                  95

Xaa Leu Asn Xaa Xaa Ile Leu Gln Asn Glu Xaa Arg Leu Phe Xaa Cys
            100                 105                 110

Ser Tyr Pro Arg Xaa Ile Xaa Gly Ile Leu Gly Lys Xaa Ser Met Leu
        115                 120                 125

Val Xaa Xaa Gly Xaa Xaa His Xaa Xaa Xaa Arg Xaa Xaa Xaa Leu Xaa
    130                 135                 140

Xaa Xaa Xaa Xaa Xaa Xaa Leu Xaa Xaa Xaa Xaa Leu Xaa Xaa Xaa Glu
145                 150                 155                 160
```

```
Xaa Xaa Xaa Leu Xaa Val Xaa Xaa Xaa Trp Xaa Xaa Xaa Xaa Xaa
            165         170                 175

Xaa Xaa Xaa Xaa Xaa Xaa Xaa Xaa Xaa Ala Xaa Lys Phe Xaa
            180             185             190

Phe Xaa Xaa Xaa Xaa Lys Xaa Xaa Xaa Xaa Xaa Pro Xaa Glu Xaa
        195             200             205

Xaa Thr Xaa Xaa Xaa Xaa Xaa Xaa Xaa Xaa Phe Met Lys Gly Xaa
        210             215             220

Xaa Ser Xaa Pro Leu Xaa Xaa Pro Gly Thr Xaa Tyr Xaa Lys Ala Xaa
225             230             235                 240

Xaa Xaa Arg Xaa Xaa Ile Xaa Xaa Xaa Xaa Xaa Xaa Xaa Xaa Glu
            245             250                 255

Arg Xaa Xaa Xaa Xaa Xaa Xaa Xaa Xaa Xaa Xaa Xaa Xaa Xaa Xaa
            260             265                 270

Xaa Xaa Xaa Xaa Xaa Xaa Xaa Xaa Xaa Xaa Xaa Xaa Xaa Xaa Xaa
            275             280                 285

Xaa Xaa Xaa Xaa Asp Xaa Leu Xaa Xaa Xaa Leu Xaa Xaa Xaa Leu
            290             295             300

Ser Xaa Glu Xaa Xaa Xaa Xaa Xaa Leu Xaa Xaa Leu Xaa Xaa Gly
305             310             315                 320

Xaa Glu Thr Xaa Ser Xaa Xaa Xaa Xaa Xaa Xaa Xaa Xaa Phe Leu Xaa
            325             330                 335

Xaa Xaa Xaa Xaa Xaa Xaa Xaa Xaa Xaa Xaa Glu His Xaa Xaa Ile
            340             345             350

Xaa Xaa Xaa Xaa Xaa Xaa Xaa Glu Xaa Xaa Leu Xaa Xaa Xaa Asp
            355             360             365

Tyr Lys Xaa Met Xaa Xaa Thr Gln Xaa Val Ile Asn Glu Xaa Leu Arg
    370             375             380

Xaa Gly Asn Xaa Val Xaa Phe Xaa His Arg Lys Xaa Xaa Lys Asp Val
385             390             395                 400

Xaa Tyr Lys Xaa Tyr Xaa Ile Pro Ser Gly Trp Lys Xaa Leu Pro Val
            405             410             415

Xaa Xaa Ala Val His Leu Xaa Xaa Ser Xaa Xaa Xaa Xaa Xaa Xaa
            420             425             430

Phe Xaa Pro Xaa Arg Trp Xaa Xaa Xaa Xaa Xaa Xaa Xaa Xaa Xaa
        435             440             445

Xaa Xaa Xaa Xaa Xaa Xaa Xaa Xaa Xaa Xaa Xaa Xaa Pro Xaa Gly
            450             455             460

Gly Gly Xaa Arg Leu Cys Xaa Gly Ser Glu Leu Ala Lys Xaa Glu Xaa
465             470             475                 480

Ala Xaa Phe Xaa His His Leu Val
                485
```

US 7,897,839 B2

METHODS FOR MODIFYING PLANT CHARACTERISTICS

CROSS-REFERENCE TO RELATED APPLICATIONS

This application claims priority under 35 U.S.C. § 119 to U.S. Provisional Application Ser. No. 60/565,031, filed Apr. 23, 2004 and to U.S. Provisional Application Ser. No. 60/644,612, filed Jan. 18, 2005, the entire contents of both of which are incorporated herein in their entirety.

TECHNICAL FIELD

The present invention relates to polynucleotides that encode polypeptides, such as polypeptides that function in the brassinosteroid biosynthesis pathway, transgenic plants including the same, and methods for modifying plant phenotypic characteristics using the same. More particularly, the invention relates to transgenic plants exhibit increased levels of one or more of the following metabolites: sucrose, glutamate (glutamic acid), or linoleic acid. In addition, the invention relates to transgenic plants that exhibit increased levels of 6-deoxocathasterone and/or decreased levels of campestanol. The transgenic plants may also exhibit increased growth potential, increased size (e.g., height), increased seed yield, more uniform seed fill (e.g., in monocots), increased seed weight per plant, increased seeds per plant, a more rapid rate of growth, more efficient photosynthesis, or improved drought tolerance.

BACKGROUND OF THE INVENTION

Increased demands on the agricultural and forestry industries due to world-wide population growth have resulted in efforts to increase plant production and/or size. Although one means for increasing plant size is through plant breeding programs, such breeding programs are typically time-consuming and labor-intensive. Genetic manipulation of plant characteristics through the introduction of exogenous nucleic acids conferring a desirable trait, on the other hand, can be less time-consuming and possibly applicable across a variety of plant species.

Plants produce a number of steroids and sterols, termed brassinosteroids (BRs), some of which function as growth-promoting hormones. There are over 40 BRs known, typically with characteristic oxygen moieties at one or more of the C-2, C-6, C-22, and C-23 positions. Brassinolide (BL) is the most bioactive form of the growth-promoting BRs. $Arabidopsis$ CPD and DWF4 are cytochrome $P_{450}$ proteins that catalyze enzymatic steps in the BL biosynthetic pathway; they are 43% identical at the amino acid level. During the biosynthesis of BL, DWF4 catalyzes the oxidation of campestanol at C-22 to form 6-deoxocathasterone, while CPD catalyzes the adjacent step downstream, the hydroxylation of 6-deoxocathasterone at C-23 to produce 6-deoxyteasterone.

SUMMARY OF THE INVENTION

Provided herein are isolated polynucleotides, polypeptides encoded thereby, and transgenic plants including the same. A transgenic plant can demonstrate desired phenotypic characteristics relative to a control plant, such as one or more of increased height, increased photosynthetic rate, increased levels of one or more metabolites such as sucrose, glutamate, or linoleic acid, an increased level of 6-deoxocathasterone, a decreased level of campestanol, increased activity (e.g., enzymatic activity), improved water efficiency, increased seed weight per plant, increased seeds per plant, and increased drought tolerance.

Also provided herein are functionally comparable polypeptides (homologs and orthologs) to the $Arabidopsis$ $P_{450}$ protein known as DWF4. DWF4 plays an important role in the synthesis of brassinosteroids, which function as plant growth-promoting hormones. The invention thus provides, among other things, isolated polynucleotides that encode $P_{450}$ polypeptides. The $P_{450}$ polypeptides in some cases can function in the brassinosteroid biosynthesis pathway. For example, some of the $P_{450}$ polypeptides can perform an enzymatic activity of DWF4, e.g., oxidation of campestanol at C-22 to form 6-deoxocathasterone.

The disclosure also provides transgenic plants that include the polynucleotides described herein, and methods for making the same. Expression of the polypeptides in plants can result in one or more phenotypic effects, such as increased plant size (e.g., height, biomass) and/or a more rapid rate of growth; increased seed yield; improved seed fill (e.g., for monocots such as rice, wheat, and corn); increased levels of metabolites such as sucrose, glutamate, or linoleic acid; a decreased level of campestanol; an increased level of 6-deoxocathasterone; increased photosynthetic rates; improved water efficiency; or improved drought tolerance. In other cases, expression of the polypeptides can provide biochemical or enzymatic activities not normally present in the plant (e.g., not present at all or only in certain tissues), or can provide increased levels of such biochemical activities. In certain cases, expression of the polypeptides can complement biochemical or enzymatic functions already present in the plant, or can result in altered enzymatic activity (e.g., increased activity, decreased activity, or a different activity). Inhibition of expression of the $P_{450}$ polypeptides in plants, e.g., by antisense, RNAi, or ribozyme-based methods, can result in improved shade tolerance of the plants (e.g., as indicated by repressed elongation under shade conditions).

Accordingly, in one aspect, isolated polynucleotides are provided. An isolated polynucleotide can include a nucleic acid molecule encoding a polypeptide having about 85% or greater sequence identity to the amino acid sequence set forth in SEQ ID NO:2; e.g., comprising the amino acid sequence set forth in SEQ ID NO:2 or consisting of the amino acid sequence set forth in SEQ ID NO:2. A polypeptide can be effective for catalyzing the oxidation of campestanol at C-22 to form 6-deoxocathasterone.

A polynucleotide can further include a control element operably linked to the nucleic acid encoding the polypeptide, such as a broadly expressing promoter or a constitutive promoter. In some cases, a broadly expressing promoter is selected from the group consisting of p326, YP0158, YP0214, YP0380, PT0848, PT0633, YP0050, YP0144 and YP0190. In some cases, a constitutive promoter is 35S.

In some cases, an encoded polypeptide does not exhibit 93% or greater sequence identity to the amino acid sequences set forth in SEQ ID NO:1 or SEQ ID NO:3.

Recombinant vectors comprising the polynucleotides described above are also provided herein. A recombinant vector can include a control element operably linked to the polynucleotide, where the polynucleotide includes a nucleic acid molecule encoding a polypeptide having about 85% or greater sequence identity to the amino acid sequence set forth in SEQ ID NO:2.

In another aspect, transgenic plants are also provided. A transgenic plant can include at least one exogenous polynucleotide, the at least one exogenous polynucleotide comprising a nucleic acid encoding a polypeptide having about 85% or greater sequence identity to the amino acid sequence set forth in SEQ ID NO:2, provided that the encoded polypeptide does not exhibit 93% or greater sequence identity to the amino acid sequences set forth in SEQ ID NO:1 or SEQ ID NO:3. The polypeptide can be effective for catalyzing the oxidation of campestanol at C-22 to form 6-deoxocathasterone. In some cases, an exogenous polynucleotide further comprises a control element operably linked to the nucleic acid encoding the polypeptide. The control element can be a broadly expressing promoter or a constitutive promoter. A broadly expressing promoter can be selected from the group consisting of: p326, YP0158, YP0214, YP0380, PT0848, PT0633, YP0050, YP0144 and YP0190. The p326 promoter can be effective to cause expression of the polypeptide in the shoot and shoot tip. A transgenic plant can exhibit an altered phenotype relative to a control plant. The altered phenotype can be selected from one or more of the group consisting of: an altered metabolic profile, an increase in a level of 6-deoxocathasterone, a decrease in a level of campestanol, an increased photosynthetic rate, an increased seed yield, an increased seed weight per plant, and an increased height relative to a control plant. An altered metabolic profile can be an increased level of sucrose, glutamate, or linoleic acid relative to a control plant. A transgenic plant can be a monocot, such as rice, wheat, switchgrass, rye, barley, sorghum, or corn. A transgenic plant can be a dicot.

In another aspect, a transgenic plant is not an *Arabidopsis thaliana* or *Nicotiana tabacum* plant. Such a transgenic plant can include at least one exogenous polynucleotide, the at least one exogenous polynucleotide including a nucleic acid encoding a polypeptide having about 85% or greater sequence identity to the amino acid sequence set forth in SEQ ID NO:2. The exogenous polynucleotide can further comprise a control element operably linked to the nucleic acid encoding the polypeptide. The control element can be a broadly expressing promoter or a constitutive promoter. The broadly expressing promoter can be selected from the group consisting of: p326, YP0158, YP0214, YP0380, PT0848, PT0633, YP0050, YP0144 and YP0190. The p326 promoter can be effective to cause expression of the polypeptide in the shoot and shoot tip. A transgenic plant can exhibit an altered phenotype relative to a control plant. An altered phenotype can be selected from one or more of the group consisting of: an altered metabolic profile, an increase in a level of 6-deoxocathasterone, a decrease in a level of campestanol, an increased photosynthetic rate, an increased seed yield, an increased seed weight per plant, and an increased height relative to the control plant. An altered metabolic profile can be an increased level of sucrose, glutamate, or linoleic acid relative to the control plant. A transgenic plant can be a monocot, such as rice, wheat, switchgrass, rye, barley, sorghum, or corn. The transgenic plant can be a dicot. A polypeptide can be effective for catalyzing the oxidation of campestanol at C-22 to form 6-deoxocathasterone.

In another embodiment, a transgenic plant including at least one exogenous polynucleotide is provided, the at least one exogenous polynucleotide comprising a nucleic acid encoding a polypeptide having about 85% or greater sequence identity to the amino acid sequence set forth in SEQ ID NO:2, where the transgenic plant exhibits an increase in a level of 6-deoxocathasterone relative to a control plant. The exogenous polynucleotide can further include a control element operably linked to the nucleic acid encoding the polypeptide. A control element can be a broadly expressing promoter or a constitutive promoter. A broadly expressing promoter can be selected from the group consisting of: p326, YP0158, YP0214, YP0380, PT0848, PT0633, YP0050, YP0144 and YP0190. A p326 promoter can be effective to cause expression of the polypeptide in the shoot and shoot tip. A transgenic plant can exhibit an altered phenotype relative to a control plant selected from one or more of the group consisting of: an altered metabolic profile, a decrease in a level of campestanol, an increased photosynthetic rate, an increased seed yield, an increased seed weight per plant, and an increased height relative to the control plant. A transgenic plant can be a monocot such as rice, wheat, switchgrass, rye, barley, sorghum, or corn, or a dicot, as described above. A polypeptide can be effective for catalyzing the oxidation of campestanol at C-22 to form 6-deoxocathasterone.

In another aspect, provided herein is a transgenic plant including at least one exogenous polynucleotide, the at least one exogenous polynucleotide comprising a nucleic acid encoding a polypeptide having about 85% or greater sequence identity to the amino acid sequence set forth in SEQ ID NO:2, where the transgenic plant exhibits a decrease in a level of campestanol relative to a control plant. The exogenous polynucleotide can further include a control element operably linked to the nucleic acid encoding the polypeptide. The control element can be a broadly expressing promoter or a constitutive promoter. A broadly expressing promoter can be selected from the group consisting of: p326, YP0158, YP0214, YP0380, PT0848, PT0633, YP0050, YP0144 and YP0190. A p326 promoter can be effective to cause expression of the polypeptide in the shoot and shoot tip. The transgenic plant can further exhibit an altered phenotype relative to a control plant selected from one or more of the group consisting of: an altered metabolic profile, an increase in a level of 6-deoxocathasterone, an increased photosynthetic rate, an increased seed yield, an increased seed weight per plant, and an increased height relative to the control plant. A transgenic plant can be a monocot, such as rice, wheat, switchgrass, rye, barley, sorghum, or corn, or a dicot. A polypeptide can be effective for catalyzing the oxidation of campestanol at C-22 to form 6-deoxocathasterone.

In another embodiment, a transgenic plant comprising at least one exogenous polynucleotide is provided. The at least one exogenous polynucleotide can include a nucleic acid encoding a polypeptide having about 85% or greater sequence identity to the amino acid sequence set forth in SEQ ID NO:2, where the exogenous polynucleotide further comprises a broadly expressing control element operably linked to the nucleic acid encoding the polypeptide. A broadly expressing promoter can be selected from the group consisting of: p326, YP0158, YP0214, YP0380, PT0848, PT0633, YP0050, YP0144 and YP0190. The transgenic plant can exhibit an altered phenotype relative to a control plant selected from one or more of the group consisting of: an altered metabolic profile, a decrease in a level of campestanol, an increase in a level of 6-deoxocathasterone, an increased photosynthetic rate, an increased seed yield, an increased seed weight per plant, and an increased height relative to said control plant. An altered metabolic profile can be an increased level of sucrose, glutamate, or linoleic acid relative to the control plant. A transgenic plant can be a monocot, such as rice, wheat, switchgrass, rye, barley, sorghum, or corn. A transgenic plant can be a dicot. A polypeptide can be effective for catalyzing the oxidation of campestanol at C-22 to form 6-deoxocathasterone.

In a further aspect, a transgenic plant including at least one exogenous polynucleotide is provided. The at least one exogenous polynucleotide can include a nucleic acid encoding a polypeptide having about 85% or greater sequence identity to the amino acid sequence set forth in SEQ ID NO:2, where the transgenic plant exhibits an increased photosynthetic rate relative to a control plant. The exogenous polynucleotide can further include a control element operably linked to the nucleic acid encoding the polypeptide. A control element can be a broadly expressing promoter or a constitutive promoter. A broadly expressing promoter can be selected from the group consisting of: p326, YP0158, YP0214, YP0380, PT0848, PT0633, YP0050, YP0144 and YP0190. A broadly expressing promoter can be p326, which can be effective to cause expression of said polypeptide in the shoot and shoot tip. A transgenic plant can further exhibit an altered phenotype relative to a control plant selected from one or more of the group consisting of: an altered metabolic profile, a decrease in a level of campestanol, an increase in a level of 6-deoxocathasterone, an increased seed yield, an increased seed weight per plant, and an increased height relative to the control plant. An altered metabolic profile can be an increased level of sucrose, glutamate, or linoleic acid relative to the control plant. A transgenic plant can be a monocot, such as rice, wheat, switchgrass, rye, barley, sorghum, or corn, or can be a dicot. A polypeptide can be effective for catalyzing the oxidation of campestanol at C-22 to form 6-deoxocathasterone.

Also provided are methods for producing transgenic plants. A method for producing a transgenic plant can include (a) introducing any of the polynucleotides described herein into a plant cell to produce a transformed plant cell; and (b) producing a transgenic plant from the transformed plant cell. A seed of any transgenic plant described herein is also provided.

In another aspect, isolated polypeptides are provided. An isolated polypeptide can have about 85% or greater sequence identity to the amino acid sequence set forth in SEQ ID NO:2, provided that the encoded polypeptide does not exhibit 93% or greater sequence identity to the amino acid sequences set forth in SEQ ID NO:1 or SEQ ID NO:3.

The disclosure also provides methods for altering one or more phenotypic characteristics of a plant. For example, a method for increasing the level of one or more metabolites selected from the group consisting of sucrose, glutamate, and linoleic acid in a plant is provided. The method includes:

(a) introducing any of the polynucleotides described previously into a plant cell to produce a transformed plant cell; and (b) producing a transgenic plant from the transformed plant cell, where the transgenic plant exhibits an increased level of the one or more metabolites.

In another embodiment, a method for increasing the level of one or more metabolites selected from the group consisting of sucrose, glutamate, and linoleic acid in a plant includes: (a) introducing into a plant cell an isolated polynucleotide comprising a nucleic acid molecule encoding a polypeptide having about 85% or greater sequence identity to the amino acid sequence set forth in SEQ ID NO:2 to produce a transformed plant cell; and (b) producing a transgenic plant from the transformed plant cell, where the transgenic plant exhibits an increased level of the one or more metabolites.

Also described is a method for increasing a level of 6-deoxocathasterone in a plant. The method includes a) introducing into a plant cell an isolated polynucleotide described herein, e.g., comprising a nucleic acid molecule encoding a polypeptide having about 85% or greater sequence identity to the amino acid sequence set forth in SEQ ID NO:2; and (b) producing a transgenic plant from the transformed plant cell, where the transgenic plant exhibits an increased level of 6-deoxocathasterone.

In another aspect, a method for decreasing a level of campestanol in a plant is provided. The method includes: a) introducing into a plant cell an isolated polynucleotide described herein, e.g., comprising a nucleic acid molecule encoding a polypeptide having about 85% or greater sequence identity to the amino acid sequence set forth in SEQ ID NO:2, to produce a transformed plant cell; and (b) producing a transgenic plant from the transformed plant cell, where the transgenic plant exhibits a decreased level of campestanol.

In yet another aspect, a method for increasing a photosynthetic rate of a plant is provided which includes (a) introducing into a plant cell an isolated polynucleotide described herein, e.g., comprising a nucleic acid molecule encoding a polypeptide having about 85% or greater sequence identity to the amino acid sequence set forth in SEQ ID NO:2, to produce a transformed plant cell; and (b) producing a transgenic plant from the transformed plant cell, where the transgenic plant exhibits an increased photosynthetic rate.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1 demonstrates the alignment between *Arabidopsis thaliana* DWF4 and *Oryza Sativa* DWF4 at the amino acid level. The two sequences are 69% identical to each other. The locations of the membrane anchor, proline-rich, O2-binding, steroid-binding, function unknown, and heme-binding domains are shown by the underscores 1 through 6 respectively. Identical amino acids are blocked out in the darker gray shade.

DETAILED DESCRIPTION OF THE INVENTION

Figure 2:
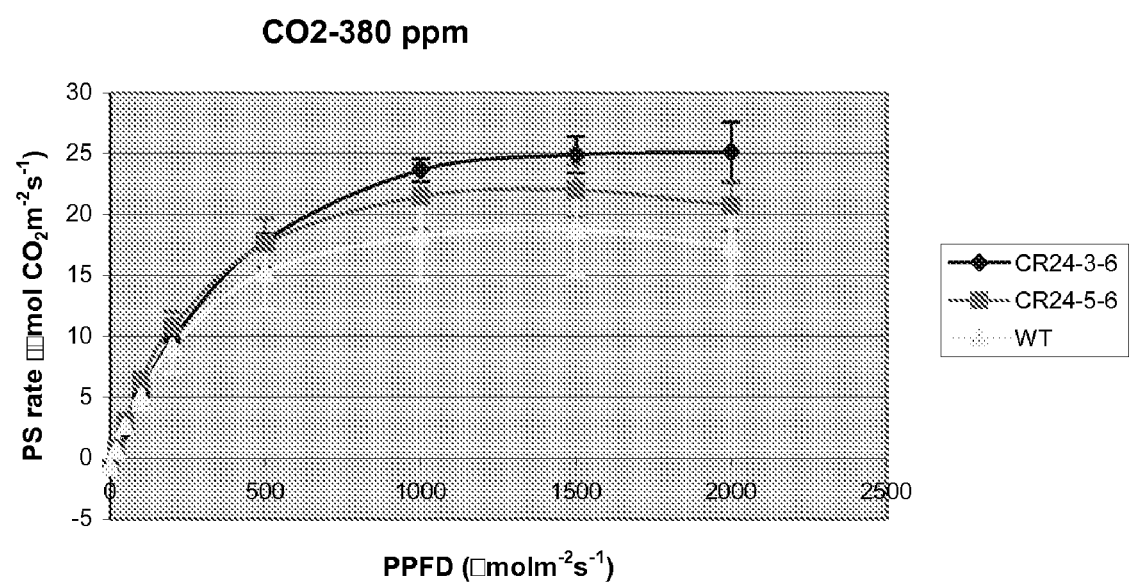
FIG. 2 is a graph showing a comparison of the photosynthetic rates (PS) at different light intensities between transgenic plants described herein and controls. PS rates were measured on the intact flag leaf at a CO2 concentration of 380 ppm, temperature of 25° C., and light intensities of 0, 20, 50, 100, 200, 500, 1000, 1500, 2000 μmol m-2s-1. The PS rate at each light point represents average of 3 plants. Bars represent standard deviation.

Constitutive Promoter: Promoters referred to herein as "constitutive promoters" promote detectable levels of transcription of an operably linked sequence in all plant tissues under most, but not necessarily all, environmental conditions and states of development or cell differentiation. Examples of constitutive promoters include the cauliflower mosaic virus (CaMV) 35S transcript initiation region, *Arabidopsis* promoters p13879 and p32449, the 1' or 2' promoter derived from T-DNA of *Agrobacterium tumefaciens*, and other transcription initiation regions from various plant genes, such as the maize ubiquitin-1 promoter.

Broadly Expressing Promoter: A promoter can be said to be "broadly expressing" as used herein when it promotes transcription in many, but not all, plant tissues. For example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. In certain cases, a broadly expressing promoter operably linked to a sequence can promote transcription of the linked sequence in a plant shoot at a level that is at least two times (e.g., at least 3, 5, 10, or 20 times) greater than the level of transcription in root tissue or a developing seed. In other cases, a broadly expressing promoter can promote transcription in a plant shoot at a level that is at least two times (e.g., at least 3, 5, 10, or 20 times) greater than the level of transcription in a reproductive tissue of a flower. In view of the above, the CaMV 35S promoter is not considered a broadly expressing promoter. Examples of broadly expressing promoters for use in the present invention include p326, YP0158, YP0214, YP0380, PT0848, PT0633, YP0050, YP0144 and YP0190.

Domain: Domains are fingerprints or signatures that can be used to characterize protein families and/or parts of proteins. Such fingerprints or signatures can comprise conserved: (1) primary sequence; and/or (2) secondary structure; and/or (3) three-dimensional conformation. Generally, a domain can be associated with a family of proteins or motifs. Typically, these families and/or motifs have been correlated with specific in vitro and/or in vivo activities. A domain can be any length, including the entirety of the sequence of a protein. Detailed descriptions of cytochrome $P_{450}$ domains, associated families and motifs, and correlated activities of the polypeptides of the instant invention are described below. As described herein, polypeptides having one or more designated domain(s) exhibiting a particular percentage of sequence identity with another polypeptide can exhibit at least one biochemical activity that is exhibited by the other polypeptide, or can affect a plant phenotype in a similar manner.

Endogenous: The term "endogenous," within the context of the current invention refers to any polynucleotide, polypeptide or protein sequence which is a natural part of a cell or an organism regenerated from said cell.

Exogenous: "Exogenous" refers to a polynucleotide that has been introduced into the genome of a host cell or an organism by any means other than a sexual cross. Typically, an exogenous polynucleotide is stably integrated into the genome of a host cell or organism. Examples of means by which a polynucleotide can be introduced into plants and plant cells are described below, and include *Agrobacterium*-mediated transformation, biolistic methods, electroporation, in planta techniques, and the like. A plant containing the exogenous nucleic acid can be referred to here as a $T_1$ plant for the primary transgenic plant, a $T_2$ plant for the first generation, and $T_3$, $T_4$, etc. for second and subsequent generation plants. $T_2$ progeny are the result of self-fertilization of a $T_1$ plant. $T_3$ progeny are the result of self-fertilization of a $T_2$ plant. It will be appreciated that an exogenous polynucleotide may have been introduced into a progenitor and not into the cell or plant under consideration. For example, a transgenic plant containing an exogenous nucleic acid can be the progeny of a cross between a stably transformed plant and a non-transgenic plant. Such progeny are considered to contain the exogenous polynucleotide. Accordingly, $BC_1$, $BC_2$, and $BC_3$ plants as well as $F_1$, $F_2$, and $F_3$ plants can similarly contain exogenous polynucleotides.

Functionally Comparable Polypeptides This phrase describes those polypeptides that have at least one characteristic in common. Such characteristics include sequence similarity or identity, biochemical activity, transcriptional pattern similarity, and phenotypic activity. Typically, functionally comparable proteins share some sequence similarity or identity. Within this definition, homologs and orthologs are considered to be functionally comparable. In addition, functionally comparable proteins can share at least one biochemical activity. For example, functionally comparable polypeptides can be "biochemical comparables," e.g., can act on the same reactant to give the same product. A biochemical comparable may or may not exhibit the same kinetics, affinity to the reactant, or turnover time to produce the product, but can still be considered functionally comparable because the same end product is produced.

Another class of functionally comparable polypeptides are "phenotypic comparables" that affect the same physical characteristic, such as increased plant size or height or altered metabolic profile. Polypeptides can be considered phenotypic comparables even if the polypeptides affect the same physical characteristic, but to a different degree. For example, comparable polypeptides affect the same characteristic (e.g., to result in increased height) where the quantitative measurement due to one of the comparable polypeptides is about 20% or more of the other; e.g., about 20 to 30%; about 30 to 40%; about 40 to 50%; about 50-60%; about 60 to 70%; about 70 to 80%; about 80 to 90%; or about 90 to 100%. Thus, two polypeptides can be phenotypic comparables although one protein increases plant height by 10% and the other increases plant height by 15%.

Gene: The term "gene," as used in the context of the current invention, encompasses all regulatory and coding sequence contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes comprised of "exons" (coding sequences), which may be interrupted by "introns" (non-coding sequences), encode proteins. A gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, artificial chromosome, plasmid, vector, etc., or as a separate isolated entity.

Heterologous sequences: "Heterologous sequences" are those that are not operatively linked and/or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from are considered heterologous to the coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel-manner are heterologous.

Homologous: In the current invention, "homologous" refers e.g., to a gene, nucleic acid, polynucleotide, or polypeptide that shares some degree of sequence similarity or identity with a gene, nucleic acid, polynucleotide, or polypeptide of interest. This similarity may be in only a fragment of the sequence and can represents a domain (e.g., a structural or functional domain). The biochemical activities or phenotypic effects of homologous entities are not necessarily the same or similar, although they can be.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the Arabidopsis gene encoding a serine-threonine kinase enzyme, and which promoter is induced by dehydration, abscissic acid and sodium chloride (Wang and Goodman, Plant J. 8:37 (1995)). Examples of environmental conditions that may affect transcription by inducible promoters include anaerobic conditions, elevated temperature, or the presence of light.

Operably linked: A control element "operably linked" to a coding sequence is joined to that coding sequence in such a way that expression of the coding sequence is achieved under conditions compatible with the control elements. The control elements need not be contiguous with the coding sequence. Thus, for example, intervening untranslated yet transcribed sequences can be present between a promoter and a coding sequence such that the promoter is "operably linked" to the coding sequence.

Orthologous: In the current invention "orthologous" refers to a second nucleic acid that encodes a gene product or polypeptide that performs a similar biochemical activity or affects a phenotype in a similar manner as the product of the first nucleic acid. The ortholog typically will also have a degree of sequence similarity or identity to the first nucleic acid. Thus, an orthologous nucleic acid may encode a polypeptide that exhibits a degree of sequence similarity to a polypeptide encoded by a first nucleic acid. The sequence similarity can be found within one or more functional and/or structural domains or along the entire length of the coding sequence of the nucleic acids and/or their corresponding polypeptides.

Percent sequence identity: In general, the term "identity" refers to exact nucleotide-to-nucleotide or amino acid-to-amino acid correspondence of two polynucleotides or polypeptides, respectively. Two or more sequences (polynucleotide or polypeptide) can be compared by determining their "percent sequence identity." As used herein, the term "percent sequence identity" refers to the degree of identity between any given query sequence and a subject sequence. A percent identity for any query nucleic acid or amino acid sequence, e.g., a C22-$\alpha$ hydroxylase, relative to a subject nucleic acid or amino acid sequence can be determined as follows.

A query nucleic acid or amino acid sequence is aligned to one or more subject nucleic acid or amino acid sequences using the computer program ClustalW, which allows alignments of nucleic acid or protein sequences to be carried out across their entire length (global alignment). ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: G,P,S,N,D,Q,E,R,K; residue-specific gap penalties: on.

The output is a sequence alignment, that reflect the relationship between sequences. ClustalW can be run, for example, at the Baylor College of Medicine (BCM) Search Launcher site on the world wide web at searchlauncher.bcm.tmc.edu/multi-align/multi-align.html or at the European Bioinformatics Institute site on the world wide web at ebi.ac.uk/clustalw.

To determine a percent identity between a query sequence and a subject sequence, ClustalW divides the number of matching bases or amino acids by the number of bases or amino acids of the shorter sequence, and multiplies the result by 100. The output is the percent identity of the subject sequence with respect to the query sequence. For example, if a query sequence and a subject sequence were each 500 base pairs long and had 200 matched (or identical) bases, the subject would have 40 percent sequence identity to the query sequence. If the two compared sequences are of different lengths, the number of matches is divided by the shorter of the two sequence lengths. For example, if 100 amino acids are matched between a 400 query polypeptide and a 500 amino acid subject polypeptide, the subject polypeptide would have 25 percent identity to the query polypeptide. If the shorter sequence is less than 150 bases or 50 amino acids in length, the number of matches are divided by 150 (for nucleic acid bases) or 50 (for amino acids), and multiplied by 100 to obtain a percent identity.

In some embodiments, the amino acid sequence of a suitable subject polypeptide has greater than 40% sequence identity (e.g., >40%, >50%, >60%, >70%, >75%, >80%, >85%, >86%, >87%, >88%, >89%, >90%, >91%, >92%, >93%, >94%, >95%, >96%, >97%, >98%, or >99% sequence identity) to the amino acid sequence of a query polypeptide (e.g., SEQ ID NOS: 2 and 3). In some embodiments, the nucleotide sequence of a suitable subject nucleic acid has greater than 70% sequence identity (e.g., >75%, >80%, >85%, >90%, >91%, >92%, >93%, >94%, >95%, >96%, >97%, >98%, or >99% sequence identity) to the nucleotide sequence of the query nucleic acid.

It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Plant Promoter: A "plant promoter" is a promoter capable of initiating (promoting) transcription in plant cells. Such promoters need not be of plant origin. For example, promoters derived from plant viruses, such as the CaMV35S promoter, or from Agrobacterium tumefaciens such as the T-DNA promoters, can be plant promoters. A typical example of a plant promoter of plant origin is the maize ubiquitin-1 (ubi-1) promoter. Other plant promoters are also known to those of ordinary skill in the art.

Promoter: The term "promoter," as used herein, refers to a region of sequence determinants located upstream from the start of transcription of a gene and which are involved in recognition and binding of RNA polymerase and other proteins to initiate and modulate transcription. A basal promoter is the minimal sequence necessary for assembly of a transcription complex required for transcription initiation. Basal promoters frequently include a "TATA box" element usually located between 15 and 35 nucleotides upstream from the site of initiation of transcription. Basal promoters also sometimes include a "CCAAT box" element (typically a sequence CCAAT) and/or a GGGCG sequence, usually located between 40 and 200 nucleotides, preferably 60 to 120 nucleotides, upstream from the start site of transcription.

Regulatory Sequence: The terms "regulatory sequence" and "control element" are used interchangeably and refer to any nucleotide sequence that influences transcription or translation initiation and rate, and stability and/or mobility of the transcript or polypeptide product. Regulatory sequences include, but are not limited to, promoters, promoter control elements, protein binding sequences, 5' and 3' UTRs, transcriptional start site, termination sequence, polyadenylation sequence, introns, certain sequences within a coding sequence, etc.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$-5° C. to $T_m$-10° C. Medium or moderate stringency conditions are those providing $T_m$-20° C. to $T_m$-29° C. Low stringency conditions are those providing a condition of $T_m$-40° C. to $T_m$-48° C. The relationship of hybridization conditions to $T_m$ (in ° C.) is expressed in the mathematical equation:

$$T_m=81.5-16.6(\log_{10}[Na^+])+0.41(\% \, G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log\{[Na^+]/(1+0.7[Na^+])\}+0.41(\% \, G+C)-500/L0.63(\% \, formamide) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

Translational start site: In the context of the current invention, a "translational start site" is usually an ATG in the cDNA transcript, more usually the first ATG. A single cDNA, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

Untranslated region (UTR): A "UTR" is any contiguous series of nucleotide bases that is transcribed, but is not translated. These untranslated regions may be associated with particular functions such as increasing mRNA message stability. Examples of UTRs include, but are not limited to polyadenylation signals, terminations sequences, sequences located between the transcriptional start site and the first exon (5' UTR) and sequences located between the last exon and the end of the mRNA (3' UTR).

Vector: By vector is meant any genetic element, such as a plasmid, phage, transposon, cosmid, chromosome, virus, etc. which is capable of transferring polynucleotide sequences to target cells. Generally, a vector is capable of replication when associated with the proper control elements. Thus, the term includes cloning and expression vehicles, as well as viral vectors and integrating vectors.

Nucleic Acid or Polynucleotide As used herein, the terms "nucleic acid" or "polynucleotide" are used interchangeably and refer to both RNA and DNA, including cDNA, genomic DNA, synthetic (e.g., chemically synthesized) DNA, and DNA (or RNA) containing nucleic acid analogs. Polynucleotides can have any three-dimensional structure, and can be in the sense or antisense orientation. Nonlimiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

Isolated nucleic acid molecules can be produced by standard techniques. For example, polymerase chain reaction (PCR) techniques can be used to obtain an isolated nucleic acid containing a nucleotide sequence described herein. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length (e.g., 10, 15, 20, 25, 27, 34, 40, 45, 50, 52, 60, 65, 70, 75, 82, 90, 102, 150, 200, 250 nucleotides in length). General PCR techniques are described, for example in *PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis, 1992, *Genetic Engineering News*, 12: 1; Guatelli et al., 1990, *Proc. Natl. Acad. Sci.* USA, 87: 1874-1878; and Weiss, 1991, *Science*, 254: 1292.

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, a reference nucleic acid sequence be mutated using standard techniques including oligonucleotide-directed mutagenesis and site-directed mutagenesis through PCR. See, *Short Protocols in Molecular Biology*, Chapter 8, Green Publishing Associates and John Wiley & Sons, Edited by Ausubel, F. M et al., 1992.

Nucleic acid analogs can be modified at the base moiety, sugar moiety, or phosphate backbone to improve, for example, stability, hybridization, or solubility of the nucleic acid. Modifications to the backbone include the use of uncharged linkages (e.g., methyl phosphonates, phosphotriesters, phosphamidates, carbamates, etc.) and charged linkages (e.g., phosphorothioates, phosphorodithioates, etc.). Modifications to the backbone can also incorporate peptidic linkages, e.g., to result in a PNA-type linkage. Modifications at the base moiety include deoxyuridine for deoxythymidine, and 5-methyl-2'-deoxycytidine or 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See Summerton and Weller, *Antisense Nucleic Acid Drug Dev.* (1997) 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone. The nucleic acid can be double-stranded or single-stranded (i.e., a sense or an antisense single strand).

As used herein, "isolated," when in reference to a nucleic acid or polynucleotide, refers to a nucleic acid or polynucleotide that is separated from other nucleic acid or polynucleotide molecules that are present in a genome, e.g., a plant genome, including nucleic acids or polynucleotides that normally flank one or both sides of the nucleic acid or polynucleotide in the genome. The term "isolated" as used herein with respect to nucleic acids or polynucleotides also includes any non-naturally-occurring sequence, since such non-naturally-occurring sequences are not found in nature and do not have immediately contiguous sequences in a naturally-occurring genome.

An isolated nucleic acid or polynucleotide can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Polypeptide The term "polypeptide" is used in its broadest sense to refer to a compound of two or more subunit amino acids, amino acid analogs, or other peptidomimetics. The subunits may be linked by peptide bonds or other bonds, for example, ester, ether, etc. The term "amino acid" refers to either natural and/or unnatural or synthetic amino acids, including the D/L optical isomers. Full-length proteins, analogs, mutants, and fragments thereof are encompassed by this definition.

By "isolated," with respect to a polypeptide, it is meant that the polypeptide is separated to some extent from the cellular components with which it is normally found in nature. An isolated polypeptide can yield a single major band on a non-reducing polyacrylamide gel. In certain cases, a polypeptide is "purified." The term "purified" as used herein preferably means at least about 75% by weight or more (e.g., at least 80%, 85%, 90%, 95%, 97%, 98%, 99%, or 100%) of polypeptides of the same type are present relative to all polypeptides in, e.g., a mixture. Isolated polypeptides can be obtained, for example, by extraction from a natural source, by chemical synthesis, or by recombinant production in a host cell or transgenic plant.

To recombinantly produce polypeptides, a nucleic acid sequence containing a nucleotide sequence encoding the polypeptide of interest can be ligated into an expression vector and used to transform a bacterial, eukaryotic, or plant host cell (e.g., insect, yeast, mammalian, or plant cells). In bacterial systems, a strain of *Escherichia coli* such as BL-21 can be used. Suitable *E. coli* vectors include the pGEX series of vectors that produce fusion proteins with glutathione S-transferase (GST). Depending on the vector used, transformed *E. coli* are typically grown exponentially, then stimulated with isopropylthiogalactopyranoside (IPTG) prior to harvesting. In general, expressed fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Alternatively, 6×His-tags can be used to facilitate isolation.

In eukaryotic host cells, a number of viral-based expression systems can be utilized to express polypeptides. A nucleic acid encoding a polypeptide of the invention can be cloned into, for example, a baculoviral vector such as pBlueBac (Invitrogen, Carlsbad, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides of the invention can be identified by standard methodology.

Mammalian cell lines that stably express polypeptides can be produced by using expression vectors with the appropriate control elements and a selectable marker. For example, the pcDNA3 eukaryotic expression vector (Invitrogen, Carlsbad, Calif.) is suitable for expression of polypeptides in cell such as, Chinese hamster ovary (CHO) cells, COS-1 cells, human embryonic kidney 293 cells, NIH3T3 cells, BHK21 cells, MDCK cells, ST cells, PK15 cells, or human vascular endothelial cells (HUVEC). In some instances, the pcDNA3 vector can be used to express a polypeptide in BHK21 cells, where the vector includes a CMV promoter and a G418 antibiotic resistance gene. Following introduction of the expression vector, stable cell lines can be selected, e.g., by antibiotic resistance to G418, kanamycin, or hygromycin. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

In yet other cases, plant cells can be transformed with a recombinant nucleic acid construct to express the polypeptide, as described previously and in the Examples, below. The polypeptide can then be extracted and purified using techniques known to those having ordinary skill in the art.

Polynucleotides and Polypeptides

The polynucleotides described herein are of interest because transgenic plants including them can exhibit altered phenotypic characteristics relative to a control plant. For example, a transgenic plant can exhibit an altered metabolic profile. An altered metabolic profile can include modified levels of sucrose, glutamate, or linoleic acid, as discussed below. In some cases, transgenic plants can exhibit an increased level of 6-deoxocathasterone, and/or a decreased level of campestanol. In some cases, a transgenic plant expressing such a polypeptide can exhibit an increased photosynthetic rate.

These altered phenotypic traits can be used to exploit or maximize plant products. For example, a polynucleotide and/or polypeptide of the present invention can be used to increase the levels of sucrose, glutamate, or linoleic acid in a plant; or to increase the levels of 6-deoxocathasterone in a plant; or to decrease the levels of campestanol in a plant; or to increase the photosynthetic rate of a plant. In certain cases, more than one phenotypic trait is modified, e.g., an increased level of 6-deoxocathasterone and a decreased level of campestanol. As a consequence, transgenic plants can have improved growth potential with increased biomass, height, seed yield, seed weight, or improved seed fill. Thus, the polynucleotides and polypeptides are useful in the preparation of transgenic plants having particular application in the agricultural and forestry industries.

In particular, isolated $P_{450}$ polynucleotide and polypeptide sequences, including polynucleotide sequence variants, homologs, orthologs, fusions, and fragments, and functionally comparable polypeptides to $P_{450}$ polypeptides are provided. An isolated $P_{450}$ polynucleotide or polypeptide can be a homo log and/or an ortholog to an *Arabidopsis* Dwf4 polynucleotide or DWF4 polypeptide. An isolated $P_{450}$ polynucleotide or polypeptide can be a homolog and/or an ortholog to a polynucleotide encoding a 22-α hydroxylase or a 22-α-hydroxylase polypeptide. Thus, isolated Dwf4 polynucleotide and DWF4 polypeptide sequences, including functionally comparable DWF4 polypeptides to *Arabidopsis* DWF4, are described herein. DWF4 is a cytochrome $P_{450}$ polypeptide that, among other activities, catalyzes the hydroxylation of campestanol at C-22 to produce 6-deoxocathasterone. Accordingly, in certain cases, a polypeptide sequence can exhibit a biochemical activity or affect a plant phenotype in a manner similar to a DWF4 polypeptide and represents a biochemical or phenotypic functionally comparable polypeptide to the *Arabidopsis* DWF4 protein.

Polynucleotides of the invention include nucleic acids that encode cytochrome $P_{450}$ polypeptides. SEQ ID NOs: 1-3 set forth the polynucleotide and polypeptide sequences of three $P_{450}$ proteins from *Arabidopsis*, corn, and rice, respectively. The *Arabidopsis* and rice sequences are DWF4 polypeptides that encode a 22-α hydroxylase enzyme. The corn polypeptide (SEQ ID NO:2) was identified as a DWF4 ortholog through sequence comparisons of a library of corn polypeptide sequences against a number of polypeptide databases, including a $P_{450}$, a plant, and a proprietary database and through evaluation of phenotypic traits of transgenic plants expressing the corn polypeptide (SEQ ID NO:2) relative to transgenic plants expressing the *Arabidopsis* DWF4 polypeptide (SEQ ID NO: 1) or the rice DWF4 polypeptide (SEQ ID NO:3). See the Examples, below, and FIG. 1, setting forth an alignment between the *Arabidopsis* DWF4 polypeptide and the rice DWF4 polypeptide.

Homologs, orthologs, fragments, fusions, complements, or reverse complements of the described polynucleotides (and encoded polypeptides) are also contemplated. As noted above, homologs and orthologs of a polypeptide can be referred to as functionally comparable polypeptides. Functionally comparable polypeptide homologs exhibit particular levels of sequence identity to the corn polypeptide sequence set forth in SEQ ID NO:2. For example, an isolated polynucleotide can include a nucleic acid encoding a polypeptide having about 85% or greater sequence identity to the amino acid sequence set forth in SEQ ID NO:2, e.g., about 86, 87, 90, 92, 95, 96, 97, 98, 99, or 100% sequence identity. A functionally comparable protein can be an ortholog to *Arabidopsis* DWF4. A functionally comparable protein can be an ortholog of a polypeptide having C-22 α-hydroxylase activity. FIG. 8 sets forth the polypeptide sequences for a number of orthologs of *Arabidopsis* DWF4.

In some cases, the polynucleotide further includes a broadly expressing promoter operably linked to the nucleic acid encoding the polypeptide. Any broadly expressing promoter can be used, including, without limitation, the ones described further herein.

In certain cases, a polypeptide described herein can be an orthologous functionally comparable protein to *Arabidopsis* DWF4 as determined by the polypeptide performing at least one of the biochemical activities of DWF4 or affecting a plant phenotype in a similar manner to DWF4. Thus, a polypeptide can catalyze a similar reaction as DWF4 or affect a plant phenotype in a manner similar to DWF4. For example, *Arabidopsis* DWF4 is known to catalyze the oxidation of campestanol at C-22 to form 6-deoxocathasterone. DWF4 also catalyzes the hydroxylation of 6-oxocampestanol to produce cathasterone. A polypeptide of the invention may also perform one or both of these enzymatic steps.

In certain cases, a functionally comparable polypeptide exhibits at least 60% of a biochemical activity of the *Arabidopsis* DWF4 protein, e.g., at least 70%, 80%, 90%, or 95% of a biochemical activity. Methods for evaluating biochemical activities are known to those having ordinary skill in the art, and include enzymatic assays (e.g., to evaluate $V_{max}$, $K_m$, $K_{cat}$, $K_i$, etc.), radiotracer feeding assays, etc. In particular, levels of substrate and product for a given enzymatic step can be evaluated using analytical techniques known to those having ordinary skill in the art (e.g., GC-MS). For example, levels of chemical intermediates in the BL pathway can be evaluated in transgenic plants that include a polynucleotide encoding a polypeptide described herein. Levels can be compared relative to levels in a control plant. Levels of chemical intermediates in transgenic plants can be evaluated at various stages in development, e.g., seedling or adult stages, or using various tissues (e.g., seeds, leaves, shoots, stem, flower, etc.). A decrease in the level of campestanol and/or an increase in the level of 6-deoxocathasterone can be indicative that a polypeptide is an ortholog to *Arabidopsis* DWF4.

Recombinant Vectors and Host Cells

The invention also provides recombinant vectors and host cells that include any of the isolated polynucleotides described above. As indicated more fully below, a variety of recombinant vectors are well known to those having ordinary skill in the art. A recombinant vector can include a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also include a marker gene that confers a selectable phenotype on plant cells. The marker typically encodes biocide resistance, particularly antibiotic resistance, such as resistance to kanamycin, G418, bleomycin, hygromycin, or herbicide resistance, such as resistance to chlorosulfuron or phosphinotricin.

Typically, a recombinant vector will include a polynucleotide and a control element operably linked to the polynucleotide so that a polypeptide coding sequence in the polynucleotide can be transcribed and translated, e.g., in a host cell. A control element can be a promoter, many of which are known to those of skill in the art. For example, a plant promoter can be included, such as one that directs transcription of the gene in all or certain tissues of a regenerated plant, e.g., a constitutive promoter such as 35S or a broadly expressing promoter such as p326. In such cases, the promoter is operably linked to the nucleic acid encoding the polypeptide of interest. Alternatively, the plant promoter can direct transcription of a sequence of the invention in a specific tissue (tissue-specific promoters) or is otherwise under more precise environmental control (inducible promoters). As indicated previously, various plant promoters, including constitutive, tissue-specific, broadly expressing, and inducible promoters, are known to those skilled in the art and can be utilized in the present invention. A polyadenylation region at the 3'-end of the coding region can also be included. The polyadenylation region can be derived from the natural gene, from various other plant genes, or from T-DNA.

In certain cases, a broadly expressing promoter can be included. For example, broadly expressing promoters such as p326, YP0158, YP0214, YP0380, PT0848, PT0633, YP0050, YP0144 and YP0190 can be used. In such cases, a polynucleotide operably linked to a broadly expressing promoter can be any of the polynucleotides described above, e.g., those that include nucleic acids that encode SEQ ID NO:s 1-3, or a polynucleotide including a nucleic acid sequence encoding a polypeptide exhibiting at least about 85% (e.g., at least about 86%, 87%, 90%, 92%, 95%, 96%, 97%, 98%, 99% or 100%) sequence identity to SEQ ID NOs: 1-3. In cases where a constitutive promoter such as 35S is employed, a polynucleotide can include a nucleic acid encoding a polypeptide-having 85% or greater sequence identity to the amino acid sequence set forth in SEQ ID NO:2 (e.g., about 86, 87, 90, 92, 95, 96, 97, 98, 99, or 100% sequence identity, provided that the encoded polypeptide does not exhibit 93% or greater (e.g., 94, 94.5, 95, 95.5, 96, 97, 98, 99 or 100%) sequence identity to the amino acid sequences set forth in SEQ ID NO: 1 or SEQ ID NO:3.

Recombinant vectors can be used to transform a variety of plant cells for preparing transgenic plants. Techniques for transforming a wide variety of higher plant species are known in the art. Typically, recombinant DNA constructs are prepared that include the polynucleotide sequences of the invention inserted into a vector that is suitable for transformation of plant cells. The construct can be made using standard recombinant DNA techniques (Sambrook et al. 1989). The vector backbone can be any of those typical in the art such as plasmids, viruses, artificial chromosomes, BACs, YACs and PACs.

Transgenic Plants

The invention also provides transgenic plants that include an exogenous polynucleotide or recombinant vector as described herein. Any of the polynucleotides or recombinant vectors described previously can be introduced into the genome of a variety of plant hosts by a number of known methods, including electroporation, microinjection, and biolistic methods. Alternatively, the polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA; electroporation of plant tissues, and microprojectile bombardment.

Ectopic expression of the sequences of the invention can be accomplished using a "knock-in" approach. Here, the first component, an "activator line," is a transgenic plant comprising a transcriptional activator operatively linked to a promoter. The second component comprises the desired cDNA sequence operatively linked to the target binding sequence/region of the transcriptional activator. The second component is transformed into the "activator line" or is used to transform a host plant to produce a "target" line that is crossed with the "activator line" by ordinary breeding methods. In either case, the result is the same. That is, the promoter drives production of the transcriptional activator protein that then binds to the target binding region to facilitate expression of the desired cDNA.

Any promoter that functions in plants can be used in the first component, such as a constitutive promoter, a tissue or organ specific promoter, or a broadly expressing promoter, as described previously. Suitable transcriptional activator polypeptides include, but are not limited to, those encoding HAP1 and GAL4. The binding sequence recognized and targeted by the selected transcriptional activator protein is used in the second component.

Transformed plant cells produced by the above methods can be cultured to regenerate a plant which possesses the transformed genotype. Regeneration techniques can rely on manipulation of phytohormones in tissue culture growth media, and may rely on a biocide and/or herbicide marker introduced with the polynucleotide of interest. Regeneration can also be obtained from plant protoplasts, callus, explants, organs, pollens, embryos, or parts thereof.

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. Methods include Southern analysis and PCR amplification (e.g., for detection of a polynucleotide); Northern blots, S1 RNase protection, primer-extension, or RT-PCR amplification for detecting and examining RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining can also be used to detect the presence or expression of polypeptides and/or polynucleotides. Methods for performing all of the referenced techniques are well known. After a polynucleotide is stably incorporated in a transgenic plant, it can be introduced into other plants by sexual crossing, e.g., by standard breeding techniques.

The polynucleotides described above can be used to transform a number of plants and plant cell systems, including monocotyledonous and dicotyledonous plants. The polynucleotides and polypeptides will find particular application in the agricultural and forestry areas. A suitable group of plant species includes dicots, such as safflower, alfalfa, soybean, coffee, rapeseed (high erucic acid and canola), or sunflower. Also suitable are monocots such as corn, wheat, rye, barley, oat, rice, millet, amaranth, switchgrass, or sorghum. Vegetable crops or root crops such as lettuce, carrot, onion, broccoli, peas, sweet corn, popcorn, tomato, potato, beans (including kidney beans, lima beans, dry beans, green beans) and the like are suitable, as well as fruit crops such as grape, strawberry, pineapple, melon (e.g., watermelon, cantaloupe), peach, pear, apple, cherry, orange, lemon, grapefruit, plum, mango, banana, and palm.

Thus, the methods described herein can be utilized with dicotyledonous plants belonging to the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Methods described herein can also be utilized with monocotyledonous plants belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales, or with plants belonging to Gymnospermae, e.g., Pinales, Ginkgoales, Cycadales and Gnetales.

The invention has use over a broad range of plant species, including species from the genera *Allium, Alseodaphne, Anacardium, Arachis, Asparagus, Atropa, Avena, Beilschmiedia, Brassica, Citrus, Citrullus, Capsicum, Catharanthus, Carthamus, Cocculus, Cocos, Coffea, Croton, Cucumis, Cucurbita, Daucus, Duguetia, Elaeis, Eschscholzia, Ficus, Fragaria, Glaucium, Glycine, Gossypium, Helianthus, Heterocallis, Hevea, Hordeum, Hyoscyamus, Lactuca, Landolphia, Linum, Litsea, Lolium, Lupinus, Lycopersicon, Malus, Manihot, Majorana, Medicago, Musa, Nicotiana, Olea, Oryza, Panicum, Pannesetum, Papaver, Parthenium, Persea, Phaseolus, Pinus, Pistachia, Pisum, Pyrus, Prunus, Raphanus, Rhizocarya, Ricinus, Secale, Senecio, Sinomenium, Sinapis, Solanum, Sorghum, Stephania, Theobroma, Trigonella, Triticum, Vicia, Vinca, Vitis, Vigna* and *Zea*.

A suitable group of species with which to practice the invention include alkaloid producing plants, e.g, plants from the Papaveraceae, Berberidaceae, Lauraceae, Menispermaceae, Euphorbiaceae, Leguminosae, Boraginaceae, Apocynaceae, Asclepiadaceae, Liliaceae, Gnetaceae, Erythroxylaceae, Convolvulaceae, Ranunculaeceae, Rubiaceae, Solanaceae, and Rutaceae families. The Papaveraceae family, for example, family contains about 250 species found mainly in the northern temperate regions of the world and includes plants such as California poppy and Opium poppy. Useful genera within the Papaveraceae family include the *Papaver* (e.g., *Papaver bracteatum, Papaver orientale, Papaver setigerum,* and *Papaver somniferum*), *Sanguinaria, Dendromecon, Glaucium, Meconopsis, Chelidonium,* Eschscholzioideae (e.g., *Eschscholzia, Eschscholzia california*), and *Argemone* (e.g., *Argemone hispida, Argemone mexicana*, and *Argemone munita*) genera. Other alkaloid producing species with which to practice this invention include *Croton salutaris, Croton balsamifera, Sinomenium acutum, Stephania cepharantha, Stephania zippeliana, Litsea sebiferea, Alseodaphne perakensis, Cocculus laurifolius, Duguetia obovata, Rhizocarya racemifera,* and *Beilschmiedia oreophila*.

Another suitable group of species with which to practice the invention include terpenoid producing plants, e.g, plants from the genera *Aesculus, Anamirta, Andrographis, Artemisia, Betula, Bixa, Cannabis, Centella, Chrysanthemum, Tanacetum, Cinnamomum, Citrullus, Luffa, Coleus, Curcuma, Cymbopogan, Daphne, Euphorbia, Glycine, Glycyrrhiza, Gossypium, Guayule, Hevea, Isodon, Rabdosia, Rabdosia, Mentha, Salvia, Rosmarinus, Simarouba, Taxus, Thymus*, and *Tripterygium*.

Other suitable species include *Lycopersicum esculentum, Nicotiana* spp. (e.g., *Nicotiana tabacum*), *Capsicum* spp. (including *C. annuum*), *Parthenium argentatum* Gray, *Mentha spicata, M. pulegium, M. piperita, Thymus vulgaris* L., *Origanum vulgare, Rosmarinus officinalis, Melissa officinalis, Theobroma cacao, Lavandula augustifolia, Salvia officinalis, Coffea arabica, Hevea benthamiana, Hevea guianensis, Hevea brasiliensis, Manihot glaziovii, Manihot dichotoma, Castilla elastica, Ficus elastica, Funtimia elastica, Landolphia kirkii, Landolphia gentilli, Landolphia heudelotii, Landolphia owariensis, Crytostegia grandiflora, Crytostegia madagascariansis, Taraxacum megalorhizon, Palaquim gutta, Manilkara bidentata,* and *Manilkara zapata*.

In certain cases, a transgenic plant is not an *Arabidopsis thaliana* or *Nicotiana tabacum* plant. In some cases, a transgenic plant is not a member of the Solanaceae family or of the Brassicaceae family. For example, a transgenic plant may not be an *Arabidopsis thaliana* or *Nicotiana tabacum* plant when it comprises at least one exogenous polynucleotide, where the at least one exogenous polynucleotide includes a nucleic acid encoding a polypeptide:

(a) having about 85% or greater sequence identity to the amino acid sequence set forth in SEQ ID NO:2.

Transgenic plants can exhibit any of the biochemical activities of the polypeptides described above. For example, a transgenic plant can exhibit at least one of the biochemical activities of *Arabidopsis* DWF4, e.g., 22 α-hydroxylase activity. Methods for evaluating biochemical activities are known to those having ordinary skill in the art; see, e.g., above.

Transgenic plants can be used to yield a plant having an altered plant phenotype (e.g., as compared to a control plant). A polypeptide can affect the phenotype of a plant (e.g., a transgenic plant) when expressed in the plant, e.g., at the appropriate time(s) or in the appropriate tissue(s). Phenotypic effects are typically evaluated relative to a control plant that does not express the exogenous polynucleotide of interest, such as a corresponding wild type plant, a corresponding plant not transgenic for the exogenous polynucleotide of interest but otherwise isogenic to the transgenic plant of interest, or a corresponding isogenic plant in which expression of the polypeptide is suppressed, inhibited, or not induced (i.e., when expression is under the control of an inducible promoter). A plant can be said "not to express" a polypeptide when the plant exhibits less than 10% (e.g., less than 9%, 8%, 7%, 6%, 5%, 4%, 3%, 2%, 1%, 0.5%, 0.1%, 0.01%, 0.001%) of the amount of polypeptide or mRNA encoding the polypeptide exhibited by the plant of interest. Expression can be evaluated by methods known to those having ordinary skill in the art, e.g., RT-PCR amplification, Northern blots, S1 RNAse protection, primer extensions, Western blots; protein gel electrophoresis, immunoprecipitation, enzyme-linked immunoassays, chip assays, and mass spectrometry. It should be noted that if a polypeptide is expressed under the control of a tissue-specific or broadly expressing promoter, expression can be evaluated in the entire plant or selectively in a desired tissue. Similarly, if a polypeptide is expressed at a particular time, e.g., at a particular time in development or upon induction, expression can be evaluated selectively at a desired time period.

A phenotypic effect can be an altered metabolic profile relative to a control plant. For example, a transgenic plant can exhibit increased levels of one or more of the following metabolites: sucrose, glutamate (glutamic acid), or linoleic acid. In certain cases, when a polypeptide described herein is expressed in a transgenic plant, the transgenic plant can exhibit a sucrose concentration (e.g., in leaf tissue) that is from 10% to about 30% greater (e.g., about 12 to about 30%; about 15 to about 25%, about 18 to about 25%, or about 10 to about 20% greater) than a plant not expressing the polypeptide. In some cases, when a polypeptide described herein is expressed in a transgenic plant, the transgenic plant can exhibit a glutamic acid concentration (e.g., in leaf tissue) that is from about 10% to about 65% greater (e.g., about 10 to about 30%; about 20 to about 45%; about 30 to about 60%; about 40 to about 65%; about 30 to about 55%; about 20 to about 30% greater) than a plant not expressing the polypeptide. In yet other cases, when a polypeptide described herein is expressed in a transgenic plant, the transgenic plant can exhibit a linoleic acid concentration (e.g., in a leaf tissue) that is from about 10% to about 50% greater (e.g., about 15% to about 35%; about 20% to about 45%; about 30% to about 48%; about 15 to about 35% greater) than a plant not expressing the polypeptide. Transgenic plants can in certain cases not exhibit an increase in the level of certain other amino acids, carbohydrates, fatty acids and organic acids relative to a control plant, e.g., certain compounds shown in Table 3.

A phenotypic effect can be an increased photosynthetic rate relative to a control plant. Methods for measuring photosynthetic rates are known to those having ordinary skill in the art for a given plant species. For example, a transgenic plant can exhibit an increased photosynthetic rate at a certain temperature, light intensity (e.g., photosynthetic photon flux density (PPFD)), humidity, or carbon dioxide concentration relative to a control plant. A temperature for evaluating photosynthetic rates can be from about 5° C. to about 45° C., or any value therebetween (e.g., about 10° C., about 20° C., about 25° C., about 30° C., or about 32° C.). Humidity values can range from about 5% to about 80%, or any value therebetween (e.g., about 10%, about 20%, about 30%, about 40%, about 50%, about 55%, about 60%, or about 70%). Light intensity (PPFD) can be from about 0 $\mu mol\ m^{-2}s^{-1}$ to about 4000 $\mu mol\ m^{-2}s^{-1}$, or any value therebetween (e.g., 25, 50, 100, 200, 300, 400, 500, 600, 700, 800, 900, 1000, 1100, 1200, 1300, 1400, 1500, 1600, 1700, 1800, 1900, 2000, 2200, 2500, 2750, 2900, 3000, 3200, 3400, 3600, 3800, or 3900 $\mu mol\ m^{-2}s^{-1}$). Carbon dioxide concentrations can range from about 25 ppm to about 1000 ppm, or any value therebetween, e.g., about 50, about 75, about 100, about 200, about 300, about 360, about 380, about 400, about 500, about 600, about 700, about 760, about 800, about 900, or about 950 ppm). Any combination of temperatures, light intensities, humidity, and carbon dioxide concentrations can be used. For example, in some cases, a transgenic plant can exhibit an increased photosynthetic rate relative to a control plant at a carbon dioxide concentration of 360 ppm, a humidity level of about 50-55%, a temperature of about 25° C., over the range of PPFDs from about 1000 to about 2000 $\mu mol\ m^{-2}s^{-1}$.

A phenotypic effect can be an increase or decrease in a level of a chemical intermediate in the BL pathway. For example, a phenotypic effect can be an increase in 6-deoxocathasterone levels relative to a control plant. A phenotypic effect can be a decrease in campestanol levels relative to a control plant. Analytical methods for measuring chemical intermediates, including intermediates in the BL pathway such as campestanol and 6-deoxocathasterone, are known in the art and are also described herein. An increase or decrease can be any amount relative to a control plant, e.g., a greater than 1.2 fold, 1.5 fold, 1.8 fold, 2 fold, 3 fold, 4 fold, 5 fold, 6 fold, 8 fold, 10 fold, 50 fold, or 100 fold increase or decrease relative to a control plant. In certain cases, an increase in 6-deoxocathasterone can be greater than 2 fold, or greater than 3 fold, or greater than 4 fold, or greater than 5 fold, or greater than 6 fold, relative to a control plant.

Transgenic plants can also exhibit increased growth potential, increased size (e.g., height), increased seed yield, more uniform seed fill (e.g., in monocots such as rice), a more rapid rate of growth, or improved drought tolerance relative to a control plant. For example, when a polypeptide described herein is expressed in a transgenic plant, the transgenic plant can exhibit a height that is from about 7% to about 20% greater (e.g., about 10% to about 15%; about 12% to about 18%; about 8% to about 18%; about 15% to about 20 greater) than a plant not expressing the polypeptide. In other cases, when a polypeptide described herein is expressed in a transgenic plant, the transgenic plant can exhibit a seed yield (number of seeds per plant) from about 10% to about 95% greater (e.g., from about 10% to about 20%; from about 10% to about 50%; from about 10% to about 70%; from about 20% to about 60%; from about 20% to about 75%; from about 25% to about 85%; from about 30% to about 70%; from about 35% to about 90%; from about 40% to about 60%; from about 40% to about 85%; from about 50% to about 80%; from about 50% to about 90%; from about 70% to about 90% greater) than a plant not expressing the polypeptide. In certain cases, when a polypeptide described herein is expressed in a transgenic plant, the transgenic plant can exhibit an increase in seed weight per plant from about 5% to about 20% greater (e.g., from about 5% to about 10%; from about 8% to about 12%; from about 10% to about 15%; from about 8% to about 18% greater) than a plant not expressing the polypeptide.

It should be noted that phenotypic effects are typically evaluated for statistical significance by analysis of one or more experiments. It is understood that when comparing phenotypes to assess the effects of a polypeptide, a difference in phenotypes is considered statistically significant at $p \leq 0.05$ with an appropriate parametric or non-parametric statistic, e.g., Chi-square test, Student's t-test, Mann-Whitney test, or F-test.

Other phenotypic effects can be evaluated by methods known to those of ordinary skill in the art, including cell length measurements at specific times in development; measurements of BL usage; sterol detection assays; detection of reaction products or by-products; detection of levels of substrate and/or product for a given enzymatic step; and dose-response tests on putative enzymatic substrates.

Methods

Polynucleotides and polypeptides described herein can be used to generate plants having an altered phenotype, e.g., altered phenotypic characteristics. Thus, methods for altering one or more phenotypic characteristics of a plant are provided. A phenotypic characteristic can be one or more of an altered metabolic profile; an altered photosynthetic rate; an increase in a level of 6-deoxocathasterone; a decrease in a level of campestanol; an increased seed yield; an increased seed weight per plant; and an increased height relative to a control plant. A method described herein typically can include a) introducing into a plant cell an isolated polynucleotide that includes a nucleic acid molecule encoding a polypeptide having about 85% or greater sequence identity to the amino acid sequence set forth in SEQ ID NO:2, in order to produce a transformed plant cell; and (b) producing a transgenic plant from the transformed plant cell. The resultant plants can be evaluated for an altered phenotypic characteristic using any methods, including those described herein. In certain cases, more than one phenotypic characteristic may be altered, e.g., an increase in 6-deoxocathasterone levels and a decrease in campestanol.

Altering Expression Levels of DWF4 Polypeptides

Overexpression

As described previously, the polynucleotides, recombinant vectors, host cells, and transgenic plants described herein can be engineered to yield overexpression of a polypeptide of interest. Overexpression of a polypeptide can be used to alter plant phenotypic characteristics relative to a control plant, e.g., a control plant not expressing the polypeptide, such as to increase plant height, to alter metabolic profiles, to increase the levels of 6-deoxocathasterone, to decrease the level of campestanol, to increase photosynthetic rates, or to improve seed yield, etc. In addition, a polypeptide can be overexpressed in combination with overexpression of another polypeptide, e.g., another $P_{450}$ polypeptide involved in the BL biosynthetic pathway, such as CPD. Such co-expression of polypeptides can result in additive or synergistic effects on a plant biochemical activity (e.g., enzymatic activity) or phenotype (e.g., height). Fusion polypeptides can also be employed and will typically include a polypeptide described herein fused in frame with another polypeptide, such as a polypeptide involved in BL biosynthesis (e.g., CPD).

Inhibition of Expression

Alternatively, the polynucleotides and recombinant vectors described herein can be used to suppress or inhibit expression of an endogenous $P_{450}$ protein, such as DWF4, in a plant species of interest. A number of methods can be used to inhibit gene expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Catalytic RNA molecules or ribozymes can also be used to inhibit expression. Ribozymes can be designed to specifically pair with virtually any target RNA and cleave the phosphodiester backbone at a specific location, thereby functionally inactivating the target RNA. The inclusion of ribozyme sequences within ribozymes confers RNA-cleaving activity upon them, thereby increasing their suppression activity. Methods for designing and using target RNA-specific ribozymes are known to those of skill in the art. See, generally, WO 02/46449 and references cited therein.

Methods based on RNA interference (RNAi) can also be used. RNA interference is a cellular mechanism to regulate the expression of genes and the replication of viruses. This mechanism is mediated by double-stranded small interfering RNA molecules (siRNA). A cell responds to a foreign double-stranded RNA (e.g., siRNA) introduced into the cell by destroying all internal mRNA containing the same sequence as the siRNA.

RNAi is believed to include both initiation and effector steps. In the initiation step, input dsRNA is digested into 21-23 nucleotide small interfering RNAs (siRNAs), which have also been called "guide RNAs." The siRNAs are produced when the enzyme Dicer, a member of the RNase III family of dsRNA-specific ribonucleases, processively cleaves dsRNA (e.g., introduced directly or via a transgene or virus) in an ATP-dependent, processive manner. Successive cleavage events degrade the RNA to 19-21 bp duplexes (siRNAs), each with 2-nucleotide 3' overhangs. In the effector step, the siRNA duplexes bind to a nuclease complex to form the RNA-induced silencing complex, or RISC. An ATP-depending unwinding of the siRNA duplex is required for activation of the RISC. The active RISC targets the homologous transcript by base pairing interactions and cleaves the mRNA approximately 12 nucleotides from the 3' terminus of the siRNA.

Methods for designing and preparing siRNAs to target a target mRNA are known to those of skill in the art; see, e.g., WO 99/32619 and WO 01/75164. In one method of design, a scan for AA dinucleotide sequences is made beginning with the AUG start codon of the target transcript. Each AA sequence and the 3' adjacent 19 nucleotides are recorded as potential siRNA target sites. Two to four such sequences can then be selected, based in part on the following criteria:

1) siRNAs with 30-50% GC content are more active than those with a higher G/C content;

2) since a 4-6 nucleotide poly(T) tract acts as a termination signal for RNA pol III, stretches of greater than 4 T's or A's in the target sequence should be avoided when designing sequences to be expressed from an RNA pol III promoter;

3) since some regions of mRNA may be highly structured or bound by regulatory proteins, it may be useful to select siRNA target sites at different positions along the entire length of the gene; and 4) it may be useful to compare the potential target sites to the appropriate genome database (human, mouse, rat, etc.) and eliminate from consideration any target sequences with more than 16-17 contiguous base pairs of identity to other coding sequences that are not of interest.

In some embodiments, an interfering RNA construct includes a sequence that is transcribed into a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

Chemical synthesis, in vitro transcription, siRNA expression vectors, and PCR expression cassettes can then be used to prepare the designed siRNA.

Articles of Manufacture

The invention also provides articles of manufacture. An article of manufacture can include a transgenic plant described herein, e.g., a transgenic plant in a container, bag, pot, or planter. An article of manufacture can include one or more seeds from a transgenic plant described herein. Typically, a substantially uniform mixture of seeds is conditioned and bagged in packaging material by means known in the art to form an article of manufacture. Such a bag of seed preferably has a package label accompanying the bag, e.g., a tag or label secured to the packaging material, a label printed on the packaging material, or a label inserted within the bag. The package label may indicate that plants grown from such seeds are suitable for making an indicated preselected polypeptide. The package label also may indicate that the seed contained therein incorporates transgenes that may provide desired phenotypic traits, as discussed above.

EXAMPLES

Example 1

Analysis of p326:DWF4 Expression in Rice on Plant Growth and Development

A Ti plasmid containing a promoter designated p326 upstream of and operably linked to a Hap1 coding sequence, and $UAS_{Hap1}$ (Hap1 upstream activating sequence) operably linked to a green fluorescence protein (GFP) coding sequence, was introduced in to the rice cultivar Kitaake by utilizing *Agrobacterium* and transformation-competent callus. Expression of the Hap1 coding sequence results in the accumulation of Hap1 protein and GFP. Detectable expression of GFP was confined to the stem and leaves of rice plants, with lesser expression observed in root tissues. Expression was not detected in shoot meristem, flowers, or seeds prior to gemmination. A line derived from this transformation event was designated CRS-BIN1A 7.

A Ti plasmid containing five copies of the $UAS_{Hap1}$ upstream of and operably linked to the genomic coding sequence for an *Arabidopsis* 22-α hydroxylase (DWF4) was also introduced into Kitaake. The gDNA was from ecotype WS. Activation of the UAS (by Hap1) resulted in transcription of the DWF4 gDNA and accumulation of DWF4 transcript.

T2 UAS:DWF4 lines derived from independent transgenic lines 17 and 36 and designated 17-3, 36-5, and 36-6, were pollinated by CRS-BIN1A 7 plants to produce F1 seeds. The three groups of F1 plants for 17-3, 36-5, and 36-6 progeny were termed R150, R149 and R147, respectively. F1 plants were tested for the presence of Hap1:GFP by fluorescence, and for the presence of the UAS:DWF4 by PCR. The presence of DWF4 gDNA transcript was confirmed by RT-PCR. F2 seeds from F1 plants designated R150P5, R150P7, R149P2 and R149P5 were germinated and grown side-by-side in 5 pots with negative controls, as shown in Table 1.

TABLE 1

Table 1. Pairing of Plants for Phenotyping. Each pair contains one F1 plant containing p326:Hap1 and UAS:DWF4 and one F1 control plant containing p326:Hap1 or UAS:DWF4, growing in the same pot.

| F1 Abbreviation | p326:Hap1 | UAS:DWF4 | Pair |
|---|---|---|---|
| R150P5 | Present | Present | 1 |
| R150P2 | Present | Absent | |
| R150P7 | Present | Present | 2 |
| R150P6 | Absent | Present | |
| R149P2 | Present | Present | 3 |
| R149P6 | Absent | Present | |
| R147P5 | Present | Present | 4 |
| R147P2 | Present | Absent | |

Measurements of leaf length, leaf width, internode length, stem thickness, panicle thickness, branch number, seed number, and seed weight were used to assess the effects of enhanced DWF4 activity on growth, development and yield. Measurements of leaves showed that the sheath and blade were approximately 15% longer in F1 plants containing p326:Hap1 and UAS:DWF4 and enhanced DWF4 activity than the leaves of control plants, and that the length of the first internode was increased significantly as a result. The width of the leaf blade may also have been decreased somewhat, although the variation in the data made any differences non-significant. The combined effect of these DWF4-induced changes was an approximately 15% increase in height, and the effect on the internode length made the leaves slightly clustered towards the top of the plant. There were no obvious changes in leaf texture. However, leaf angle was increased in plants containing p326:Hap1 and UAS:DWF4 and showing enhanced DWF4 activity. The lengths of the sheath and of the blade were also increased in F1 plants showing enhanced levels of DWF4 transcript when grown separately, and the leaves of these plants were darker green.

The number of tillers on F1 plants containing p326:Hap1 and UAS:DWF4 and showing enhanced DWF4 activity (approximately 11 tillers) was the same as the number of tillers on control plants containing p326:Hap1 only or UAS:DWF4 only. However, measurements of several parameters relating to seed yield revealed consistent differences. The number of F2 seeds per tiller and per plant, and the seed weight per plant, were both increased by 20-30% in F1 plants containing p326:Hap1 and UAS:DWF4 and showing enhanced DWF4 activity. Also, the weights of the seeds was increased: F2 seeds from plants containing p326:Hap1 and UAS:DWF4 and showing enhanced DWF4 activity were approximately 10% heavier than in control plants.

Measurements of tiller number and seed number were taken 95 days after transplanting to soil (at harvest). For the measurements of seed weight, seeds were collected 95 days after transplanting to soil and dried for 14 days at 37° C. All plants made approximately 11 tillers: tiller number is unchanged by enhanced DWF4 activity. However, the numbers of seeds per tiller and the number of seeds per plant were increased by 20-30%, and weight per seed was increased by approximately 10%. The combination of these effects was an increase seed weight per plant (yield) of up to approximately 30%. There was a difference in seeds per tiller, seed per plant, seed weight per seed and seed weight per plant of greater than one standard deviation. The data demonstrate that expression of a dicot 22-α hydroxylase in a monocot results in heavier seeds.

One hundred F2 seeds selected at random were weighed from each of the same four pairs of plants and seed weights from heaviest to lightest were displayed. The data revealed that the increase in seed weight was most prominent in the smallest approximately 30% of the seeds. In three out of four pairs (pairs 2-4), seed weight was increased by up to approximately 40% in the lightest approximately 30% of the seeds from plants containing elevated levels of DWF4, relative to the control plants growing in the same pots. In the other approximately 70%, seed weight was increased by lesser amounts. In one out of four pairs (pair 1), seed weight was increased evenly among all classes of seed. These results indicate that a 22-α hydroxylase confers more uniform seed fill when expressed vegetatively in a monocot.

The width of the stem base and the width of the panicle base were also measured. The width of the stem was increased by up to approximately 30% in plants containing p326:Hap1 and UAS:DWF4 relative to control plants containing p326:Hap1 only or UAS:DWF4 only, whereas the width of the panicle was increased by up to approximately 20%. Therefore, expression of DWF4 in rice resulted in an increase in plant height and seed yield, but also an increase in the thickness of the axis sufficient to support the increased plant height and seed yield. Visual observation indicated the plants were not prone to lodging.

These data indicate that vegetative expression of a 22-α hydroxylase in a monocot, in the absence of expression of the hydroxylase in inflorescences and developing seeds, provides increased seed yield.

Example 2

Analysis of p326:DWF4 Expression in Rice on Metabolite Levels

UAS:DWF4 lines DWF4-BIN1B 16-2, 17-3 and 27-3, derived from the independent transgenic lines 16, 17 and 27, respectively, were pollinated by CRS-BIN1A 7 plants to produce F1 seeds. The three groups of F1 plants, termed R148, R150 and R151, respectively, were tested for the presence of Hap1:GFP by fluorescence, and for the presence of the UAS:DWF4 by PCR. The presence of DWF4 gDNA transcript was confirmed by RT-PCR. F2 seeds from F1 plants designated R148P5, R150P7 and R151P1 were germinated and grown in the dark for 3 days, and then tested for the presence of p326:Hap1 and UAS:DWF4. Five pairs of GFP(+)/DWF4(+) and GFP(+)/DWF4(−) segregants, each arising from the same F1 plant, were grown side-by-side in 5 pots, as shown in Table 2.

TABLE 2

Table 2. Pairing of Plants. GFP(+)/DWF4(+) and GFP(+)/DWF4(−) F2 segregants were grown side-by-side. Hap1:GFP and UAS:DWF4 signify the two elements of the 2-component system.

| T2 Abbreviation | Hap1:GFP | UAS:DWF4 | Pair |
|---|---|---|---|
| R148P5-13 | Present | Absent | 1 |
| R148P5-12 | Present | Present | |
| R148P5-14 | Present | Absent | 2 |
| R148P5-15 | Present | Present | |
| R150P7-14 | Present | Absent | 3 |
| R150P7-19 | Present | Present | |
| R150P7-18 | Present | Absent | 4 |
| R150P7-20 | Present | Present | |
| R151P1-41 | Present | Absent | 5 |
| R151P1-40 | Present | Absent | |

F2 plants were grown in the greenhouse. The flag leaf from each plant was collected about 12 days after initiation of flowering and within 5 minutes of the other flag leaves (between 5:00 pm and 5:05 pm), frozen on dry ice, and stored at −80° C. For chemical analysis, these leaves were lyophilized, extracted with methanol and dichloromethane, and partitioned into polar and non-polar phases before derivatization and gas chromatography-mass spectrometry (GC-MS). Extractions were done in duplicate or triplicate to generate replicate samples for GC-MS analysis. The amount of lyophilized leaf tissue used for each extraction is shown in Table 3.

TABLE 3

Table 3. Samples used for MxP Analysis. The T2 abbreviation refers to each of the 10 flag leaves used for GC-MS analysis. Columns '1', '2' and '3' show the amount of lyophilized leaf tissue used for each extraction, in mg. For two of the flag leaves (R148P5 14 and R151P1 40), there was only enough tissue for duplicate extractions.

| T2 Abbreviation | 1 | 2 | 3 |
|---|---|---|---|
| R148P5 13 | 28.9 | 29.1 | 30.1 |
| R148P5 12 | 29.8 | 29.7 | 32.0 |
| R148P5 14 | 29.9 | 28.6 | — |
| R148P5 15 | 29.5 | 29.2 | 22.7 |
| R150P7 14 | 29.3 | 30.0 | 29.6 |
| R150P7 19 | 28.6 | 30.2 | 30.0 |
| R150P7 18 | 31.2 | 29.6 | 30.4 |
| R150P7 20 | 29.7 | 30.0 | 27.4 |
| R151P1 41 | 28.9 | 27.4 | 28.5 |
| R151P1 40 | 29.5 | 19.2 | — |

Data collection and processing involved visual inspection and comparison of chromatograms, multivariate analysis including principal component analysis (PCA) and hierarchical clustering analysis (HCA), and experimental/control analysis. The data collection and processing were used to determine metabolite ratios. Eighty-two compounds were analyzed, including amino acids, carbohydrates, fatty acids and organic acids. The compounds analyzed are shown in Table 4.

TABLE 4

Table 4. Compounds Analyzed by GC-MS (MxP). For fatty acids, the ratios refer to the number of carbon atoms and the number of unsaturated bonds.

| | | |
|---|---|---|
| L-Alanine | Fumaric Acid | Xylitol/Arabitol |
| Glycine | Succinic Acid | Mannitol |
| L-Valine | Citramalic Acid | Inositol |
| L-Leucine | Malic Acid | Maltitol |
| L-Isoleucine | 2-Hydroxybenzoic Acid | Undecanoic Acid |
| L-Serine | Ribonic Acid-g-Lactone 1 | Caprylic Acid ME (C8:0) |
| L-Proline | a-Ketoglutaric Acid | Capric Acid ME (C10:0) |
| L-Threonine | Quinic Acid | Lauric Acid ME (C12:0) |
| Homoserine | Shikimic Acid | Myristic Acid ME (C14:0) |
| trans-4-L-Hydroxyproline | Citric Acid | Palmitic Acid ME (C16:0) |
| L-Aspartic Acid | Isocitric Acid | Stearic Acid ME (C18:0) |
| L-Methionine | 3-Phosphoglyceric Acid | Oleic Acid ME (C18:1) |
| L-Cysteine | Gluconic Acid | Linoleic Acid ME (C18:2) |
| L-Glutamic Acid | Xylose/Arabinose | Linolenic Acid ME (C18:3) |
| L-Glutamine | Fucose 1 | Behenic Acid ME (C22:0) |
| L-Phenylalanine | Fructose 1 | Lignoceric Acid ME (C24:0) |
| L-Asparagine | Mannose | 1-Tetradecanol |
| L-Ornithine | Galactose 1 | Hexadecanol |
| L-Lysine | Glucose 1 | 1-Octadecanol |
| L-Histidine | Sucrose | 1-Docosanol |
| L-Tryptophan | Maltose 1 | 1-Octacosanol |
| DL-Lactic Acid | Trehalose | 1-Triacontanol |
| Glycolic Acid | Isomaltose 1 | Squalene |
| Pyruvic Acid | Raffinose | Cholesterol |
| Oxalic Acid | Gycerol | Stigmasterol |
| Phosphoric Acid | Erythritol | Sitosterol |
| Glyceric Acid | Ribitol ISTD | Campesterol |
| Benzoic Acid | | |

The results of the metabolic profiling analysis showed that the levels of free sucrose were increased by about 20% in 2 out of 5 plants containing p326:Hap1 and UAS:DWF4 (GFP(+)/DWF4(+) plants) relative to controls containing p326:Hap1 alone (GFP(+)/DWF4(−) plants). Sucrose concentrations in the other 3 plants were also higher than the concentration in controls, although the increases were not statistically significant.

The results also showed that the concentration of glutamic acid and linoleic acid were increased in the flag leaves of all 5 F2 plants relative to controls. The increase for glutamic acid was between about 15% and about 65%. The increase for linoleic acid was between about 18% and about 40%. The concentrations of other amino acids, carbohydrates, other fatty acids and organic acids were not significantly different relative to controls.

Example 3

DWF4 Antisense

An experiment was carried out in which a CaMV35S promoter was operably linked to an *Arabidopsis* DWF4 antisense polynucleotide. The construct was introduced into *Arabidopsis* and the resulting transgenic plants were found to exhibit repressed elongation under shade conditions, relative to a corresponding plant that lacked the construct.

Example 4

Expression of a Corn 22-α Hydroxylase in Kitaake Rice Using a 35S promoter

A construct having a nucleic acid encoding SEQ ID NO:2 operably linked to a CaMV35S promoter was made, and introduced into Kitaake rice plants. T2 plants exhibit increased height relative to a control plant lacking the construct.

Example 5

Expression of an Indica Rice 22-α Hydroxylase in *Arabidopsis* Using p326 or 35S Promoters A cDNA clone (SEQ ID NO: 16) from Indica rice was identified whose amino acid sequence is 69% identical to the amino acid sequence of *Arabidopsis* DWF4. This clone was designated OsDWF4. Utilization of the p326 and 35S promoters to express OsDWF4 in *Arabidopsis* resulted in a series of phenotypes similar to those observed when p326:DWF4 and 35S:DWF4, respectively, are expressed in *Arabidopsis*. These phenotypes include elongation of the hypocotyl, petiole and inflorescence. In addition, OsDWF4 was introduced into *Arabidopsis* semi-dwarf plants. The semi-dwarf phenotype of these plants results from expression of aDWF4 antisense sequence (DWF4a/s). Expression of OsDWF4 in such plants corrected the semi-dwarf phenotype, indicating that DWF4 and OsDWF4 are functional orthologs.

Identification of DWF4 Homologs

BLAST analysis of the *Arabidopsis* DWF4 sequence (Genbank AF044216) identified a Japonica rice clone, Genbank AC104473 (locus id AAN60994). The Japonica clone was 69% identical to that of *Arabidopsis* DWF4 (Genbank AF044216) at the amino acid level. Indica rice SEQ ID NO: 16 was found to contain a C-to-T substitution at position 539 relative to the Japonica rice clone Genbank AC104473. The C-to-T substitution at position 539 results in a leucine at position 180 in the Indica sequence.

The *Arabidopsis* DWF4 amino acid sequence and the Indica rice amino acid sequence are >85% identical within three of the major domains (domain A, domain B and the heme binding domain), but are 21% identical in the membrane anchor domain, as shown in Table 5.

TABLE 5

Amino Acid Sequence Identities. The numbers describe the sequence identity between DWF4 and OsDWF4. Domain A is the $O_2$-binding domain. Domain B is the steroid-binding domain. Domain C has an unknown function. Domains A through C and the heme-binding domain serve important functions for DWF4 and are highly conserved. The anchor and hinge regions are less well conserved.

| Whole Protein | | | | | | | |
|---|---|---|---|---|---|---|---|
| Identical | Similar | Anchor | Hinge | A | B | C | Heme |
| 69.00% | 80.00% | 21.00% | 71.40% | 94.10% | 92.30% | 76.90% | 88.20% |

Transformation and Transgenic Plant Lines

The DWF4 coding sequence was operably linked to the p326 promoter and was introduced into a Ti plasmid vector. The OsDWF4 sequence (SEQ ID NO:16) was operably linked to p326 and 35S promoters and each construct was introduced into a Ti plasmid vector. p326 confers strong, broad expression throughout most cells and tissues except the cells of the apical meristem and flowers, with somewhat lower expression in roots. The 35S promoter confers essentially constitutive expression. The Ti vectors contained a selectable marker for Basta® resistance.

Constructs were introduced into *Arabidopsis* WS plants using floral infiltration. SR01370 lines contained p326:DWF4, SR01334 lines contained p326:OsDWF4 and SR01390 and SR01392 lines contained p35S:OsDWF4. T2 plants containing the herbicide resistant selectable marker and a DWF4 transgene were identified by painting herbicide onto leaves and by PCR, respectively. T2 segregants containing single T-DNA insertions were identified by studying segregation ratios.

TABLE 6

| Line Designation | Construct |
|---|---|
| SR01370 | p326:DWF4 |
| SR01334 | p326:OsDWF4 |
| SR01390 | p35S:OsDWF4 |
| SR01392 | p35S:OsDWF4 |
| SR01219 | p35S:DWF4a/s |
| SR01557 | p35S:DWF4a/s and p326:OsDWF4 |
| SR01159 | YP0009:DWF4 |
| SR01130 | YP0104:DWF4 |
| SR01187 | YP0126:DWF4 |
| BinD 1-11 | p13879:DWF4 |
| SR 1029-6 | p13879:ANT |

Phenotyping

Phenotypes of SR01370, SR01334 and SR01390/SR01392 plants were noted visually at the T1 generation. For lines showing possible phenotypic differences, at least 18 T2 plants per T1 parent were analyzed by measuring root length at 4 days after germination (DAG) and hypocotyl length, rosette diameter, plant height, silique length and weight starting at 13 DAG. T2 wild-type segregants, untransformed wild-types and other T1 lines containing other unrelated cDNAs were used as controls. Cell size was observed by using a Leica TCS SP2 scanning laser confocal microscope to image the chlorophyll autofluorescence arising from the cells of the inflorescence stem 15 cm from the tip.

T1 Phenotypes

Three 6 SR01370 lines showed elongated petioles and slightly curled leaves relative to other T1 lines containing other cDNAs at 34 DAG. These phenotypes are characteristic of DWF4 gDNA phenotypes, suggesting that p326:DWF4 transgenes were also affecting brassinolide levels. Similar phenotypes were evident in 10 out of 10 independent SR01334 lines and in 18 out of 20 SR01390 lines at 20 and 40 DAG respectively.

T2 Phenotypes p326 and 35S express strongly in *Arabidopsis* seedlings. DWF4 and OsDWF4 transgenes resulted in elongated hypocotyls in T2 seedlings when compared with untransformed wild-type seedlings at the same stage of development. Measurements of hypocotyls length in 10 plants per line at 13 DAG indicated that T2 SR01370-2 and SR01370-5, SR01334-2 and SR01334-4, and SR01390-7/SR01392-5 hypocotyls were up to twice as long as hypocotyls in untransformed wild-types, and t-test analysis showed that the variation was significant at the 0.05 level for all lines. The effect on the hypocotyls was less pronounced for SR01370-2 and SR01370-5 than for SR01334-2 and SR01334-4, suggesting that the heterologous OsDWF4 transgene has a stronger effect on hypocotyl development than the *Arabidopsis* DWF4 gene itself For measurements later in development, 18 T2 plants per T1 were grown in a greenhouse and segregants genotyped by utilizing PCR. Elongated petioles and slightly curled leaf blades were observed in all T2 lines containing p326:DWF4 (SR01370-1 and SR01370-2), p326:OsDWF4 (SR01334-2 and SR01334-4), and 35S:OsDWF4 (SR01390-7/SR01392-5) at 21 DAG. Measurements indicated that T2 plants containing each of the transgenes were >7% greater in diameter than wild-type segregants by 4 days after bolting. Student's t-test analysis showed that the variation was significant at the 0.05 level for some of the lines ($P_{1334-2}=0.0467$, $P_{1334-4}=0.063$, $P_{1370-1}=0.221$, $P_{1370-2}=0.0022$, $P_{1390-7}=0.064$, $P_{1392-5}=0.0053$). Although the T2 population was a mixed population containing homozygotes as well as heterozygotes, the increased diameter of DWF4 transgenic plants was nevertheless distinguishable from non-transgenic plants.

T2 plants were also taller than wild-types, as shown in FIG. 7. Measurements indicated that T2 SR01370-1 and SR01370-2, SR01334-2 and SR01334-4, and SR01390-7/SR01392-5 were ~9% taller than wild-type segregates at 30 DAG (FIG. 7A). Student's t-test analysis showed that the variation was significant at the 0.05 level for some lines ($P_{1334-4}=0.0008$, $P_{1370-2}=0.001$, $P_{1390-7}=0.0414$, $P_{1392-5}=0.00027$). Considering that these measurements were taken from a mixed population of homozygotes and heterozygotes, the increase in plant height would probably be more pronounced in homozygotes. Confocal microscopy of the stems of T2 plants containing DWF4 or OsDWF4 showed that the cells in the cortex 15 cm from the shoot apex were larger than in wild-type controls (data not shown).

Endogenous DWF4 transcripts and brassinolide itself accumulate to high levels in silique tissue in *Arabidopsis*. 35S and p326 promoters also promote strong expression in the walls of the siliques, so siliques in transgenic plants were examined to see if there were any additive effects on silique growth. The silique at the fifth node up from the base of the primary inflorescence was collected from each of 10 T2 plants per line at 33 DAG, and measured and weighed. Siliques from SR01370-1 and SR01370-2, SR01334-2 and SR01334-2, and SR01390-5 and SR01392-5 plants were not different in weight from those from wild-type segregants. However, siliques from plants containing each of the DWF4 transgenes were up to ~20% longer and conspicuously narrower than siliques from wild-type controls, both at the fifth node on the primary inflorescence and elsewhere on the primary and secondary inflorescences. The results indicate that expression of p326:DWF4, p326:OsDWF4, and 35S:OsDWF4 in *Arabidopsis* resulted in elongation of siliques.

Genetic Complementation of DWF4a/s

A 1.035 kb DWF4 antisense sequence (SEQ ID NO:5) was identified, corresponding to the anchor and hinge regions of the DWF4 cDNA but not domain A, domain B, domain C or the heme-binding domain. This sequence consists of 67% of the DWF4 cDNA. The 1.035 kb sequence has 39.6% sequence identity with OsDWF4 at the nucleotide level, and was designed to be unlikely to function as an antisense towards OsDWF4. The DWF4 sequence was operably linked to a 35S promoter in the antisense orientation (35S:DWF4a/s) in a Ti plasmid.

The Ti plasmid containing 35S:DWF4a/s was introduced into *Arabidopsis*, generating SR01219 plant lines. See Table 6. T2 line SR01219-24 was genotyped by PCR and shown to contain a single T-DNA. T1 and T2 SR01219 plants showed reduced stature, but were not dwarfs.

Genetic complementation was performed by introducing OsDWF4 into a DWF4a/s background. T3 35S:DWF4a/s plants homozygous for single T-DNA insertions (SR01219-24-11) were retransformed with p326:OsDWF4, generating the SR01557 line. PCR was used to confirm the presence of p326:OsDWF4, using PCR primers that amplified a sequence spanning the p326 sequence and the OsDWF4 cDNA sequence.

T1 SR01557 seedlings showing elongated hypocotyls at 8 DAG in white light, long-day (LD) conditions were screened for. Such seedlings, together with some more common short-hypocotyl seedlings, were transferred to pots, for genotyping and phenotyping. When these plants had achieved the rosette stage (at 23 DAG), they showed elongated and slightly curled leaf blades, or were wild-type in appearance. These data suggest that the semi-dwarf phenotype associated with SR01219-24-11 plants had been corrected by OsDWF4, and that the elongated hypocotyls and leaf petioles were the result of elevated levels of OsDWF4.

RT-PCR was used to examine the expression of the endogenous DWF4 transcript and the exogenous OsDWF4 transcript in SR01557 plants at 10 DAG. For RT-PCR, RNA was collected from individual plants at 32 DAG. For qRT-PCR, RNA was collected from 200 seedlings per plant line at 10 DAG. Plasmids containing DWF4, CPD and OsDWF4 sequences were used as controls in these experiments.

RT-PCR showed that all 5 T1 DWF4a/s, OsDWF4 plants contain low levels of DWF4 transcript, when compared with untransformed wild type transcript. The qRT-PCR showed that these endogenous DWF4 transcript levels were reduced by >50%, indicating that the 1.035 kb DWF4a/s is effective in partially reducing endogenous DWF4 levels. The RT-PCR showed that SR01557-4, SR01557-7 and SR01557-12 plants were expressing OsDWF4 at high levels, whereas the SR01557-2 and SR01557-3 plants were not. T1 SR01557-4 and SR01557-7 plants resulted in OsDWF4 phenotypes, whereas T1 SR01557-2 and SR01557-3 plants did not, suggesting that the OsDWF4 transcript was responsible for the corrected phenotype. PCR results also showed that the primers used to amplify DWF4 did not amplify CPD or OsDWF4, and that the primers used to amplify OsDWF4 did not amplify DWF4 and CPD, indicating that the PCR primers are specific for their respective transcripts.

These results suggest that an *Arabidopsis* DWF4 coding sequence exhibits 22 α-hydroxylase activity in rice, and can function in brassinosteroid biosynthesis, e.g., by catalyzing the formation of 6-deoxocathasterone from the substrate campestanol. The results also suggest that a rice coding sequence exhibits 22 α-hydroxylase activity in *Arabidopsis*, and can function in brassinosteroid biosynthesis, e.g., by using campestanol as a substrate and catalyzing the formation of 6-deoxocathasterone. Taken together, the results show that a dicot 22 α-hydroxylase polypeptide can be utilized in a monocot, and vice versa. Finally, the results also indicate that these hydroxylase coding sequences exhibit sufficient enzymatic activity to generate high levels of 6-deoxocathasterone in plants, and that they are functional orthologs.

Example 6

Evaluation of YP0009. YP0104, and YP0126 Promoters

Transformation and Transgenic Plant Lines

Promoters designated as YP0009, YP0104, and YP0126, when used as HAP1 fusions, stimulate the expression of UAS:GFP primarily in roots, stems, and leaves, respectively. The YP0009, YP0104, and YP0126 promoters were operably linked to a DWF4 gDNA in a Ti plasmid vector (CRS-BIN1A).

Constructs were introduced into *Arabidopsis* ecotype Ws plants using floral infiltration. SR01159 lines contained YP0009:DWF4, SR01130 lines contained YP0104:DWF4 and SR01187 lines contained YP0126:DWF4. See Table 6. T2 segregants containing single T-DNA insertions were identified and used for T2 phenotyping. Corresponding T3 plants that were homozygous for single insertions were also identified and used for qRT-PCR (for promoters affording sufficient tissue) and phenotyping.

Phenotyping

Putative T1 phenotypes were recorded and eighteen T2 plants per T1-2 events per constructs—were phenotyped. For lines showing clear phenotypes, 10 T3 plants per T2 were also phenotyped. Wild-type segregants were used as controls. Measurements of rosette size, plant height, branch number, aerial tissue dry weight, and seed weight were used to assess the effects of DWF4 transgene.

Expression of DWF4 in the Stem

In *Arabidopsis*, the YP0104 promoter expresses primarily in the epidermis and cortex of the stem. The presence of YP0104:DWF4 in SR1130 T2 lines was tested by PCR, and the plants that tested positive were phenotyped. Clear evidence of reduced plant height in each of the SR1130 lines from T1 through T3 generations was found—each of two SR1130 lines (SR1130-1-3 and 1130-5-6) were ~10% shorter than wild-type segregants, and student's t-test analysis showed that the variation was significant at the 0.05 level ($P_{1130-1-3}$=0.026, $P_{1130-5-6}$=0.038 for T2 plants; $P_{1130-1-3}$=0.038, $P_{1130-5-6}$=0.0018 for T3 plants).

Examination of T2 and T3 plants that contained YP0104:DWF4 also showed that the density of siliques on the primary inflorescence was increased relative to wild-type segregant controls. When the number of siliques in the distal 16 cm of the primary inflorescences of four T3 plants was determined, it was found to be ~11% increased relative to the controls for SR1136-1-3 and ~3% increased for SR11236-5-6; t-test analysis showed that some of this variation was significant at the 0.05 level ($P_{1130-1-3}$=0.011, $P_{1130-5-6}$=0.38). The shoot biomass and seed yield seemed to be not affected by the DWF4 transgene. Whereas the YP0104 promoter is active in the epidermis and cortex of the stem, it does not express at measurable levels in the leaves or seeds.

Expression of DWF4 in the Root

In *Arabidopsis*, the YP0009 promoter expresses primarily in the cortex and stele of the root. The presence of YP0009:DWF4 in SR1159 T2 lines was examined by PCR, and the plants that tested positive were phenotyped. Although the YP0009 promoter is active in roots, utilizing YP0009 to express a DWF4 gDNA did not result in any kind of visible phenotype, either in roots or in shoots.

Expression of DWF4 in the Shoot

In *Arabidopsis*, the YP0126 promoter expresses primarily in the epidermis and mesophyll of the shoot and the leaves. The presence of YP0126:DWF4 in SR1187 T2 lines by was examined by PCR, and qRT-PCR was performed on leaf tissue to confirm the presence of the DWF4 transcript; plants that tested positive were phenotyped. Although the YP0126 promoter is active in the leaves, utilizing YP0126 to express DWF4 GDNA did not result in a visible phenotype, either in shoots or in roots.

Constitutive expression of DWF4 tends to generate taller plants. However, these results show that a YP0104:DWF4 transgene resulted in shorter plants, and suggest that by utilizing YP0104 to express DWF4 in the epidermis and cortex of the stem, one may reduce stem height.

In comparison with YP0104, when either YP0009 to express DWF4 in roots, or YP0126 to express it in leaves, was utilized, no phenotype was seen. Promoters that express broadly or constitutively in the plant body therefore may be preferred.

Example 7

Evaluation of Promoter YP0216

Transformation and Transgenic Plant Lines

YP0216 was introduced into a Ti plasmid (CRS-BIN1A) containing a DWF4 gDNA. The promoter, when used a fusion with Hap1, stimulates the expression of UAS:GFP primarily in the apices of the stems.

Constructs were introduced into *Arabidopsis* ecotype Ws plants using floral infiltration. Ten individual transformation events, giving rise to the lines termed SR0977, were obtained. T2 lines containing single T-DNA insertions were identified by segregation analysis and T2 and T3 plants that were homozygous for these insertions were identified and used for phenotyping.

Phenotyping

Plants from two transformation events (SR0977-2 and SR0977-3), 10 T3 plants per event, were used for qRT-PCR and all phenotyping studies. Wild-type segregants were grown alongside the T2 and T3 plants as controls. Measurements of plant height, branch number, shoot dry weight, and total seed weight were used to assess the effects of the DWF4 transgene.

In *Arabidopsis*, the YP0216 promoter expresses strongly in the epidermis and cortex of the apex of the stem. The presence of YP01216 in SR0977 T2 lines was examined by PCR, and T3 homozygotes were examined for presence of transcript by qRT-PCR; the T3 plants that tested positive were phenotyped. T3 plants showed no visible morphological phenotypes when compared to wild-type segregants.

Measurements of plant height and branch number (utilizing T3 plants), and of shoot and seed weight (utilizing T2 and T3 plants) showed either that there was no difference between transgenic lines and wild-type controls, or that any significant differences were a feature of only one of the two transgenic events. For example, the shoot weight and total seed weight data showed that the difference between SR0977-2-10 plants and the wild-types that segregated from them was significant at the 0.05 level in t-test analysis (P=0.03 for shoot weight, P=0.001 for seed weight), but that there was no such difference in SR0977-3-5 plants. Therefore, the variability evident among the SR0977-2 population, although significant, was not a consistent feature of plants containing YP0216:DWF4 transgenes. Measurements of leaf number showed that there was no difference between transgenic lines and wild-type segregant controls. RT-PCR of RNA from the apical 1 cm of the stem showed that the YP0216:DWF4 transgene was expressed.

Example 8

Coexpression of DWF4 and ANT

Constitutive expression of ANT in *Arabidopsis* increases the size of a plant. ANT encodes an AP2-domain transcription factor. Constitutive expression of DWF4 in *Arabidopsis* also increases the size of a plant. Both polynucleotides were expressed in a single plant to evaluate the effects of combined expression of DWF4 and ANT on plant size.

Transformation and Transgenic Plant Lines

The constitutive promoters 35S and p13879 were used to control gene expression in all experiments. Expression of ANT using the p13879 promoter results in larger plants, probably by prolonging the period in which cells emerging from meristems continue to divide, but also causes sterility in the homozygous condition.

A DWF4 gDNA, an ANT cDNA clone designated 7098806, and a 5' ANT deletion termed ANTΔN3 (ANTΔ) were used in conjunction with 35S or p13879. The DWF4 and ANT sequences were introduced into plants using CRS-BIN1A.

Parents carrying the DWF4 and ANT transgenes were crossed to generate F1 plants expressing both genes. The p13879:DWF4 line (BinD 1-11) contained a single T-DNA, as shown below, and was used as a T3 homozygote. The p13879:ANT line (SR 1029-6) also contained a single T-DNA and was used as a heterozygote. A single p13879:ANT plant was crossed as the female to a single p13879:DWF4 plant as the male.

PCR was used to identify 5 F1 plants resulting from the cross that contained both the DWF4 and ANT transgenes, as well as another 5 that contained only the DWF4 transgene. In addition, an untransformed wild-type plant was crossed as a male to the same p13879:ANT as a female. PCR revealed 5 F1 plants that contained only the ANT transgene and another 5 that were wild-type (wild-type sibs). Together, these 20 F1 plants were used for all phenotype measurements.

Re-Transformation

Plants containing 35S:ANTΔ and an NPTII gene for kanamycin resistance were retransformed with a T-DNA construct containing p13879:DWF4 and a modified PAT gene for herbicide resistance. T1 plants that were herbicide resistant were selected, and PCR was used to re-confirm the presence of the ANT transgene. T1 plants that were both herbicide resistant and PCR-positive for NPTII were used for all phenotype measurements.

Phenotyping

Plants were grown to maturity. Measurements of rosette size, plant height, aerial tissue dry weight, branch number, seed number, and seed weight were used to assess the effects of DWF4 and ANT transgenes.

F1 plants that were PCR-positive for p13879:ANT and p13879:DWF4, and T1 plants PCR-positive for 35S:ANT and counter-selected for p13879:DWF4, showed a mixture of phenotypes. Some had elongated petioles and leaf blades, resembling 35S and p13879:DWF4 single transformants, whereas others had large rosettes and more rounded leaves, resembling p13879:ANT single transformants. The F1 plants containing p13879:DWF4 and p13879:ANT were similar in stature to control plants expressing DWF4 alone; however, 2 out of 5 plants were sterile.

These observations suggested that F1 plants had characteristics of both the DWF4 single transformants and ANT single transformants. However, there were many differences between F1 plants. For example, branch number varied from 22 to 57, possibly because of differential penetrance of the DWF4 phenotype, which is associated with increased branching. As another example, seed weight varied from 0 to 303 mg, possibly because of differential penetrance of the ANT phenotype, which is associated with sterility. The results suggested that there was reduced biomass relative to ANT controls. Similar phenotypes with similar variability were also observed in T1 plants containing p13879:DWF4 and p35S:ANTΔ.

Overall, both the F1 and the T1 plants showed elements of the ANT and DWF4 phenotypes, resulting in variable phenotypes that were a mixture of DWF4 and ANT traits rather than a sum of them.

Example 9

Evaluation of Promoters p13879 and p32449

The role of brassinolide in stress tolerance in *Arabidopsis* was investigated using transgenic plants in which the p13879 and p32449 promoters were utilized to express the DWF4 cDNA. *Arabidopsis* (Ws) lines containing one of two DWF4 constructs were used with two independent transformation events for each construct for all experiments. These constructs were p13879:DWF4 (BinD) and p32449:DWF4 (CC2). Promoters p13879 and p32449 both express in the root and shoot, especially in the epidermis, cortex and shoot meristem. All T2 lines (BinD 1-11-1, BinD 3-9-1, CC2 4-2-3, and CC2 7-2-1) contained single T-DNA insertions. T2 plants were progeny-tested to identify T2 homozygotes, and were used in all experiments. Wild-type T2 segregants not containing T-DNA insertions were used as controls. To confirm that the homozygotes contained the correct transgenes, PCR was used to genotype all four lines.

Growth Conditions and Measurements

Seeds were sown in 5×7-inch pots and grown in a growth chamber operating at 22° C., 16 h light/8 h dark, and 70% relative humidity. Plants were watered twice a week so that the total was 2.5 L water per week. For heat treatment, 14 day-old plants were transferred to a growth chamber set at 36° C., 16 h light/8 h dark, 70% relative humidity, for 3 weeks. For cold treatment, 7 day-old plants were transferred into a growth chamber set at 8° C., 16 h light/8 h dark, 70% relative humidity for 8 weeks. For drought stress, water was withheld from seedlings at day 14 for 2 weeks in growth conditions of 22° C., 16 h light/8 h dark, and 70% relative humidity.

All p13879:DWF4 and p32449:DWF4 seedlings showed the elongation of the petiole and narrowing of the leaf blade that are characteristic of elevated levels of DWF4.

Heat Treatment: T2 plants containing DWF4 transgenes showed increased sensitivity to heat stress when compared to wild-type segregants. After 18 days at 36° C. and 70% relative humidity, all T2 plants from the two p32449:DWF4 lines were completely bleached and dead. Approximately half of the plants from the two p13879:DWF4 lines were completely bleached and dead. After 21 days in these conditions, all of the p13879:DWF4 plants were dead. All wild-type plants remained green and living. These results suggest that p32449:DWF4 plants are more sensitive to heat stress than p13879:DWF4 plants.

Cold Treatment T2 plants containing DWF4 transgenes did not show altered sensitivity to cold stress when compared to wild-type segregants. After 7 weeks at 8° C. and 70% relative humidity, all plants from two independent p32449:DWF4 lines and two independent p13879 lines were indistinguishable from wild-type segregants.

Drought Treatment: T2 plants containing DWF4 transgenes did not show altered sensitivity to drought stress when compared to wild-type segregants. After growing for 2 weeks without water and in 70% relative humidity, the plants from two independent p32449:DWF4 lines and two independent p13879 lines were indistinguishable from wild-type segregants.

In addition, there was no difference in water loss rate when utilizing detached rosettes. Water loss rate is a sensitive measure of the response of a plant to drought.

The results indicated that p13879:DWF4 and p32449:DWF4 T2 lines were unaltered in resistance to cold or drought stress relative to wild-type and were more sensitive to heat stress than wild-type segregants. p32449:DWF4 seemed to have a greater effect than p13879:DWF4. The difference between these two lines may be explained by the expression patterns of the two different promoters. While p13879 and p32449 both express in many tissues and organs, transcription from p32449-linked sequences is induced by up to 8-fold under heat-shock conditions, while transcription from p13879-linked sequences is not heat-inducible. It is therefore likely that the greater sensitivity to heat stress is a result of the heat-indocility of p32449-linked sequences.

Example 10

Analysis of BL Biosynthesis Pathway Chemical Intermediates in Transgenic Plants The levels of chemical intermediates in the BL biosynthesis pathway in p326:DWF4 seedlings were measured using gas chromatography-mass spectrometry (GC-MS), and compared to the levels in untransformed wild-type control seedlings. The reaction that is catalyzed by DWF4 was enhanced in p326:DWF4 and p326:ZmDWF4 seedlings, providing strong evidence that the seed number, seed filling and seed yield phenotypes are the direct result of increased BL levels.

Materials And Methods p326:DWF4 Direct Fusion Lines

The DWF4 gDNA (SEQ ID NO: 14) and an homologous corn cDNA termed ZmDWF4 (SEQ ID NO: 15) were each operably linked to the p326 promoter and the OCS terminator, resulting in the constructs CR24 and CR26, respectively. CR24 and CR26 were transformed into rice using *Agrobacterium*-mediated transformation and homozygous lines were recovered. One hundred T4 seeds for line CR24-3-6 and for line CR26-1-6 were sterilized with 20% bleach and rinsed four times with sterile distilled water, and germinated on ½ strength MS medium supplemented with 1.5% sucrose. Seventeen day-old seedlings and untransformed wild-type control seedlings were collected and immediately ground in liquid nitrogen. The powdered samples were lyophilized for five days and shipped to the Plant Functions Lab at RIKEN (The Institute of Physical and Chemical Research), Wako-shi, Saitama 351-0198, Japan for gas chromatography-mass spectrometry (GC-MS) analysis. The fresh and the dry weight for each of the seedling samples are shown below in Table 7.

TABLE 7

Table 7. Weights of 100 Seedlings Used for BL Analysis. The numbers show weight in grams.

| Line | Fresh weight | Dry weight |
| --- | --- | --- |
| Wild-type | 23.2166 | 3.0359 |
| CR24-3-6 | 24.2097 | 3.1753 |
| CR26-1-6 | 28.231 | 4.1924 |

Measurement of Chemical Intermediates in the BL Biosynthesis Pathway

To analyze endogenous brassinosteroid (BR) intermediates in the BL biosynthesis pathway, the lyophilized samples were extracted twice with 250 mL of methanol:CHCl$_3$ (4:1 v/v) and BR intermediates purified and measured by GC-MS according to Fujioka et al. (2002) and He et al. (2003).

Results

Lyophilized T3 rice seedlings homozygous for the *Arabidopsis* DWF4 gDNA or for an homologous corn cDNA (ZmDWF4), along with equivalent material from an untransformed wild-type control, were sent to Shozo Fujioka at RIKEN. The GC-MS data are shown below in Table 8.

TABLE 8

Table 8. GC-MS Results for wild-type, CR24-3-6 and CR26-1-6 Seedlings. The numbers show levels of BR pathway intermediates in ng/g fresh weight. CN (campestanol) and 6-DeoxoCT (6-deoxocathasterone) are the substrate and product of DWF4, respectively.

| Compound | WT | CR24-3-6 | CR26-1-6 |
| --- | --- | --- | --- |
| 24MC | 5850 | 5140 | 6900 |
| CR | 99500 | 84200 | 92800 |
| CN | 2190 | 1720 | 1340 |
| 6-OxoCN | 55.4 | 53.6 | 67.5 |
| 6-DeoxoCT | 0.58 | 1.3 | 3.36 |
| 6-DeoxoTE | 0.25 | 0.18 | 0.45 |
| 6-Deoxo3DT | 2.44 | 2.16 | 5.44 |
| 6-DeoxoTY | 7.61 | 69.66 | 18.4 |
| 6-DeoxoCS | 1.14 | 1.04 | 1.98 |
| CT | nd | nd | nd |
| TE | 0.05 | 0.05 | 0.09 |
| TY | 0.68 | 0.66 | 1.23 |
| CS | 0.25 | 0.27 | 0.39 |
| BL | nd | nd | nd |

When these GC-MS data were mapped relative to the known BL biosynthetic pathway, the decrease in campestanol levels was immediately upstream of the increase in 6-deoxocathasterone levels relative to wild-type controls. These results indicate that the conversion of campestanol to 6-deoxocathasterone in the late C-6 oxidation pathway was enhanced by DWF4 transgenes.

For the CR24-3-6 plants containing p326 operably linked to the *Arabidopsis* DWF4 gDNA, there was a greater than 2-fold increase of 6-deoxocathasterone levels. There was also a slight decrease in 6-deoxoteasterone and 3-dehydro-6-deoxoteasterone levels, followed in the pathway by an increase in 6-deoxotyphasterol. DWF4 catalyzes the first rate-limiting step in the BL biosynthesis pathway and CPD catalyzes the second, so the results demonstrate that in p326: DWF4 plants, CPD becomes the rate-limiting step. It is possible that there is rapid conversion between BR intermediates downstream of CPD, so that no clear differences can be seen in these later stages. However, it may be that feedback and other regulatory loops are involved, as proposed for the levels of other BR intermediates in BL-deficient mutants (Hong et al., 2003; Tanabe et al., 2005).

For the CR26-1-6 plants containing p326 operably linked to the ZmDWF4 cDNA, there was an ~6-fold increase in 6-deoxocathasterone levels, and an increase in the concentrations of all downstream BR intermediates (approximately doubled relative to wild-type). This means that the conversion of campestanol to 6-deoxocathasterone in the late C-6 oxidation pathway was also enhanced by the ZmDWF4 transgene. No changes in the early C-6 oxidation pathway were observed in any of the p326:DWF4 or p326:ZmDWF4 plants.

The results provide direct evidence that a) heterologous DWF4 polypeptide can stimulate the BL biosynthesis pathway in a plant by enhancing a single rate-limiting step, the conversion of campestanol to 6-deoxocathasterone in the late C-6 oxidation pathway in rice. The results with campestanol and 6-deoxocathasterone suggest that BL levels are increased in p326 DWF4 rice plants.

Summary and Discussion

Direct GC-MS measurements of chemical intermediates in the BL biosynthesis pathway show that T3 rice plants containing the p326 promoter operably linked to the DWF4 gDNA, as well other rice plants containing a construct involving a corn DWF4 ortholog, are more effective in the conversion of campestanol to 6-deoxocathasterone. This is the step in the BL biosynthesis pathway that is catalyzed by DWF4.

One of the effects of a DWF4 transgene is to enhance photosynthetic capacity, e.g., as measured by capture of $CO_2$ by rice flag leaves (see below). Promoter p326 may drive expression in the source tissues, and the mis-expression of DWF4 genes in these tissues may result in a more efficient conversion of campestanol to 6-deoxocathasterone and the accumulation of BL in these tissues. BL is not transported far in a plant, and the increased BL levels may act somewhat locally to stimulate the capture of $CO_2$ and conversion to sucrose. This sucrose may be loaded into the phloem and transported to the seeds, enhancing seed filling and possibly providing an additional and as yet unknown stimulus for the production of more tillers (data not shown) and more seeds. The increase in BL also may act on the walls of the leaf cells and make them more able to expand under turgor pressure.

The CR24-3-6 and CR26-1-6 plants demonstrate an ~2-fold to an ~6-fold increase in 6-deoxocathasterone levels, and an up to an ~2-fold increase in the levels of the downstream intermediates.

Example 11

Evaluation of Photosynthetic Efficiency of Transgenic Plants

Summary

LiCor was used to perform photosynthesis (PS) measurements of flag leaves on homozygous T3 plants carrying the direct fusion construct p326-DWF4 (CR24). The PS rate of transgenic plants was significantly higher in one line than the wild type plants at two $CO_2$ concentrations, 380 ppm and 760 ppm. The PS rate of the other line tended to be higher relative to the control, but was not statistically significantly higher.

Materials And Methods

Plants Containing p326:DWF4 Direct Fusions

The DWF4 gDNA was operably linked to the p326 promoter and the OCS terminator, as in Example 10 resulting in the construct CR24. CR24 was transformed into rice using *Agrobacterium*-mediated transformation and homozygous lines were produced. Homozygous T3 plants representing each of the lines CR24-3-6 and CR24-5-6 were grown alongside untransformed wild types in the greenhouse. Plants at flowering stage were moved to a Conviron growth chamber for adaptation before LiCor measurement. The growth condition in the Conviron was 16 h light at 28° C. and 8 h dark at 25° C. Three plants from each of the transgenic lines as well the control were measured with the LiCor meter.

LiCor Measurement

Photosynthetic gas exchange was determined using a Li-Cor 6400 (Li-Cor Inc. Lincoln, Nebr.) portable photosynthesis system fitted with a 2 by 3 cm leaf chamber and a fixed LED light source (6400-02B) using an array of red and blue LEDs. Light response curves for each sample was determined at 2 different $CO_2$ concentrations (380 µl l$^{-1}$ and 760 µl l$^{-1}$) and 9 different light intensities ranging from 0-2000 µmol m$^{-2}$s$^{-1}$. Measurements were made at the mid point on the flag leaf at flowering stage. The leaf area within the chamber was estimated by multiplying the average width of the leaf times the length (3 cm) of the chamber and this variable was used in the photosynthetic rate calculation. Leaf temperature was controlled at 25° C., chamber humidity was maintained between 50-55%, and flow rate was constant at 500 µmol s$^{-1}$. Leaves were equilibrated in the chamber at an irradiance of 1500 µmol m$^{-2}$s$^{-1}$. Subsequently photosynthetic rates were logged when rates reach a steady-state, for each given light intensity, with a minimum wait time of 120 s and maximum of 200 s.

Results

As shown in FIG. 2, transgenic line CR24-3-6 had a PS rate that was higher than a non-transgenic control at light intensities of 500 µmol m$^{-2}$s$^{-1}$ to 2000 µmol m$^{-2}$s$^{-1}$ and 380 ppm $CO_2$. The PS rate appeared to decrease at 2000 µmol m$^{-2}$s$^{-1}$ for control plants but not for CR24-3-6 plants. The PS rate for line CR24-5-6 was also consistently higher than the rate for controls at 500 through 2000 µmol m$^{-2}$ s$^{-1}$ and 380 ppm $CO_2$.

The PS rate was also measured at a $CO_2$ concentration of 760 ppm. The PS rates of lines CR24-3-6 and CR24-5-6 were also consistently higher than the PS rate of the non-transgenic control at the same light intensities and 760 ppm of $CO_2$ (data not shown). These data clearly indicate that plants overexpressing a C-22 α hydroxylase polypeptide cari have an increased photosynthetic rate in leaves. It seems likely that this increase in $CO_2$ fixation is at least in part responsible for the plant size and seed yield phenotypes described above.

Example 12

GC-MS Analysis of p326:DWF4 Expression in Rice

Materials And Methods

Promoter and Coding Sequence

A Ti plasmid (CRS-BIN1A) containing the p326 promoter upstream of Hap1, and upstream of $UAS_{Hap1}$ and a sequence encoding GFP, was introduced into the rice cultivar Kitaake by utilizing *Agrobacterium* and transformation-competent callus. Stimulation of the promoter results in the accumulation of Hap1 protein and GFP. Detectable expression of GFP is confined to the root, stem and leaves of rice plants. Expression cannot be detected in the shoot meristem, the flowers, or the seeds prior to germination. A Ti plasmid (DWF4-BIN1B) containing five copies of the $UAS_{Hap1}$ upstream of the DWF4 gDNA was also introduced into Kitaake. The gDNA was from ecotype WS (SEQ ID NO: 14). Activation of the UAS (by Hap1) resulted in transcription of the DWF4 gDNA and accumulation of DWF4 transcript.

Crosses, Genotyping and Pairing of T2 Plants

UAS:DWF4 lines DWF4-BIN1B 16-2, 17-3 and 27-3, derived from the independent transgenic lines 16, 17 and 27, respectively, were pollinated by the progeny of the p326: Hap1 line CRS-BIN1A 7 to produce F1 seeds. The three groups of F1 plants termed R148, R150 and R151, respectively, were tested for the presence of Hap1:GFP by fluorescence, and for the presence of the UAS:DWF4 by PCR, and the presence of DWF4 gDNA transcript was confirmed by RT-PCR. F2 seeds from the F1 plants R148P5, R150P7 and R151P1 were germinated and grown in the dark for 3 days, and then also tested for the presence of p326:Hap1 and UAS: DWF4. Five pairs of GFP(+)/DWF4(+) and GFP(+)/ DWF4(-) segregants, each arising from the same F1 plant, were grown side-by-side in 5 pots, as shown in Table 9.

TABLE 9

Table 9. Pairing of Plants. GFP(+)/DWF4(+) and GFP(+)/DWF4(−) F2 segregants were grown side-by-side. Hap1:GFP and UAS:DWF4 signify the two elements of the 2-component system.

| T2 Abbreviation | Hap1:GFP | UAS:DWF4 | Pair |
|---|---|---|---|
| R148P5-13 | Present | Absent | 1 |
| R148P5-12 | Present | Present | |
| R148P5-14 | Present | Absent | 2 |
| R148P5-15 | Present | Present | |
| R150P7-14 | Present | Absent | 3 |
| R150P7-19 | Present | Present | |
| R150P7-18 | Present | Absent | 4 |
| R150P7-20 | Present | Present | |
| R151P1-41 | Present | Absent | 5 |
| R151P1-40 | Present | Absent | |

Plants Containing p326:DWF4 Direct Fusions

The DWF4 gDNA was operably linked to the p326 promoter and the OCS terminator, as in Example 10 resulting in the construct CR24. CR24 was transformed into rice using *Agrobacterium*-mediated transformation and homozygous lines were produced. Ten homozygous T3 plants representing each of the lines CR24-3-6 and CR24-5-6 were grown alongside five untransformed wild types in a greenhouse.

Extraction and Chemical Analysis of Flag Leaves

All plants were grown in a greenhouse. The flag leaf from each plant was collected ~12 days after initiation of flowering and within 5 minutes of the other flag leaves (between 5:00 pm and 5:05 pm). Developing seeds were collected 15 days after flowering and 15 days after pollination, also within 5 minutes of the other seed leaves and between 5:00 pm and 5:05 pm. All tissues were frozen on dry ice and stored at −80° C. For chemical analysis, these leaves were lyophilized, extracted with methanol and dichloromethane, and partitioned into polar and non-polar phases before derivitization and GC-MS. The extractions were done in duplicate or triplicate to generate replicate samples for GC-MS analysis. The amount of lyophilized leaf tissue used for each extraction is shown in Table 10.

The data collection and processing involved visual inspection and comparison of chromatograms, multivariate analysis including principal component analysis (PCA) and hierarchical clustering analysis (HCA), and experimental/control analysis used to determine metabolite ratios. The 82 compounds analyzed included amino acids, carbohydrates, fatty acids and organic acids, as shown above.

TABLE 10

Table 10. Samples used for MxP Analysis. The T2 abbreviation refers to each of the 10 flag leaves used for GC-MS analysis. Columns '1', '2' and '3' show the amount of lyophilized leaf tissue used for each extraction, in mg. For two of the flag leaves (R148P5 14 and R151P1 40), there was only enough tissue for duplicate extractions.

| T2 Abbreviation | 1 | 2 | 3 |
|---|---|---|---|
| R148P5 13 | 28.9 | 29.1 | 30.1 |
| R148P5 12 | 29.8 | 29.7 | 32.0 |
| R148P5 14 | 29.9 | 28.6 | — |
| R148P5 15 | 29.5 | 29.2 | 22.7 |
| R150P7 14 | 29.3 | 30.0 | 29.6 |
| R150P7 19 | 28.6 | 30.2 | 30.0 |
| R150P7 18 | 31.2 | 29.6 | 30.4 |
| R150P7 20 | 29.7 | 30.0 | 27.4 |
| R151P1 41 | 28.9 | 27.4 | 28.5 |
| R151P1 40 | 29.5 | 19.2 | — |

Results

GC-MS was used to analyze 82 compounds including amino acids, carbohydrates, fatty acids and organic acids present in the flag leaves of 5 pairs of F2 rice plants, and in the flag leaves and seeds of two groups of 10 T3 rice plants, each containing active DWF4 transgenes. The MxP results show that the leaves from 2 out of 5 F2 plants (R148P5 15 and R151P1 40) containing p326:Hap1 and UAS:DWF4 (GFP(+)/DWF4(+) plants) contained an ~20% increase in the concentration of free sucrose relative to segregant control plants (R148P5 14 and R151P1 41 respectively) containing p326:Hap1 only (GFP(+)/DWF4(+) plants). The flag leaves from the 3 others (R148P5 12, R150P7 19 and R150P720) showed slight increases in sucrose levels as well. Although not statistically significant, the sucrose concentrations in all 3 of these other plants trended slightly higher rather than lower.

All 5 GFP(+)/DWF4(+) F2 plants showed higher levels of glutamic acid and linoleic acid (C18:2) than the GFP(+)/DWF4(−) controls. The increase for glutamic acid was between ~15% and ~65%, and for linoleic acid it was between ~18% and ~40%.

The concentrations of the other 79 compounds analyzed in the 5 GFP(+)/DWF4(+) flag leaves trended either slightly higher or slightly lower than in the GFP(+)/DWF4(−) controls. These included glucose and fructose, from which sucrose is made, and glutamine, which is synthesized from glutamic acid.

Metabolic profiling of flag leaves from T3 plants containing the p326:DWF4 gDNA as a direct fusion did not show statistically significant increases in sucrose or linoleic acid levels relative to untransformed wild-type controls; one T3 line (CR24-3-6) was statistically higher in glutamic acid.

Metabolic profiling of developing seeds collected 15 days after pollination of other T3 plants containing the DWF4 gDNA as a direct fusion construct did not show statistically significant differences in sucrose, glutamic acid or linoleic acid levels relative to untransformed wild-type controls.

There was no trend in the levels of 79 other compounds. Principle component analysis showed that L-threonine, L-valine, L-phenylalanine, glycerol, L-leucine and L-lysine (Component 1) contribute ~34% of all of the variation in the seed compounds.

Summary And Discussion

By utilizing rice flag leaves, MxP analysis of a series of F2 plants was performed. Comparison of MxP data from GFP(+)/DWF4(+) and GFP(+)/DWF4(−) plants revealed that there was increased glutamic acid, linoleic acid, and possibly sucrose levels in plants containing p326:Hap1 and UAS:DWF4 relative to controls containing p326:Hap1 only.

The invention being thus described, it will be apparent to one of ordinary skill in the art that various modifications of the materials and methods for practicing the invention can be made. Such modifications are to be considered within the scope of the invention as defined by the following claims.

What is claimed is:

1. A transgenic plant comprising at least one exogenous polynucleotide, said at least one exogenous polynucleotide comprising a nucleic acid encoding a cytochrome P450 polypeptide having 22-α hydroxylase activity, said polypeptide having 85% or greater sequence identity to the amino acid sequence set forth in SEQ ID NO:2, wherein said exogenous polynucleotide further comprises a control element operably linked to said nucleic acid encoding said polypeptide, wherein said control element is a broadly expressing promoter or a constitutive promoter, and wherein said plant has an increased height relative to a control plant, an increased plant weight relative to a control plant, an increased seed weight relative to a control plant, an increased seed yield relative to a control plant, an increase in a level of 6-deoxocathasterone relative to a control plant, or a decrease in a level of campestanol relative to a control plant.

2. The transgenic plant of claim 1, wherein said cytochrome P450 polypeptide has 95% or greater sequence identity to the amino acid sequence set forth in SEQ ID NO:2.

3. The transgenic plant of claim 1, wherein said plant is a monocot.

4. The transgenic plant of claim 3, wherein said plant is a rice plant.

5. The transgenic plant of claim 3, wherein said plant is a wheat plant.

6. The transgenic plant of claim 3, wherein said plant is a switchgrass plant.

7. The transgenic plant of claim 3, wherein said plant is a rye plant.

8. The transgenic plant of claim 3, wherein said plant is a barley plant.

9. The transgenic plant of claim 3, wherein said plant is a sorghum plant.

10. The transgenic plant of claim 3, wherein said plant is a corn plant.

11. The transgenic plant of claim 3, wherein said plant is a palm plant.

12. The transgenic plant of claim 1, wherein said plant is a dicot.

13. The transgenic plant of claim 12, wherein said plant is a soybean plant.

14. The transgenic plant of claim 12, wherein said plant is a safflower plant.

15. The transgenic plant of claim 12, wherein said plant is an alfalfa plant.

16. The transgenic plant of claim 12, wherein said plant is a rapeseed plant.

17. The transgenic plant of claim 12, wherein said plant is a sunflower plant.

18. The transgenic plant of claim 12, wherein said plant is a coffee plant.

19. The transgenic plant of claim 12, wherein said plant is in the Euphorbiaceae family.

20. The transgenic plant of claim 1, wherein said plant has an increased height relative to a control plant.

21. The transgenic plant of claim 1, wherein said plant has an increased plant weight relative to a control plant.

22. The transgenic plant of claim 1, wherein said plant has an increased seed weight relative to a control plant.

23. The transgenic plant of claim 1, wherein said plant has an increased seed yield relative to a control plant.

24. The transgenic plant of claim 1, wherein said plant has an increase in a level of 6-deoxocathasterone relative to a control plant.

25. The transgenic plant of claim 1, wherein said plant has a decrease in a level of campestanol relative to a control plant.

* * * * *

UNITED STATES PATENT AND TRADEMARK OFFICE
CERTIFICATE OF CORRECTION

| | | |
|---|---|---|
| PATENT NO. | : 7,897,839 B2 | Page 1 of 1 |
| APPLICATION NO. | : 11/112824 | |
| DATED | : March 1, 2011 | |
| INVENTOR(S) | : Pennell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this
Fourth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,897,839 B2 | Page 1 of 1 |
| APPLICATION NO. | : 11/112824 | |
| DATED | : March 1, 2011 | |
| INVENTOR(S) | : Pennell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this
Twenty-seventh Day of November, 2012

David J. Kappos
*Director of the United States Patent and Trademark Office*